US009790202B2

(12) United States Patent
Fischer et al.

(10) Patent No.: US 9,790,202 B2
(45) Date of Patent: Oct. 17, 2017

(54) ANTHRANILAMIDE DERIVATIVES AS PESTICIDES

(75) Inventors: Rüdiger Fischer, Pulheim (DE); Ernst Rudolf Gesing, Erkrath (DE); Christoph Grondal, Köln (DE); Markus Heil, Leichlingen (DE); Heinz-Juergen Wroblowsky, Langenfeld (DE); Arnd Voerste, Köln (DE); Ulrich Gorgens, Ratingen (DE)

(73) Assignee: BAYER INTELLECTUAL PROPERTY GMBH, Monheim am Rhein (DE)

( * ) Notice: Subject to any disclaimer, the term of this patent is extended or adjusted under 35 U.S.C. 154(b) by 48 days.

(21) Appl. No.: 13/179,217

(22) Filed: Jul. 8, 2011

(65) Prior Publication Data

US 2012/0010250 A1 Jan. 12, 2012

Related U.S. Application Data

(60) Provisional application No. 61/362,727, filed on Jul. 9, 2010.

(30) Foreign Application Priority Data

Jul. 9, 2010 (EP) .................................... 10168991

(51) Int. Cl.

| | |
|---|---|
| ***C07D 401/00*** | (2006.01) |
| ***A01N 43/40*** | (2006.01) |
| ***C07D 401/14*** | (2006.01) |
| ***C07D 403/06*** | (2006.01) |
| ***C07D 405/14*** | (2006.01) |

(52) U.S. Cl.

CPC ......... *C07D 401/14* (2013.01); *C07D 403/06* (2013.01); *C07D 405/14* (2013.01)

(58) Field of Classification Search

CPC ............................ C07D 403/06; C07D 405/14
USPC ................... 514/341, 381; 546/272.4, 275.4; 548/253

See application file for complete search history.

(56) References Cited

U.S. PATENT DOCUMENTS 6,747,047 B2 * 6/2004 Lahm ..................... A01N 37/22 514/341
6,995,178 B2 * 2/2006 Lahm et al. .................. 514/354
7,612,100 B2 11/2009 Koyanagi et al.
7,674,807 B2 * 3/2010 Wada ..................... A01N 43/36 514/351
8,101,550 B2 1/2012 Alig et al.
8,324,390 B2 * 12/2012 Fischer ................ A01N 43/713 546/275.4
8,658,570 B2 * 2/2014 Fischer ................ A01N 43/713 504/341
8,821,898 B2 * 9/2014 Funke .................... A01N 43/56 424/400
9,056,861 B2 * 6/2015 Pazenok .............. A01N 43/713
9,265,255 B2 * 2/2016 Funke .................. A01N 43/713
2006/0281780 A1 12/2006 Goto et al.
2007/0129407 A1 * 6/2007 Koyanagi et al. ............ 514/341
2008/0305955 A1 12/2008 Bretschneider et al.
2009/0076282 A1 3/2009 Toriyabe et al.
2009/0247551 A1 10/2009 Jeschke et al.
2009/0253749 A1 10/2009 Jeschke et al.
2009/0269300 A1 10/2009 Finkelstein et al.
2010/0029478 A1 2/2010 Alig et al.
2010/0048578 A1 2/2010 Jachmann et al.
2010/0048640 A1 2/2010 Jachmann et al.
2010/0240705 A1 9/2010 Jeschke et al.
2010/0256195 A1 10/2010 Fischer et al.

FOREIGN PATENT DOCUMENTS

CA 2 671 179 6/2008
DE 10 2006 032 168 12/2007
EP 0 539 588 5/1993

(Continued)

OTHER PUBLICATIONS

International Search Report based on Application No. PCT/EP2011/061171 dated Aug. 18, 2011.

Baur et al.; "Polydisperse Ethoxylated Fatty Alcohol Surfactants as Accelerators of Cuticular Penetration. 1. Effects of Ethoxy Chain Length and the Size of the Penetrants"; Pestic. Sci.; 1997; vol. 51; pp. 131-152; Sci.

Ban et al.; "Synthesis and Biological Activity of Novel 4-Phenyl-1,8-Naphthyridin-2(1H)—ON-3-Yl Ureas: Potent Acyl-COA:Cholesterol Acyltransferase Inhibitor With Improved Aqueous Solubility"; Bioorganic & Medicinal Chemistry Letters; 2006; vol. 16; pp. 44-48; Elsevier.

(Continued)

*Primary Examiner* — Sabiha N Qazi
(74) *Attorney, Agent, or Firm* — McBee Moore Woodward & Vanik IP, LLC; Susan McBee; David Woodward

(57) ABSTRACT

The present invention relates to novel anthranilamide derivatives of the general formula (I)

(I)

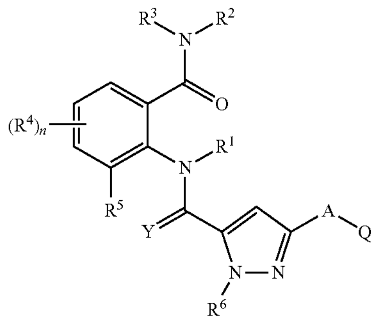

in which $R^1$, $R^2$, $R^3$, $R^4$, $R^5$, $R^6$, A, Q, Y and n are each as defined in the description—, to the use thereof as insecticides and acaricides for control of animal pests, and to several processes for preparation thereof.

20 Claims, No Drawings

(56) References Cited

FOREIGN PATENT DOCUMENTS

| | | |
|---|---|---|
| WO | 0170671 | 9/2001 |
| WO | 03015518 | 2/2003 |
| WO | 03015519 | 2/2003 |
| WO | 03016282 | 2/2003 |
| WO | 03016283 | 2/2003 |
| WO | 03016284 | 2/2003 |
| WO | 03242222 | 3/2003 |
| WO | 03027099 | 4/2003 |
| WO | 03062226 | 7/2003 |
| WO | 2004/027042 | 4/2004 |
| WO | 2004027042 | 4/2004 |
| WO | 2004033468 | 4/2004 |
| WO | 2004046129 | 6/2004 |
| WO | 2004067528 | 8/2004 |
| WO | 2005/035486 | 4/2005 |
| WO | 2005077934 | 8/2005 |
| WO | 2005085234 | 9/2005 |
| WO | 2005118552 | 12/2005 |
| WO | 2006000336 | 1/2006 |
| WO | 2006023783 | 3/2006 |
| WO | 2006/043635 | 4/2006 |
| WO | 2006040113 | 4/2006 |
| WO | 2006/056433 | 6/2006 |
| WO | 2006/089633 | 8/2006 |
| WO | 2006/100288 | 9/2006 |
| WO | 2006/108591 | 10/2006 |
| WO | 2006111341 | 10/2006 |
| WO | 2006/129714 | 12/2006 |
| WO | 2007006670 | 1/2007 |
| WO | 2007020877 | 2/2007 |
| WO | 2007024833 | 3/2007 |
| WO | 2007/043677 | 4/2007 |
| WO | 2007043677 | 4/2007 |
| WO | 2007/057407 | 5/2007 |
| WO | 2007/095229 | 8/2007 |
| WO | 2007/115643 | 10/2007 |
| WO | 2007/115644 | 10/2007 |
| WO | 2007/115646 | 10/2007 |
| WO | 2007/149134 | 12/2007 |
| WO | 2007144100 | 12/2007 |
| WO | 2008/067911 | 6/2008 |
| WO | 2008/104503 | 9/2008 |
| WO | 2008126889 | 10/2008 |
| WO | 2008126890 | 10/2008 |
| WO | 2008126933 | 10/2008 |
| WO | 2009/061991 | 5/2009 |
| WO | 2010/069502 | 6/2010 |

OTHER PUBLICATIONS

Baumgarth et al.; "Bicyclic Acylguanidine Na+/H+ Antiporter Inhibitors"; J. Med. Chem.; 1998; vol. 41; pp. 3736-3747; American Chemical Society.

Udd et al.; "Copper-Catalyzed Cyclization of Z-Oximes Into 3-Methyl-1,2-Benzisoxazoles"; Tetrahedron Letters; 2010; vol. 51; pp. 1030-1033; Elsevier.

* cited by examiner

ANTHRANILAMIDE DERIVATIVES AS PESTICIDES

CROSS REFERENCE TO RELATED APPLICATIONS

This application claims priority to EP 10168991.7 filed Jul. 9, 2010 and U.S. 61/362,727 filed Jul. 9, 2010, the entire contents of which are incorporated herein by reference in their entireties.

BACKGROUND

Field of the Invention

The present invention relates to novel anthranilamide derivatives, to the use thereof as insecticides and acaricides for control of animal pests, and to several processes for preparation thereof.

Description of Related Art

Anthranilic acid derivatives having insecticidal properties have already been described in the literature, as for example in WO 01/70671, WO 03/015519, WO 03/016284, WO 03/015518, WO 03/024222, WO 03/016282, WO 03/016283, WO 03/062226, WO 03/027099, WO 04/027042, WO 04/033468, WO 2004/046129, WO 2004/067528, WO 2005/118552, WO 2005/077934, WO 2005/085234, WO 2006/023783, WO 2006/000336, WO 2006/040113, WO 2006/111341, WO 2007/006670, WO 2007/024833, WO2007/020877, WO 2007/144100, WO2007/043677, WO2008/126889, WO2008/126890, WO2008/126933.

However, the active ingredients already known according to the documents cited above have some disadvantages on application, whether because they exhibit only a narrow range of application or whether because they do not have satisfactory insecticidal or acaricidal activity.

SUMMARY

Novel anthranilic acid derivatives have now been found, which have advantages over the compounds already known, examples being better biological or environmental properties, a wider range of application methods, a better insecticidal or acaricidal activity, and also good compatibility with crop plants. The anthranilic acid derivatives can be used in combination with further agents for enhancing efficacy, particularly towards insects which are difficult to control.

The present invention accordingly provides novel anthranilamide derivatives of the formula (I)

(I)

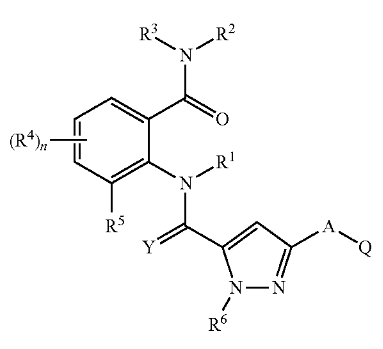

in which $R^1$ is hydrogen, amino, hydroxyl or in each case optionally singly or multiply, identically or differently substituted $C_1$-$C_6$-alkyl, $C_2$-$C_6$-alkenyl, $C_2$-$C_6$-alkynyl or $C_3$-$C_6$-cycloalkyl, where the substituents may each independently be selected from halogen, cyano, nitro, hydroxyl, $C_1$-$C_4$-alkoxy, $C_1$-$C_4$-alkylthio, $C_1$-$C_4$-alkylsulphinyl, $C_1$-$C_4$-alkylsulphonyl, ($C_1$-$C_4$-alkoxy)carbonyl, $C_1$-$C_4$-alkylamino, di-($C_1$-$C_4$-alkyl)amino, $C_3$-$C_6$-cycloalkylamino and ($C_1$-$C_4$-alkyl)$C_3$-$C_6$-cycloalkylamino, $R^2$ is hydrogen, $C_1$-$C_6$-alkyl, $C_2$-$C_6$-alkenyl, $C_2$-$C_6$-alkynyl, $C_3$-$C_6$-cycloalkyl, $C_1$-$C_4$-alkoxy, $C_1$-$C_4$-alkylamino, di-($C_1$-$C_4$-alkyl)amino, $C_3$-$C_6$-cycloalkylamino, $C_2$-$C_6$-alkoxycarbonyl or $C_2$-$C_6$-alkylcarbonyl, $R^3$ is hydrogen or in each case optionally singly or multiply, identically or differently substituted $C_1$-$C_6$-alkyl, $C_1$-$C_6$-alkoxy, $C_2$-$C_6$-alkenyl, $C_2$-$C_6$-alkynyl, where the substituents may each independently be selected from halogen, cyano, nitro, hydroxyl, $C_1$-$C_6$-alkyl, $C_3$-$C_6$-cycloalkyl, $C_1$-$C_4$-alkoxy, $C_1$-$C_4$-haloalkoxy, $C_1$-$C_4$-alkylthio, $C_1$-$C_4$-alkylsulphinyl, $C_1$-$C_4$-alkylsulphonyl, $C_1$-$C_4$-alkylsulphimino, $C_1$-$C_4$-alkylsulphimino-$C_1$-$C_4$-alkyl, $C_1$-$C_4$-alkylsulphimino-$C_2$-$C_5$-alkylcarbonyl, $C_1$-$C_4$-alkylsulphoximino, $C_1$-$C_4$-alkylsulphoximino-$C_1$-$C_4$-alkyl, $C_1$-$C_4$-alkylsulphoximino-$C_2$-$C_5$-alkylcarbonyl, $C_2$-$C_6$-alkoxycarbonyl, $C_2$-$C_6$-alkylcarbonyl and $C_3$-$C_6$-trialkylsilyl, $R^3$ is also in each case optionally singly or multiply, identically or differently substituted $C_1$-$C_6$-alkyl, $C_1$-$C_6$-alkoxy, $C_2$-$C_6$-alkenyl, $C_2$-$C_6$-alkynyl, where the substituents may each independently be selected from amino, $C_3$-$C_6$-cycloalkylamino or a 5- or 6-membered heteroaromatic ring, $R^3$ is likewise also $C_3$-$C_{12}$-cycloalkyl, $C_3$-$C_{12}$-cycloalkyl-$C_1$-$C_6$-alkyl and $C_4$-$C_{12}$-bicycloalkyl, where the substituents may each independently be selected from halogen, cyano, nitro, hydroxyl, amino, $C_1$-$C_6$-alkyl, $C_3$-$C_6$-cycloalkyl, $C_3$-$C_6$-cycloalkylamino, $C_1$-$C_4$-alkoxy, $C_1$-$C_4$-haloalkoxy, $C_1$-$C_4$-alkylthio, $C_1$-$C_4$-alkylsulphinyl, $C_1$-$C_4$-alkylsulphonyl, $C_1$-$C_4$-alkylsulphimino, $C_1$-$C_4$-alkylsulphimino-$C_1$-$C_4$-alkyl, $C_1$-$C_4$-alkylsulphimino-$C_2$-$C_5$-alkylcarbonyl, $C_1$-$C_4$-alkylsulphoximino, $C_1$-$C_4$-alkylsulphoximino-$C_1$-$C_4$-alkyl, $C_1$-$C_4$-alkylsulphoximino-$C_2$-$C_5$-alkylcarbonyl, $C_2$-$C_6$-alkoxycarbonyl, $C_2$-$C_6$-alkylcarbonyl, $C_3$-$C_6$-trialkylsilyl or a 5- or 6-membered heteroaromatic ring, $R^2$ and $R^3$ may be joined to one another via two to six carbon atoms and form a ring which optionally additionally contains a further nitrogen, sulphur or oxygen atom and may optionally be mono- to tetrasubstituted by $C_1$-$C_2$-alkyl, halogen, cyano, amino or $C_1$-$C_2$-alkoxy, $R^2$, $R^3$ together are also $=S(C_1$-$C_4$-alkyl$)_2$, $=S(O)(C_1$-$C_4$-alkyl$)_2$, Y is O or S, $R^4$ is hydroxyl, amino, carboxyl, OCN, SCN, $C_1$-$C_4$-alkoxy-$C_1$-$C_4$-alkyl, $C_1$-$C_4$-alkylthio-$C_1$-$C_4$-alkyl, $C_1$-$C_4$-alkylsulphonyloxy, $C_1$-$C_4$-alkylcarbonylamino, N-methoxy-N-methylamino, hydroxyimino, ($C_1$-$C_4$-alkyl)hydroxyimino, $C_1$-$C_4$-alkoxycarbonyl, $C_1$-$C_4$-alkoxycarbonyl-$C_1$-$C_4$-alkyl, $C_1$-$C_4$-alkylcarbonyl, hydroxy-$C_1$-$C_4$-alkyl, $C_1$-$C_4$-haloalkylcarbonyl, $C_1$-$C_4$-alkylcarbonyloxy, aminocarbonyl, $C_1$-$C_4$-alkylaminocarbonyl, $C_1$-$C_4$-dialkylaminocarbonyl, aminothiocarbonyl, $C_1$-$C_4$-alkylaminothiocarbonyl, $C_1$-$C_4$-dialkylaminothiocarbonyl, $C_1$-$C_4$-alkylsulphonylamino, aminosulphonyl, $C_1$-$C_4$-alkylaminosulphonyl, $C_1$-$C_4$-dialkylaminosulphonyl, $C_1$-$C_4$-alkylsulphoximino or a 3- to 6-membered saturated, partly saturated or aromatic ring which may optionally contain one to three heteroatoms from the group of O, S and N and which is optionally mono- or polysubstituted identically or differently by halogen, cyano, nitro, hydroxyl, amino, carboxyl, $C_1$-$C_4$-alkyl, $C_1$-$C_4$-haloalkyl, $C_2$-$C_6$-alkenyl, $C_2$-$C_6$-haloalkenyl, $C_2$-$C_6$-alkynyl, $C_1$-$C_4$-alkoxy, $C_1$-$C_4$-haloalkoxy, $C_1$-$C_4$-alkylthio, $C_1$-$C_4$-alkylsulphinyl, $C_1$-$C_4$-alkylsulphonyl, $C_1$-$C_4$-alkylsulphonyloxy, $C_1$-$C_4$-haloalkylthio, $C_1$-$C_4$-haloalkylsulphinyl, $C_1$-$C_4$-haloalkylsulphonyl, $C_1$-$C_4$-alkylamino, di-($C_1$-$C_4$-alkyl)amino, $C_1$-$C_4$-alkylcarbonylamino, $C_1$-$C_4$-alkoxycarbonyl, $C_1$-$C_4$-alkylcarbonyl, $C_1$-$C_4$-alkylcarbonyloxy, aminocarbonyl, $C_1$-$C_4$-alkylaminocarbonyl, $C_1$-$C_4$-dialkylaminocarbonyl, aminothiocarbonyl, $C_1$-$C_4$-alkylaminothiocarbonyl, $C_1$-$C_4$-dialkylaminothiocarbonyl, $C_3$-$C_6$-cycloalkylamino, $C_1$-$C_4$-alkylsulphonylamino, aminosulphonyl, $C_1$-$C_4$-alkylaminosulphonyl or $C_1$-$C_4$-dialkylaminosulphonyl, $R^4$ additionally has the following definitions if Y is S:

$R^4$ is additionally hydrogen, halogen, cyano, nitro $C_1$-$C_4$-alkyl, $C_1$-$C_4$-haloalkyl, $C_2$-$C_6$-alkenyl, $C_2$-$C_6$-haloalkenyl, $C_2$-$C_6$-alkynyl, $C_1$-$C_4$-alkoxy, $C_1$-$C_4$-haloalkoxy, $SF_5$, $C_1$-$C_4$-alkylthio, $C_1$-$C_4$-alkylsulphinyl, $C_1$-$C_4$-alkylsulphonyl, $C_1$-$C_4$-haloalkylthio, $C_1$-$C_4$-haloalkylsulphinyl, $C_1$-$C_4$-haloalkylsulphonyl, $C_1$-$C_4$-alkylamino, di-($C_1$-$C_4$-alkyl)amino, $C_3$-$C_6$-cycloalkylamino, ($C_1$-$C_4$-alkoxy)imino, ($C_1$-$C_4$-alkyl)($C_1$-$C_4$-alkoxy)imino, ($C_1$-$C_4$-haloalkyl)($C_1$-$C_4$-alkoxy)imino or $C_3$-$C_6$-trialkylsilyl, or two $R^4$ additionally form, via adjacent carbon atoms, a ring which is $—(CH_2)_3—$, $—(CH_2)_4—$, $—(CH_2)_5—$, $—(CH{=}CH—)_2—$, $—OCH_2O—$, $—O(CH_2)_2O—$, $—OCF_2O—$, $—(CF_2)_2O—$, $—O(CF_2)_2O—$, $—(CH{=}CH—CH{=}N)—$ or $—(CH{=}CH—N{=}CH)—$, two $R^4$ additionally also form, via adjacent carbon atoms, the following fused rings which are optionally mono- or polysubstituted identically or differently, where the substituents may each independently be selected from hydrogen, $C_1$-$C_6$-alkyl, $C_3$-$C_6$-cycloalkyl, $C_1$-$C_6$-haloalkyl, $C_3$-$C_6$-halocycloalkyl, halogen, $C_1$-$C_6$-alkoxy, $C_1$-$C_4$-alkylthio($C_1$-$C_6$-alkyl), $C_1$-$C_4$-alkylsulfinyl($C_1$-$C_4$-alkylsulfonyl($C_1$-$C_6$-alkyl), $C_1$-$C_4$-alkylamino, di-($C_1$-$C_4$-alkyl)amino and $C_3$-$C_6$-cycloalkylamino,

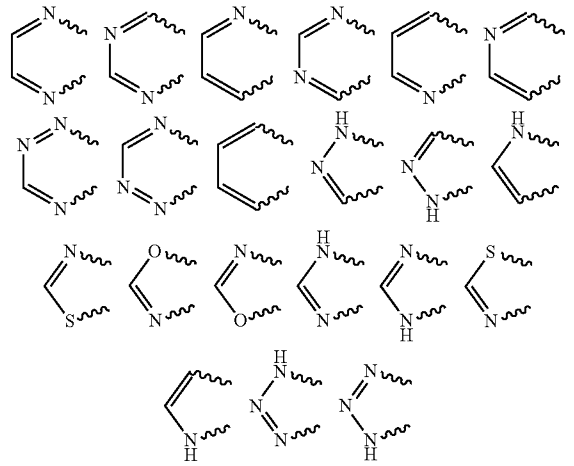

n is 0 to 3, $R^5$ is $C_1$-$C_6$-alkyl, $C_3$-$C_6$-cycloalkyl, $C_1$-$C_6$-haloalkyl, $C_1$-$C_6$-halocycloalkyl, $C_2$-$C_6$-alkenyl, $C_2$-$C_6$-haloalkenyl, $C_2$-$C_6$-alkynyl, $C_2$-$C_6$-haloalkynyl, $C_1$-$C_4$-alkoxy, $C_1$-$C_4$-haloalkoxy, $C_1$-$C_4$-alkylthio, $C_1$-$C_4$-alkylsulphinyl, $C_1$-$C_4$-alkylsulphonyl, $C_1$-$C_4$-haloalkylthio, $C_1$-$C_4$-haloalkylsulphinyl, $C_1$-$C_4$-haloalkylsulphonyl, halogen, cyano, nitro or $C_3$-$C_6$-trialkylsilyl, $R^6$ is hydrogen, $C_1$-$C_6$-alkyl, $C_2$-$C_6$-alkenyl, $C_2$-$C_6$-alkynyl, $C_3$-$C_6$-cycloalkyl, $C_1$-$C_6$-haloalkyl, $C_2$-$C_6$-haloalkenyl or

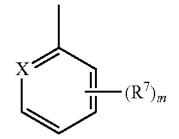

$R^6$ is also $C_3$-$C_6$-cycloalkoxy, $R^7$ is independently hydrogen, $C_1$-$C_6$-alkyl, $C_3$-$C_6$-cycloalkyl, $C_1$-$C_6$-haloalkyl, halogen, cyano, nitro, $C_1$-$C_4$-alkoxy, $C_1$-$C_4$-haloalkoxy, $C_1$-$C_4$-alkylthio or $C_1$-$C_4$-haloalkylthio, m is 0 to 4, X is N, CH, CF, CCl, CBr or Cl, A is $—CH_2—$, $—CH_2O—$, $—CH_2OCH_2—$, $—CH_2S—$, $—CH_2SCH_2—$, $—CH_2N$($C_1$-$C_6$-alkyl)-, $—CH_2N$($C_1$-$C_6$-alkyl)$CH_2—$, —CH[$CO_2$($C_1$-$C_6$-alkyl)]-, —CH(CN)—, —CH($C_1$-$C_6$-alkyl)-, —C(di-$C_1$-$C_6$-alkyl)-, $—CH_2CH_2—$, —C=NO($C_1$-$C_6$-alkyl)-, Q is a 5- or 6-membered heteroaromatic ring or an aromatic 8-, 9- or 10-membered fused heterobicyclic ring system, where the ring or ring system is optionally mono- or polysubstituted identically or differently, and where the substituents may each independently be selected from hydrogen, $C_1$-$C_6$-alkyl, $C_2$-$C_6$-alkenyl, $C_2$-$C_6$-alkynyl, $C_3$-$C_6$-cycloalkyl, $C_1$-$C_6$-haloalkyl, $C_2$-$C_6$-haloalkenyl, $C_2$-$C_6$-haloalkynyl, $C_3$-$C_6$-halocycloalkyl, halogen, CN, $CO_2H$, $CO_2NH_2$, $NO_2$, OH, $C_1$-$C_4$-alkoxy, $C_1$-$C_4$-haloalkoxy, $C_1$-$C_4$-alkylthio, $C_1$-$C_4$-alkylsulphinyl, $C_1$-$C_4$-alkylsulphonyl, $C_1$-$C_4$-haloalkylthio, $C_1$-$C_4$-haloalkylsulphinyl, $C_1$-$C_4$-haloalkylsulphonyl, $C_1$-$C_4$-alkylamino, di-($C_1$-$C_4$-alkyl)amino, $C_3$-$C_6$-cycloalkylamino, ($C_1$-$C_6$-alkyl)carbonyl, ($C_1$-$C_6$-alkoxy)carbonyl, ($C_1$-$C_6$-alkyl)aminocarbonyl, di-($C_1$-$C_4$-alkyl)aminocarbonyl, tri-($C_1$-$C_2$)alkylsilyl, ($C_1$-$C_4$-alkyl)($C_1$-$C_4$-alkoxy)imino, Q is also a 5- or 6-membered heteroaromatic or heterocyclic ring or an aromatic 8-, 9- or 10-membered fused heterobicyclic ring system, where the ring or ring system is optionally mono- or polysubstituted identically or differently, and where the substituents may each independently be selected from hydrogen, $C_1$-$C_6$-alkyl, $C_2$-$C_6$-alkenyl, $C_2$-$C_6$-alkynyl, $C_3$-$C_6$-cycloalkyl, $C_1$-$C_6$-haloalkyl, $C_2$-$C_6$-haloalkenyl, $C_2$-$C_6$-haloalkynyl, $C_3$-$C_6$-halocycloalkyl, halogen, CN, $CO_2H$, $CO_2NH_2$, $NO_2$, OH, $C_1$-$C_4$-alkoxy, $C_1$-$C_4$-haloalkoxy, $C_1$-$C_4$-alkylthio, $C_1$-$C_4$-alkylsulphinyl, $C_1$-$C_4$-alkylsulphonyl, $C_1$-$C_4$-haloalkylthio, $C_1$-$C_4$-haloalkylsulphinyl, $C_1$-$C_4$-haloalkylsulphonyl, $C_1$-$C_4$-alkylamino, di-($C_1$-$C_4$-alkyl)amino, $C_3$-$C_6$-cycloalkylamino, ($C_1$-$C_6$-alkyl)carbonyl, ($C_1$-$C_6$-alkoxy)carbonyl, ($C_1$-$C_6$-alkyl)aminocarbonyl, di-($C_1$-$C_4$-alkyl)aminocarbonyl, tri-($C_1$-$C_2$)alkylsilyl, ($C_1$-$C_4$-alkyl)($C_1$-$C_4$-alkoxy)imino, or where the substituents may each independently be selected from phenyl and a 5- or 6-membered heteroaromatic ring, where phenyl or the ring may optionally be mono- or polysubstituted identically or differently by $C_1$-$C_6$-alkyl, $C_2$-$C_6$-alkenyl, $C_2$-$C_6$-alkynyl, $C_3$-$C_6$-cycloalkyl, $C_1$-$C_6$-haloalkyl, $C_2$-$C_6$-haloalkenyl, $C_2$-$C_6$-haloalkynyl, $C_3$-$C_6$-halocycloalkyl, halogen, CN, $NO_2$, OH, $C_1$-$C_4$-alkoxy, $C_1$-$C_4$-haloalkoxy, the compounds of the general formula (I) also including N-oxides and salts.

Finally, it has been found that the inventive compounds of the formula (I) have very good insecticidal properties and can be used both in crop protection and in the protection of materials for control of undesirable pests such as insects.

DETAILED DESCRIPTION OF A PREFERRED EMBODIMENT

The inventive compounds may optionally be present as mixtures of different possible isomeric forms, especially of stereoisomers, for example, E and Z isomers, threo and erythro isomers, and optical isomers, but if appropriate also of tautomers. Both the E and the Z isomers are claimed, as are the threo and erythro isomers, and also the optical isomers, any mixtures of these isomers, and also the possible tautomeric forms.

The inventive anthranilamides are defined in general terms by the formula (I). Preferred radical definitions for the formulae specified above and below are given below. These definitions apply to the end products of the formula (I) and likewise to all intermediates.

$R^1$ is preferably hydrogen, $C_1$-$C_6$-alkyl, $C_2$-$C_6$-alkenyl, $C_2$-$C_6$-alkynyl, $C_3$-$C_6$-cycloalkyl, cyano($C_1$-$C_6$-alkyl), $C_1$-$C_6$-haloalkyl, $C_2$-$C_6$-haloalkenyl, $C_2$-$C_6$-haloalkynyl, $C_1$-$C_4$-alkoxy-$C_1$-$C_4$-alkyl, $C_1$-$C_4$-alkylthio-$C_1$-$C_4$-alkyl, $C_1$-$C_4$-alkylsulphinyl-$C_1$-$C_4$-alkyl or $C_1$-$C_4$-alkylsulphonyl-$C_1$-$C_4$-alkyl.

$R^1$ is more preferably hydrogen, methyl, cyclopropyl, cyanomethyl, methoxymethyl, methylthiomethyl, methylsulphinylmethyl or methylsulphonylmethyl.

$R^1$ is even more preferably hydrogen.

$R^2$ is preferably hydrogen or $C_1$-$C_6$-alkyl.

$R^2$ is more preferably hydrogen or methyl.

$R^2$ is even more preferably hydrogen.

$R^3$ is preferably hydrogen or in each case optionally singly or multiply, identically or differently substituted $C_1$-$C_6$-alkyl, $C_1$-$C_6$-alkoxy, $C_2$-$C_6$-alkenyl, $C_2$-$C_6$-alkynyl, where the substituents may each independently be selected from halogen, cyano, nitro, hydroxyl, $C_1$-$C_6$-alkyl, $C_3$-$C_6$-cycloalkyl, $C_1$-$C_4$-alkoxy, $C_1$-$C_4$-haloalkoxy, $C_1$-$C_4$-alkylthio, $C_1$-$C_4$-alkylsulphinyl, $C_1$-$C_4$-alkylsulphonyl, $C_1$-$C_4$-alkylsulphimino, $C_1$-$C_4$-alkylsulphimino-$C_1$-$C_4$-alkyl, $C_1$-$C_4$-alkylsulphimino-$C_2$-$C_5$-alkylcarbonyl, $C_1$-$C_4$-alkylsulphoximino, $C_1$-$C_4$-alkylsulphoximino-$C_1$-$C_4$-alkyl, $C_1$-$C_4$-alkylsulphoximino-$C_2$-$C_5$-alkylcarbonyl, $C_2$-$C_6$-alkoxycarbonyl, $C_2$-$C_6$-alkylcarbonyl and $C_3$-$C_6$-trialkylsilyl.

$R^3$ is also preferably $C_3$-$C_{12}$-cycloalkyl and $C_4$-$C_{10}$-bicycloalkyl, where the substituents may each independently be selected from halogen, cyano, nitro, hydroxyl, $C_1$-$C_6$-alkyl, $C_3$-$C_6$-cycloalkyl, $C_1$-$C_4$-alkoxy, $C_1$-$C_4$-haloalkoxy, $C_1$-$C_4$-alkylthio, $C_1$-$C_4$-alkylsulphinyl, $C_1$-$C_4$-alkylsulphonyl, $C_1$-$C_4$-alkylsulphimino, $C_1$-$C_4$-alkylsulphimino-$C_1$-$C_4$-alkyl, $C_1$-$C_4$-alkylsulphimino-$C_2$-$C_5$-alkylcarbonyl, $C_1$-$C_4$-alkylsulphoximino, $C_1$-$C_4$-alkylsulphoximino-$C_1$-$C_4$-alkyl, $C_1$-$C_4$-alkylsulphoximino-$C_2$-$C_5$-alkylcarbonyl, $C_2$-$C_6$-alkoxycarbonyl, $C_2$-$C_6$-alkylcarbonyl and $C_3$-$C_6$-trialkylsilyl.

$R^3$ is more preferably hydrogen or in each case optionally singly or multiply, identically or differently substituted $C_1$-$C_6$-alkyl, $C_1$-$C_6$-alkoxy, where the substituents may each independently be selected from halogen, cyano, nitro, hydroxyl, $C_1$-$C_6$-alkyl, $C_3$-$C_6$-cycloalkyl, $C_1$-$C_4$-alkoxy, $C_1$-$C_4$-haloalkoxy, $C_1$-$C_4$-alkylthio, $C_1$-$C_4$-alkylsulphinyl, $C_1$-$C_4$-alkylsulphonyl, $C_1$-$C_4$-alkylsulphimino, $C_1$-$C_4$-alkylsulphimino-$C_1$-$C_4$-alkyl, $C_1$-$C_4$-alkylsulphimino-$C_2$-$C_5$-alkylcarbonyl, $C_1$-$C_4$-alkylsulphoximino, $C_1$-$C_4$-alkylsulphoximino-$C_1$-$C_4$-alkyl, $C_1$-$C_4$-alkylsulphoximino-$C_2$-$C_5$-alkylcarbonyl, $C_2$-$C_6$-alkoxycarbonyl, $C_2$-$C_6$-alkylcarbonyl and $C_3$-$C_6$-trialkylsilyl.

$R^3$ is also more preferably optionally singly or multiply, identically or differently substituted $C_3$-$C_6$-cycloalkyl where the substituents may each independently be selected from halogen, cyano, nitro, hydroxyl, $C_1$-$C_6$-alkyl, $C_3$-$C_6$-cycloalkyl, $C_1$-$C_4$-alkoxy, $C_1$-$C_4$-haloalkoxy, $C_1$-$C_4$-alkylthio, $C_1$-$C_4$-alkylsulphinyl, $C_1$-$C_4$-alkylsulphonyl, $C_1$-$C_4$-alkylsulphimino, $C_1$-$C_4$-alkylsulphimino-$C_1$-$C_4$-alkyl, $C_1$-$C_4$-alkylsulphimino-$C_2$-$C_5$-alkylcarbonyl, $C_1$-$C_4$-alkylsulphoximino, $C_1$-$C_4$-alkylsulphoximino-$C_1$-$C_4$-alkyl, $C_1$-$C_4$-alkylsulphoximino-$C_2$-$C_5$-alkylcarbonyl, $C_2$-$C_6$-alkoxycarbonyl, $C_2$-$C_6$-alkylcarbonyl and $C_3$-$C_6$-trialkylsilyl.

$R^3$ is even more preferably $C_1$-$C_4$-alkyl (methyl, ethyl, n-propyl, isopropyl, n-butyl, isobutyl, sec-butyl or tert-butyl) or cyano-$C_1$-$C_3$-alkyl (cyanomethyl, 1-cyanoethyl, 2-cyanoethyl, 1-cyano-n-propyl, 2-cyano-n-propyl, 3-cyano-n-propyl, 1-cyanoisopropyl, 2-cyanoisopropyl).

$R^3$ is especially preferably methyl, isopropyl or cyanomethyl.

Y is preferably and more preferably O or S.

Y is even more preferably O.

Y is likewise even more preferably S.

$R^4$ is preferably hydroxyl, amino, carboxyl, OCN, SCN, $C_1$-$C_4$-alkoxy-$C_1$-$C_4$-alkyl, $C_1$-$C_4$-alkylthio-$C_1$-$C_4$-alkyl, $C_1$-$C_4$-alkylsulphonyloxy, $C_1$-$C_4$-alkylcarbonylamino, N-methoxy-N-methylamino, hydroxyimino, ($C_1$-$C_4$-alkyl)hydroxyimino, $C_1$-$C_4$-alkoxycarbonyl, $C_1$-$C_4$-alkoxycarbonyl-$C_1$-$C_4$-alkyl, $C_1$-$C_4$-alkylcarbonyl, hydroxy-$C_1$-$C_4$-alkyl, $C_1$-$C_4$-haloalkylcarbonyl, $C_1$-$C_4$-alkylcarbonyloxy, aminocarbonyl, $C_1$-$C_4$-alkylaminocarbonyl, $C_1$-$C_4$-dialkylaminocarbonyl, aminothiocarbonyl, $C_1$-$C_4$-alkylaminothiocarbonyl, $C_1$-$C_4$-dialkylaminothiocarbonyl, $C_1$-$C_4$-alkylsulphonylamino, aminosulphonyl, $C_1$-$C_4$-alkylaminosulphonyl, $C_1$-$C_4$-dialkylaminosulphonyl, $C_1$-$C_4$-alkylsulphoximino or a 3- to 6-membered saturated, partly saturated or aromatic ring which may optionally contain one to three heteroatoms from the group of O, S and N and which is optionally mono- or polysubstituted identically or differently by halogen, cyano, nitro, hydroxyl, amino, carboxyl, $C_1$-$C_4$-alkyl, $C_1$-$C_4$-haloalkyl, $C_2$-$C_6$-alkenyl, $C_2$-$C_6$-haloalkenyl, $C_2$-$C_6$-alkynyl, $C_1$-$C_2$-alkoxy, $C_1$-$C_2$-haloalkoxy, $C_1$-$C_2$-alkylthio, $C_1$-$C_2$-alkylsulphinyl, $C_1$-$C_2$-alkylsulphonyl, $C_1$-$C_2$-alkylsulphonyloxy, $C_1$-$C_2$-haloalkylthio, $C_1$-$C_2$-haloalkylsulphinyl, $C_1$-$C_2$-haloalkylsulphonyl, $C_1$-$C_2$-alkylamino, di-($C_1$-$C_2$-alkyl)amino, $C_1$-$C_2$-alkylcarbonylamino, $C_1$-$C_2$-alkoxycarbonyl, $C_1$-$C_2$-alkylcarbonyl, $C_1$-$C_2$-alkylcarbonyloxy, aminocarbonyl, $C_1$-$C_2$-alkylaminocarbonyl, $C_1$-$C_2$-dialkylaminocarbonyl, aminothiocarbonyl, $C_1$-$C_2$-alkylaminothiocarbonyl, $C_1$-$C_2$-dialkylaminothiocarbonyl, $C_3$-$C_6$-cycloalkylamino, $C_1$-$C_4$-alkylsulphonylamino, aminosulphonyl, $C_1$-$C_4$-alkylaminosulphonyl or $C_1$-$C_4$-dialkylaminosulphonyl.

$R^4$ is more preferably hydroxyl, amino, carboxyl, $C_1$-$C_2$-alkoxy-$C_1$-$C_2$-alkyl, $C_1$-$C_2$-alkylthio-$C_1$-$C_2$-alkyl, $C_1$-$C_2$-alkylsulphonyloxy, $C_1$-$C_2$-alkylcarbonylamino, hydroxyimino, ($C_1$-$C_3$-alkyl)hydroxyimino, $C_1$-$C_4$-alkoxycarbonyl, $C_1$-$C_2$-alkylcarbonyl, hydroxy-$C_1$-$C_2$-alkyl, $C_1$-$C_2$-haloalkylcarbonyl, aminocarbonyl, $C_1$-$C_2$-alkylaminocarbonyl, $C_1$-$C_2$-dialkylaminocarbonyl, aminothiocarbonyl, $C_1$-$C_2$-alkylaminothiocarbonyl, $C_1$-$C_2$-dialkylaminothiocarbonyl, $C_1$-$C_2$-alkylsulphonylamino, aminosulphonyl, $C_1$-$C_2$-alkylaminosulphonyl, $C_1$-$C_2$-dialkylaminosulphonyl, $C_1$-$C_2$-alkylsulphoximino or a 3- to 6-membered saturated, partly saturated or aromatic ring which may optionally contain one to three heteroatoms from the group of O, S and N and which is optionally mono- or polysubstituted identically or differently by halogen, cyano, $C_1$-$C_2$-alkyl, $C_1$-$C_2$-haloalkyl, $C_1$-$C_2$-alkoxy, $C_1$-$C_2$-haloalkoxy, $C_1$-$C_2$-alkylthio, $C_1$-$C_2$-alkylsulphinyl, $C_1$-$C_2$-alkylsulphonyl, $C_1$-$C_2$-haloalkylthio, $C_1$-$C_2$-haloalkylsulphinyl or $C_1$-$C_2$-haloalkylsulphonyl.

$R^4$ is even more preferably hydroxyl, amino, carboxyl, methoxymethyl, methylthiomethyl, methylsulphonyloxy, methylcarbonylamino, hydroxyimino, hydroxyiminomethyl, hydroxyiminoethyl, methoxycarbonyl, ethoxycarbonyl, acetyl, trifluoroacetyl, hydroxyethyl, aminocarbonyl, methylaminocarbonyl, dimethylaminocarbonyl, aminothiocarbonyl, methylaminothiocarbonyl, dimethylaminothiocarbonyl, methylsulphonylamino, aminosulphonyl, methylaminosulphonyl, dimethylaminosulphonyl, methylsulphoximino, cyclopropylmethyloxycarbonyl, cyclobutylmethyloxycarbonyl, cyclobutyloxycarbonyl, 1,3-dioxane, dimethyl-1,3-dioxane, 1,3-dioxolane, trifluoromethylpyrazole, triazole, or cyclopropyl, cyclobutyl, phenyl, furan, thiophene, imidazole, thiazole, oxazole, pyridine, pyrimidine, azetidine, oxetane, thietane, pyrrolidine, pyrazolidine, imidazolidine, piperidine, piperazine, pyrrolidone, imidazolidone, triazolinone, tetrazolinone, thiazolone or oxazolone, which is optionally substituted by fluorine, chlorine, bromine, cyano, methyl, ethyl, trifluoromethyl, methoxy or trifluoromethoxy.

$R^4$ is especially preferably carboxyl, methoxymethyl, methylsulphonyloxy, methoxycarbonyl, hydroxyimino, hydroxyiminomethyl, hydroxyiminoethyl, acetyl, trifluoroacetyl, hydroxyethyl, aminocarbonyl, methylaminocarbonyl, dimethylaminocarbonyl, aminothiocarbonyl, methylaminothiocarbonyl, dimethylaminothiocarbonyl, cyclopropylmethyloxycarbonyl, cyclobutylmethyloxycarbonyl, cyclobutyloxycarbonyl, 1,3-dioxane, dimethyl-1,3-dioxane, 1,3-dioxolane, trifluoromethylpyrazole or triazole.

$R^4$ additionally has the following preferred, more preferred, even more preferred and especially preferred definitions if Y is S:

$R^4$ is additionally preferably hydrogen, $C_1$-$C_4$-alkyl, $C_1$-$C_4$-haloalkyl, halogen, cyano, $C_1$-$C_4$-alkoxy, $C_1$-$C_4$-haloalkoxy, $C_1$-$C_4$-alkylthio or $C_1$-$C_4$-haloalkylthio.

Preferably, two adjacent $R^4$ radicals are also additionally $-(CH_2)_3-$, $-(CH_2)_4-$, $-(CH_2)_5-$, $-(CH{=}CH-)_2-$, $-OCH_2O-$, $-O(CH_2)_2O-$, $-OCF_2O-$, $-(CF_2)_2O-$, $-O(CF_2)_2O-$, $-(CH{=}CH-CH{=}N)-$ or $-(CH{=}CH-N{=}CH)-$.

$R^4$ is additionally more preferably hydrogen, $C_1$-$C_4$-alkyl, $C_1$-$C_2$-haloalkyl, halogen, cyano or $C_1$-$C_2$-haloalkoxy.

More preferably, two adjacent $R^4$ radicals are also additionally $-(CH_2)_4-$, $-(CH{=}CH-)_2-$, $-O(CH_2)_2O-$, $-O(CF_2)_2O-$, $-(CH{=}CH-CH{=}N)-$ or $-(CH{=}CH-N{=}CH)-$.

$R^4$ is additionally even more preferably hydrogen, methyl, trifluoromethyl, cyano, fluorine, chlorine, bromine, iodine or trifluoromethoxy. Even more preferably, two adjacent $R^4$ radicals are also additionally $-(CH_2)_4-$ or $-(CH{=}CH-)_2-$.

$R^4$ is additionally especially preferably chlorine or bromine, $R^4$ is additionally also especially preferably iodine or cyano. Especially preferably, two adjacent $R^4$ radicals are also additionally $-(CH{=}CH-)_2-$.

$R^5$ is preferably $C_1$-$C_4$-alkyl, $C_3$-$C_6$-cycloalkyl, $C_1$-$C_4$-haloalkyl, $C_1$-$C_6$-halocycloalkyl, $C_2$-$C_6$-alkenyl, $C_2$-$C_4$-haloalkenyl, $C_2$-$C_4$-alkynyl, $C_2$-$C_4$-haloalkynyl, $C_1$-$C_4$-alkoxy, $C_1$-$C_4$-haloalkoxy, $C_1$-$C_4$-alkylthio, $C_1$-$C_4$-alkylsulphinyl, $C_1$-$C_4$-alkylsulphonyl, $C_1$-$C_4$-haloalkylthio, $C_1$-$C_4$-haloalkylsulphinyl, $C_1$-$C_4$-haloalkylsulphonyl, halogen, cyano, nitro or $C_3$-$C_6$-trialkylsilyl.

$R^5$ is more preferably $C_1$-$C_4$-alkyl, $C_3$-$C_6$-cycloalkyl, $C_1$-$C_4$-haloalkyl, $C_1$-$C_6$-halocycloalkyl, $C_2$-$C_6$-alkenyl, $C_2$-$C_4$-haloalkenyl, $C_2$-$C_4$-alkynyl, $C_2$-$C_4$-haloalkynyl, $C_1$-$C_4$-alkoxy, $C_1$-$C_4$-haloalkoxy, fluorine, chlorine, bromine, iodine, cyano, nitro or $C_3$-$C_6$-trialkylsilyl.

$R^5$ is even more preferably methyl, fluorine, chlorine, bromine or iodine.

$R^5$ is especially preferably methyl or chlorine.

$R^6$ is preferably $C_1$-$C_6$-alkyl or

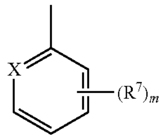

$R^6$ is also preferably $C_3$-$C_6$-cycloalkoxy, $R^6$ is more preferably methyl or

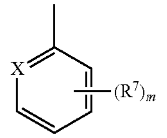

$R^7$ is independently preferably hydrogen, halogen, cyano, $C_1$-$C_4$-alkyl, $C_1$-$C_4$-alkoxy, $C_1$-$C_4$-haloalkyl, $C_1$-$C_4$-haloalkoxy, $C_1$-$C_4$-haloalkylsulphonyl or ($C_1$-$C_4$-alkyl)$C_1$-$C_4$-alkoxyimino, $R^7$ is independently more preferably hydrogen, halogen or $C_1$-$C_4$-haloalkyl, $R^7$ is even more preferably fluorine, chlorine or bromine, $R^7$ is especially preferably chlorine.

m is preferably 1, 2 or 3, m is more preferably 1 or 2, m is even more preferably 1, X is preferably N, CH, CF, CCl, CBr or CI, X is more preferably N, CH, CF, CCl or CBr, X is even more preferably N, CCl or CH.

A is preferably $-CH_2-$, $-CH_2O-$, $-CH_2OCH_2-$, $-CH_2S-$, $-CH_2SCH_2-$, $-CH_2N(C_1$-$C_6$-alkyl)-, $-CH_2N(C_1$-$C_6$-alkyl)$CH_2-$, $-CH(CN)-$, $-CH(C_1$-$C_6$-alkyl)-, $-C$(di-$C_1$-$C_6$-alkyl)-, $-CH_2CH_2-$, $-C{=}NO(C_1$-$C_6$-alkyl)-, A is more preferably $-CH_2-$, $-CH(CH_3)$, $C(CH_3)_2$ or $CH_2CH_2$, A is also more preferably $-CH(CN)-$, A is even more preferably $CH_2$ or $CH(CH_3)$, A is especially preferably $CH_2$, Q is preferably an optionally mono- or polysubstituted 5- or 6-membered aromatic heterocyclic ring from the group of Q-1 to Q-53 or an aromatic 9-membered fused heterobicyclic ring system Q-54 to Q-56, where the substituents may each independently be selected from $C_1$-$C_3$-alkyl, $C_1$-$C_3$-haloalkyl, $C_1$-$C_2$-alkoxy, halogen, cyano, hydroxyl, nitro and $C_1$-$C_2$-haloalkoxy, Q is also preferably an optionally mono- or polysubstituted 5- or 6-membered aromatic heterocyclic ring from the group of Q-1 to Q-53 and Q-58 to Q-59, an aromatic 9-membered fused heterobicyclic ring system Q-54 to Q-56 and a 5-membered heterocyclic ring Q-60 to Q-61, where the substituents may each independently be selected from $C_1$-$C_3$-alkyl, $C_1$-$C_3$-haloalkyl, $C_1$-$C_2$-alkoxy, halogen, cyano, hydroxyl, nitro and $C_1$-$C_2$-haloalkoxy, or where the substituents may each independently be selected from phenyl and a 5- or 6-membered heteroaromatic ring, where phenyl or the ring may optionally be mono- or polysubstituted identically or differently by $C_1$-$C_6$-alkyl, $C_2$-$C_6$-alkenyl, $C_2$-$C_6$-alkynyl, $C_3$-$C_6$-cycloalkyl, $C_1$-$C_6$-haloalkyl, $C_2$-$C_6$-haloalkenyl, $C_2$-$C_6$-haloalkynyl, $C_3$-$C_6$-halocycloalkyl, halogen, CN, $NO_2$, OH, $C_1$-$C_4$-alkoxy, $C_1$-$C_4$-haloalkoxy.

Q is more preferably an optionally mono- or polysubstituted 5- or 6-membered aromatic heterocyclic ring from the group of Q-36 to Q-40 or an aromatic 9-membered fused heterobicyclic ring system Q-54 to Q-56, where the substituents may each independently be selected from $C_1$-$C_3$-alkyl, $C_1$-$C_3$-haloalkyl, $C_1$-$C_2$-alkoxy, halogen, cyano, hydroxyl, nitro and $C_1$-$C_2$-haloalkoxy.

Q is also more preferably an optionally mono- or polysubstituted 5- or 6-membered aromatic heterocyclic ring from the group of Q-36 to Q-40 and Q-58 to Q-59, an aromatic 9-membered fused heterobicyclic ring system Q-54 to Q-56 and a 5-membered heterocyclic ring Q-60 to Q-61, where the substituents may each independently be selected from $C_1$-$C_3$-alkyl, $C_1$-$C_3$-haloalkyl, $C_1$-$C_2$-alkoxy, halogen, cyano, hydroxyl, nitro and $C_1$-$C_2$-haloalkoxy, or where the substituents may each independently be selected from phenyl and a 5- or 6-membered heteroaromatic ring, where phenyl or the ring may optionally be mono- or polysubstituted identically or differently by $C_1$-$C_6$-alkyl, $C_2$-$C_6$-alkenyl, $C_2$-$C_6$-alkynyl, $C_3$-$C_6$-cycloalkyl, $C_1$-$C_6$-haloalkyl, $C_2$-$C_6$-haloalkenyl, $C_2$-$C_6$-haloalkynyl, $C_3$-$C_6$-halocycloalkyl, halogen, CN, $NO_2$, $C_1$-$C_4$-alkoxy, $C_1$-$C_4$-haloalkoxy.

Q is even more preferably an optionally mono- or polysubstituted aromatic heterocyclic ring from the group of Q-37, Q-38, Q-39, Q-40, Q-58 and Q-59, and a 5-membered heterocyclic ring Q-60, where the substituents may each independently be selected from $C_1$-$C_3$-alkyl, $C_1$-$C_3$-haloalkyl, $C_1$-$C_2$-alkoxy, halogen, cyano, hydroxyl, nitro and $C_1$-$C_2$-haloalkoxy, or where the substituents may each independently be selected from phenyl and a 5- or 6-membered heteroaromatic ring, where phenyl or the ring may optionally be mono- or polysubstituted identically or differently by $C_1$-$C_6$-alkyl, $C_2$-$C_6$-alkenyl, $C_2$-$C_6$-alkynyl, $C_3$-$C_6$-cycloalkyl, $C_1$-$C_6$-haloalkyl, $C_2$-$C_6$-haloalkenyl, $C_2$-$C_6$-haloalkynyl, $C_3$-$C_6$-halocycloalkyl, halogen, CN, $NO_2$, $C_1$-$C_4$-alkoxy, $C_1$-$C_4$-haloalkoxy.

Q is also even more preferably an optionally mono- or polysubstituted aromatic heterocyclic ring from the group of Q-37, Q-38, Q-39, Q-40, Q-58 and Q-59, and a 5-membered heterocyclic ring Q-60, where the substituents may each independently be selected from $C_1$-$C_3$-alkyl, $C_1$-$C_3$-haloalkyl, halogen, cyano, nitro or $C_1$-$C_2$-haloalkoxy, or where the substituents may each independently be selected from phenyl and a 5- or 6-membered heteroaromatic ring, where phenyl or the ring may optionally be mono- or polysubstituted identically or differently by $C_1$-$C_6$-alkyl, $C_2$-$C_6$-alkenyl, $C_2$-$C_6$-alkynyl, $C_3$-$C_6$-cycloalkyl, $C_1$-$C_6$-haloalkyl, $C_2$-$C_6$-haloalkenyl, $C_2$-$C_6$-haloalkynyl, $C_3$-$C_6$-halocycloalkyl, halogen, CN, $NO_2$, $C_1$-$C_4$-alkoxy, $C_1$-$C_4$-haloalkoxy, Q is especially preferably an aromatic heterocyclic ring Q-37, Q-40, Q-58 and Q-59 optionally mono-, di- or trisubstituted on carbon atoms, and a 5-membered heterocyclic ring Q-60, where the substituents may each independently be selected from chlorine, fluorine, iodine, bromine, cyano, trifluoromethyl and pentafluoroethyl, or where the substituents may each independently be selected from phenyl, where the phenyl ring may optionally be mono- or polysubstituted identically or differently by $C_1$-$C_6$-alkyl, $C_2$-$C_6$-alkenyl, $C_2$-$C_6$-alkynyl, $C_3$-$C_6$-cycloalkyl, $C_1$-$C_6$-haloalkyl, $C_2$-$C_6$-haloalkenyl, $C_2$-$C_6$-haloalkynyl, $C_3$-$C_6$-halocycloalkyl, halogen, CN, $NO_2$, $C_1$-$C_4$-haloalkoxy, Q is also especially preferably an optionally mono- or polysubstituted aromatic heterocyclic ring from the group of Q-37, Q-40, Q-58 and Q-59, and a 5-membered heterocyclic ring Q-60, where the substituents may each independently be selected from chlorine, fluorine, iodine, cyano, trifluoromethyl and pentafluoroethyl, or where the substituents may each independently be selected from phenyl, where the phenyl ring may optionally be mono- or polysubstituted identically or differently by chlorine, fluorine, iodine, bromine, cyano, trifluoromethyl and pentafluoroethyl.

Q-1

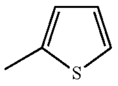

Q-2

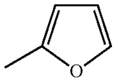

Q-3

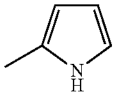

Q-4

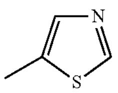

Q-5

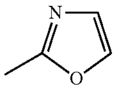

Q-6

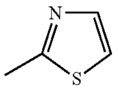

Q-7

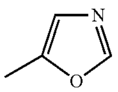

-continued
Q-8
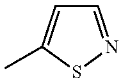
Q-9
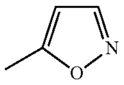
Q-10
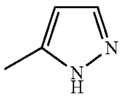
Q-11
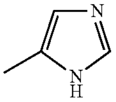
Q-12
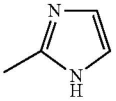
Q-13
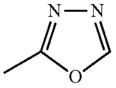
Q-14
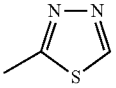
Q-15
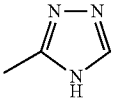
Q-16
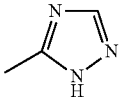
Q-17
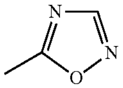
Q-18
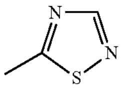
Q-19
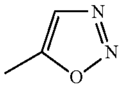
Q-20
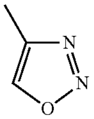
Q-21
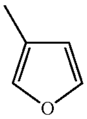
-continued
Q-22
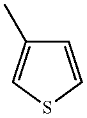
Q-23
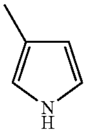
Q-24
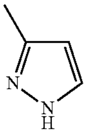
Q-25
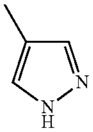
Q-26
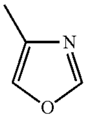
Q-27
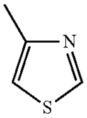
Q-28
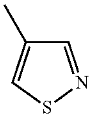
Q-29
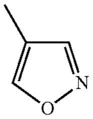
Q-30
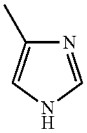
Q-31
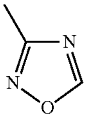
Q-32
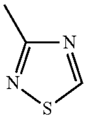
Q-33
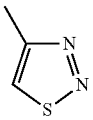

-continued
Q-34
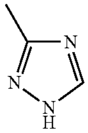
Q-35
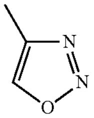
Q-36
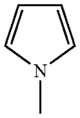
Q-37
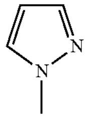
Q-38
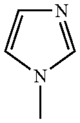
Q-39
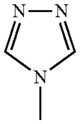
Q-40
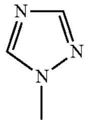
Q-41
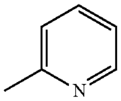
Q-42
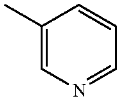
Q-43
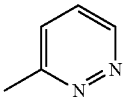
Q-44
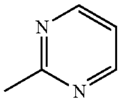
Q-45
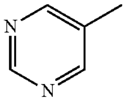
-continued
Q-46
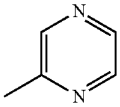
Q-47
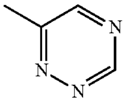
Q-48
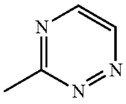
Q-49
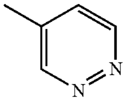
Q-50
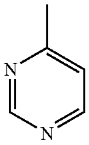
Q-51
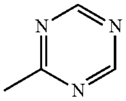
Q-52
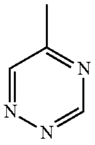
Q-53
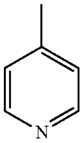
Q-54
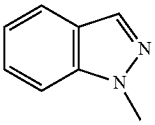
Q-55
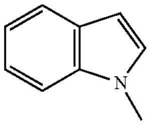
Q-56
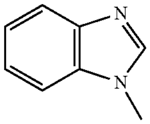
Q-57
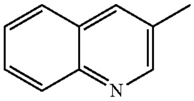

-continued

Q-58

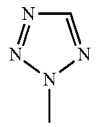

Q-59

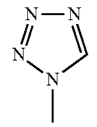

Q-60

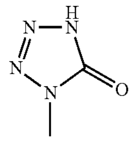

Q-61

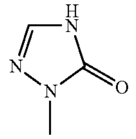

The rings or ring systems listed above may optionally independently be additionally substituted by oxo, thio, (=O)=NH, (=O)=N—CN, $(=O)_2$. Examples include tetrahydrothiophene dioxide, imidazolidone. The ring or ring system Q is preferably additionally substituted by (=O) or $(=O)_2$.

The oxo group as a substituent on a ring carbon atom is then, for example, a carbonyl group in the heterocyclic ring. As a result, lactones and lactams are preferably also included. The oxo group may also occur on the ring heteroatoms, which may exist in different oxidation states, for example in the case of N and S, and in that case form, for example, the divalent —N(O)—, —S(O)— (also SO for short) and $—S(O)_2—$(also $SO_2$ for short) groups in the heterocyclic ring. In the case of —N(O)— and —S(O)— groups, both enantiomers in each case are included.

Substituents other than the oxo group may also be bonded to a heteroatom on a heterocyclic ring, for example to a nitrogen atom when a hydrogen atom on the nitrogen atom of the base skeleton is replaced. In the case of the nitrogen atom and also of other heteroatoms, for example of the sulphur atom, further substitution to form quaternary ammonium compounds or sulphonium compounds is also a possibility.

The abovementioned general or preferred radical definitions or illustrations can be combined with one another as desired, i.e. including combinations between the respective ranges and preferred ranges. They apply both to the end products and correspondingly to precursors and intermediates.

Preference is given in accordance with the invention to the compounds of the formula (I) in which a combination of the definitions listed above as preferred (preferably) is present.

Particular preference is given in accordance with the invention to the compounds of the formula (I) in which a combination of the definitions listed above as more preferred is present.

Very particular preference is given in accordance with the invention to the compounds of the formula (I) in which a combination of the definitions listed above as even more preferred is present.

The compounds of the formula (I) may especially be present in the form of different regioisomers: for example in the form of mixtures of compounds with the definition Q62 or Q63, or in the form of mixtures of Q58 and Q59. Also included in the invention are therefore also mixtures of compounds of the formula (I) where Q is defined as Q62 and Q63, or else Q58 and Q59, and the compounds may be present in different mixing ratios. Preference is given to mixing ratios of compounds of the formula (I) in which the Q radical is Q62 or Q58 to compounds of the formula (I) in which the Q radical is Q63 or Q59 of 60:40 to 99:1, more preferably of 70:30 to 97:3, even more preferably of 80:20 to 95:5. Especially preferred are the following mixing ratios of a compound of the formula (I) where Q is defined as Q62 or Q58 to the compound of the formula (I) where Q is defined as Q63 or Q59:80:20; 81:19; 82:18; 83:17; 84:16; 85:15, 86:14; 87:13; 88:12; 89:11; 90:10, 91:9; 92:8; 93:7; 96:6; 95:5.

Preparation Processes

It has additionally been found that anthranilamides of the formula (I) are obtained by one of the processes which follow.

Anthranilamides of the formula (I)

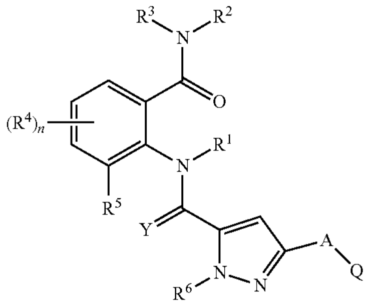

(I)

in which A, $R^1$, $R^2$, $R^3$, $R^4$, $R^5$, $R^6$, Q and n are each as defined above and Y is O are obtained by reacting (A) anilines of the formula (II)

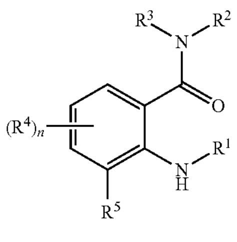

(II)

in which A, $R^1$, $R^2$, $R^3$, $R^4$, $R^5$ and n are each as defined above, with carbonyl chlorides of the formula (III)

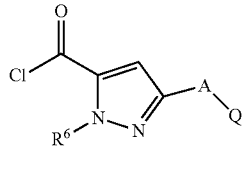

(III)

in which $R^6$, A and Q are each as defined above, in the presence of an acid binder, (B) anilines of the formula (II)

(II)

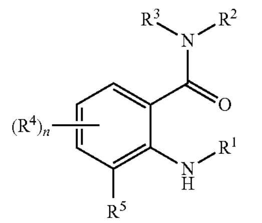

in which A, $R^1$, $R^2$, $R^3$, $R^4$, $R^5$ and n are each as defined above, with a carboxylic acid of the formula (IV)

(IV)

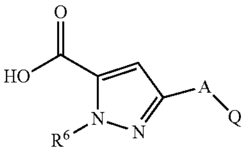

in which $R^6$, A and Q are each as defined above, in the presence of a condensing agent, or by (C) synthesizing anthranilamides of the formula (I) in which $R^1$ is hydrogen by reacting benzoxazinones of the formula (V)

(V)

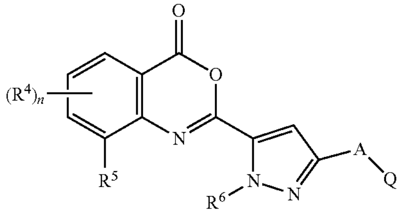

in which $R^4$, $R^5$, $R^6$, A, Q and n are each as defined above, with an amine of the formula (XV)

(XV)

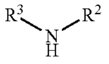

in which $R^2$ and $R^3$ are each as defined above, in the presence of a diluent.

Anilines of the formula B are novel. They can be obtained according to the reaction scheme which follows, in which $R^2$, $R^3$ and $R^5$ are each as defined above, from compounds of the formula A. Compounds of the formula A are known (e.g. WO 2009061991). The conversion of A to B can be performed by known methods, for example with carbon monoxide in an autoclave in the presence of a suitable catalyst, for example bis(triphenylphosphine)palladium dichloride in methanol (e.g. Bioorganic & Medicinal Chemistry Letters, 16(1), 44-48; 2006).

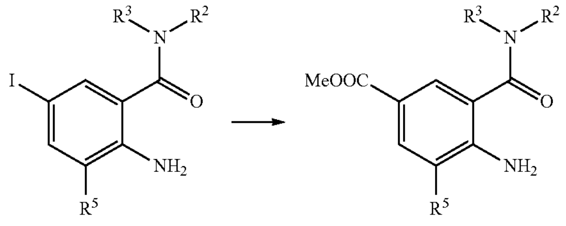

A B

Anilines of the formulae D, E and F are novel. They can be obtained according to the reaction scheme which follows, in which $R^2$, $R^3$ and $R^5$ are each as defined above, from compounds of the formula C. Compounds of the formula C are known (e.g. WO 2009061991). The conversion of C to D can be performed by known methods, for example with (1-ethoxyvinyl)tributylstannane under palladium catalysis (e.g. J. Med. Chem. 41, 1998, 3736). The further conversion to E is effected with a suitable reducing agent, for example sodium borohydride (e.g. WO 2006108591). The conversion of D to F is effected by known methods with hydroxylamine hydrochloride and sodium acetate (e.g. Tetrahedron Letters, 51(7), 1030-1033; 2010).

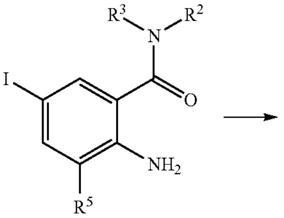

C

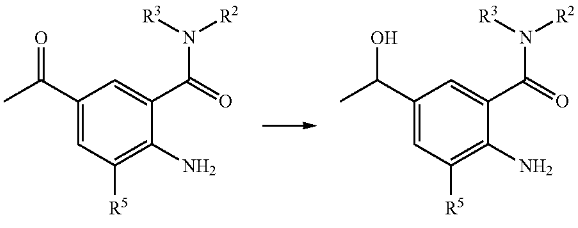

D E

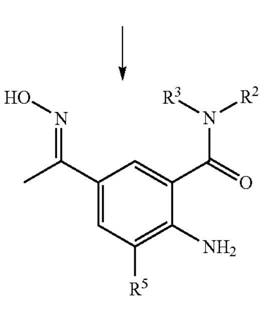

F

The inventive active ingredients, given good plant tolerance, favourable homeotherm toxicity and good environmental compatibility, are suitable for protecting plants and plant organs, for increasing harvest yields, for improving the quality of the harvested material and for controlling animal pests, especially insects, arachnids, helminths, nematodes and molluscs, which are encountered in agriculture, in horticulture, in animal husbandry, in forests, in gardens and leisure facilities, in the protection of stored products and of materials, and in the hygiene sector. They can preferably be used as crop protection compositions. They are active against normally sensitive and resistant species and against all or some stages of development. The abovementioned pests include:

pests from the phylum of: Arthropoda, especially from the class of the Arachnida, for example, *Acarus* spp., *Aceria sheldoni, Aculops* spp., *Aculus* spp., *Amblyomma* spp., *Amphitetranychus viennensis, Argas* spp., *Boophilus* spp., *Brevipalpus* spp., *Bryobia praetiosa, Centruroides* spp., *Chorioptes* spp., *Dermanyssus gallinae, Dermatophagoides pteronyssius, Dermatophagoides farinae, Dermacentor* spp., *Eotetranychus* spp., *Epitrimerus pyri, Eutetranychus* spp., *Eriophyes* spp., *Halotydeus destructor, Hemitarsonemus* spp., *Hyalomma* spp., *Ixodes* spp., *Latrodectus* spp., *Loxosceles* spp., *Metatetranychus* spp., *Nuphersa* spp., *Oligonychus* spp., *Ornithodorus* spp., *Ornithonyssus* spp., *Panonychus* spp., *Phyllocoptruta oleivora, Polyphagotarsonemus latus, Psoroptes* spp., *Rhipicephalus* spp., *Rhizoglyphus* spp., *Sarcoptes* spp., *Scorpio maurus, Stenotarsonemus* spp., *Tarsonemus* spp., *Tetranychus* spp., *Vaejovis* spp., *Vasates lycopersici.*

From the order of the Anoplura (Phthiraptera), for example, *Damalinia* spp., *Haematopinus* spp., *Linognathus* spp., *Pediculus* spp., *Ptirus pubis, Trichodectes* spp.

From the order of the Chilopoda, for example, *Geophilus* spp., *Scutigera* spp.

From the order of the Coleoptera, for example, *Acalymma vittatum, Acanthoscelides obtectus, Adoretus* spp., *Agelastica alni, Agriotes* spp., *Alphitobius diaperinus, Amphimallon solstitialis, Anobium punctatum, Anoplophora* spp., *Anthonomus* spp., *Anthrenus* spp., *Apion* spp., *Apogonia* spp., *Atomaria* spp., *Attagenus* spp., *Bruchidius obtectus, Bruchus* spp., *Cassida* spp., *Cerotoma trifurcata, Ceutorrhynchus* spp., *Chaetocnema* spp., *Cleonus mendicus, Conoderus* spp., *Cosmopolites* spp., *Costelytra zealandica, Ctenicera* spp., *Curculio* spp., *Cryptorhynchus lapathi, Cylindrocopturus* spp., *Dermestes* spp., *Diabrotica* spp., *Dichocrocis* spp., *Diloboderus* spp., *Epilachna* spp., *Epitrix* spp., *Faustinus* spp., *Gibbium psylloides, Hellula undalis, Heteronychus arator, Heteronyx* spp., *Hylamorpha elegans, Hylotrupes bajulus, Hypera postica, Hypothenemus* spp., *Lachnosterna consanguinea, Lema* spp., *Leptinotarsa decemlineata, Leucoptera* spp., *Lissorhoptrus oryzophilus, Lixus* spp., *Luperodes* spp., *Lyctus* spp., *Megascelis* spp., *Melanotus* spp., *Meligethes aeneus, Melolontha* spp., *Migdolus* spp., *Monochamus* spp., *Naupactus xanthographus, Niptus hololeucus, Oryctes rhinoceros, Oryzaephilus surinamensis, Oryzaphagus oryzae, Otiorrhynchus* spp., *Oxycetonia jucunda, Phaedon cochleariae, Phyllophaga* spp., *Phyllotreta* spp., *Popillia japonica, Premnotrypes* spp., *Prostephanus truncatus, Psylliodes* spp., *Ptinus* spp., *Rhizobius ventralis, Rhizopertha dominica, Sitophilus* spp., *Sphenophorus* spp., *Stegobium paniceum, Sternechus* spp., *Symphyletes* spp., *Tanymecus* spp., *Tenebrio molitor, Tribolium* spp., *Trogoderma* spp., *Tychius* spp., *Xylotrechus* spp., *Zabrus* spp.

From the order of the Collembola, for example, *Onychiurus armatus.*

From the order of the Diplopoda, for example, *Blaniulus guttulatus.*

From the order of the Diptera, for example, *Aedes* spp., *Agromyza* spp., *Anastrepha* spp., *Anopheles* spp., *Asphondylia* spp., *Bactrocera* spp., *Bibio hortulanus, Calliphora erythrocephala, Ceratitis capitata, Chironomus* spp., *Chrysomyia* spp., *Chrysops* spp., *Cochliomyia* spp., *Contarinia* spp., *Cordylobia anthropophaga, Culex* spp., *Culicoides* spp., *Culiseta* spp., *Cuterebra* spp., *Dacus oleae, Dasyneura* spp., *Delia* spp., *Dermatobia hominis, Drosophila* spp., *Echinocnemus* spp., *Fannia* spp., *Gasterophilus* spp., *Glossina* spp., *Haematopota* spp., *Hydrellia* spp., *Hylemyia* spp., *Hyppobosca* spp., *Hypoderma* spp., *Liriomyza* spp., *Lucilia* spp., *Lutzomia* spp., *Mansonia* spp., *Musca* spp., *Nezara* spp., *Oestrus* spp., *Oscinella frit, Pegomyia* spp., *Phlebotomus* spp., *Phorbia* spp., *Phormia* spp., *Prodiplosis* spp., *Psila rosae, Rhagoletis* spp., *Sarcophaga* spp., *Simulium* spp, *Stomoxys* spp., *Tabanus* spp., *Tannia* spp., *Tetanops* spp., *Tipula* spp.

From the order of the Heteroptera, for example, *Anasa tristis, Antestiopsis* spp., *Blissus* spp., *Boisea* spp., *Calocoris* spp., *Campylomma livida, Cavelerius* spp., *Cimex* spp., *Collaria* spp., *Creontiades dilutus, Dasynus piperis, Dichelops furcatus, Diconocoris hewetti, Dysdercus* spp., *Euschistus* spp., *Eurygaster* spp., *Heliopeltis* spp., *Horcias nobilellus, Leptocorisa* spp., *Leptoglossus phyllopus, Lygus* spp., *Macropes excavatus, Miridae, Monalonion atratum, Nezara* spp., *Oebalus* spp., *Pentomidae, Piesma quadrata, Piezodorus* spp., *Psallus* spp., *Pseudacysta persea, Rhodnius* spp., *Sahlbergella singularis, Scaptocoris castanea, Scotinophora* spp., *Stephanitis nashi, Tibraca* spp., *Triatoma* spp.

From the order of the Homoptera, for example, *Acyrthosipon* spp., *Acrogonia* spp., *Aeneolamia* spp., *Agonoscena* spp., *Aleurodes* spp., *Aleurolobus barodensis, Aleurothrixus* spp., *Amrasca* spp., *Anuraphis cardui, Aonidiella* spp., *Aphanostigma piri, Aphis* spp., *Arboridia apicalis, Aspidiella* spp., *Aspidiotus* spp., *Atanus* spp., *Aulacorthum solani, Bemisia* spp., *Brachycaudus helichrysii, Brachycolus* spp., *Brevicoryne brassicae, Calligypona marginata, Carneocephala fulgida, Ceratovacuna lanigera, Cercopidae, Ceroplastes* spp., *Chaetosiphon fragaefolii, Chionaspis tegalensis, Chlorita onukii, Chromaphis juglandicola, Chrysomphalus ficus, Cicadulina mbila, Coccomytilus halli, Coccus* spp., *Cryptomyzus ribis, Dalbulus* spp., *Dialeurodes* spp., *Diaphorina* spp., *Diaspis* spp., *Drosicha* spp., *Dysaphis* spp., *Dysmicoccus* spp., *Empoasca* spp., *Eriosoma* spp., *Erythroneura* spp., *Euscelis bilobatus, Ferrisia* spp., *Geococcus coffeae, Hieroglyphus* spp., *Homalodisca coagulata, Hyalopterus arundinis, Icerya* spp., *Idiocerus* spp., *Idioscopus* spp., *Laodelphax striatellus, Lecanium* spp., *Lepidosaphes* spp., *Lipaphis erysimi, Macrosiphum* spp., *Mahanarva* spp., *Melanaphis sacchari, Metcalfiella* spp., *Metopolophium dirhodum, Monellia costalis, Monelliopsis pecanis, Myzus* spp., *Nasonovia ribisnigri, Nephotettix* spp., *Nilaparvata lugens, Oncometopia* spp., *Orthezia praelonga, Parabemisia myricae, Paratrioza* spp., *Parlatoria* spp., *Pemphigus* spp., *Peregrinus maidis, Phenacoccus* spp., *Phloeomyzus passerinii, Phorodon humuli, Phylloxera* spp., *Pinnaspis aspidistrae, Planococcus* spp., *Protopulvinaria pyriformis, Pseudaulacaspis pentagona, Pseudococcus* spp., *Psylla* spp., *Pteromalus* spp., *Pyrilla* spp., *Quadraspidiotus* spp., *Quesada gigas, Rastrococcus* spp., *Rhopalosiphum* spp., *Saissetia* spp., *Scaphoides titanus, Schizaphis graminum, Selenaspidus articulatus, Sogata* spp., *Sogatella furcifera, Sogatodes* spp., *Stictocephala festina, Tenalaphara malayensis, Tinocallis caryaefoliae, Tomaspis* spp., *Toxoptera* spp., *Trialeurodes* spp., *Trioza* spp., *Typhlocyba* spp., *Unaspis* spp., *Viteus vitifolii, Zygina* spp.

From the order of the Hymenoptera, for example, *Acromyrmex* spp., *Athalia* spp., *Atta* spp., *Diprion* spp., *Hoplo-*

*campa* spp., *Lasius* spp., *Monomorium pharaonis, Solenopsis invicta, Tapinoma* spp., *Vespa* spp.

From the order of the Isopoda, for example, *Armadillidium vulgare, Oniscus asellus* and *Porcellio scaber.*

From the order of the Isoptera, for example, *Coptotermes* spp., *Cornitermes cumulans, Cryptotermes* spp., *Incisitermes* spp., *Microtermes obesi, Odontotermes* spp., *Reticulitermes* spp.

From the order of the Lepidoptera, for example, *Acronicta major, Adoxophyes* spp., *Aedia leucomelas, Agrotis* spp., *Alabama* spp., *Amyelois transitella, Anarsia* spp., *Anticarsia* spp., *Argyroploce* spp., *Barathra brassicae, Borbo cinnara, Bucculatrix thurberiella, Bupalus piniarius, Busseola* spp., *Cacoecia* spp., *Caloptilia theivora, Capua reticulana, Carpocapsa pomonella, Carposina niponensis, Chematobia brumata, Chilo* spp., *Choristoneura* spp., *Clysia ambiguella, Cnaphalocerus* spp., *Cnephasia* spp., *Conopomorpha* spp., *Conotrachelus* spp., *Copitarsia* spp., *Cydia* spp., *Dalaca noctuides, Diaphania* spp., *Diatraea saccharalis, Earias* spp., *Ecdytolopha aurantium, Elasmopalpus lignosellus, Eldana saccharina, Ephestia* spp., *Epinotia* spp., *Epiphyas postvittana, Etiella* spp., *Eulia* spp., *Eupoecilia ambiguella, Euproctis* spp., *Euxoa* spp., *Feltia* spp., *Galleria mellonella, Gracillaria* spp., *Grapholitha* spp., *Hedylepta* spp., *Helicoverpa* spp., *Heliothis* spp., *Hofmannophila pseudospretella, Homoeosoma* spp., *Homona* spp., *Hyponomeuta padella, Kakivoria flavofasciata, Laphygma* spp., *Laspeyresia molesta, Leucinodes orbonalis, Leucoptera* spp., *Lithocolletis* spp., *Lithophane antennata, Lobesia* spp., *Loxagrotis albicosta, Lymantria* spp., *Lyonetia* spp., *Malacosoma neustria, Maruca testulalis, Mamestra brassicae, Mocis* spp., *Mythimna separata, Nymphula* spp., *Oiketicus* spp., *Oria* spp., *Orthaga* spp., *Ostrinia* spp., *Oulema oryzae, Panolis flammea, Parnara* spp., *Pectinophora* spp., *Perileucoptera* spp., *Phthorimaea* spp., *Phyllocnistis citrella, Phyllonorycter* spp., *Pieris* spp., *Platynota stultana, Plodia interpunctella, Plusia* spp., *Plutella xylostella, Prays* spp., *Prodenia* spp., *Protoparce* spp., *Pseudaletia* spp., *Pseudoplusia includens, Pyrausta nubilalis, Rachiplusia nu, Schoenobius* spp., *Scirpophaga* spp., *Scotia segetum, Sesamia* spp., *Sparganothis* spp., *Spodoptera* spp., *Stathmopoda* spp., *Stomopteryx subsecivella, Synanthedon* spp., *Tecia solanivora, Thermesia gemmatalis, Tinea pellionella, Tineola bisselliella, Tortrix* spp., *Trichophaga tapetzella, Trichoplusia* spp., *Tuta absoluta, Virachola* spp.

From the order of the Orthoptera, for example, *Acheta domesticus, Blatta orientalis, Blattella germanica, Dichroplus* spp., *Gryllotalpa* spp., *Leucophaea maderae, Locusta* spp., *Melanoplus* spp., *Periplaneta* spp., *Pulex irritans, Schistocerca gregaria, Supella longipalpa.*

From the order of the Siphonaptera, for example, *Ceratophyllus* spp., *Ctenocephalides* spp., *Tunga penetrans, Xenopsylla cheopis.*

From the order of the Symphyla, for example, *Scutigerella* spp.

From the order of the Thysanoptera, for example, *Anaphothrips obscurus, Baliothrips biformis, Drepanothris reuteri, Enneothrips flavens, Frankliniella* spp., *Heliothrips* spp., *Hercinothrips femoralis, Rhipiphorothrips cruentatus, Scirtothrips* spp., *Taeniothrips cardamoni, Thrips* spp.

From the order of the Zygentoma (=Thysanura), for example, *Lepisma saccharina, Thermobia domestica.*

Pests from the phylum of: Mollusca, especially from the class of the Bivalvia, for example *Dreissena* spp.

From the class of the Gastropoda, for example, *Arion* spp., *Biomphalaria* spp., *Bulinus* spp., *Deroceras* spp., *Galba* spp., *Lymnaea* spp., *Oncomelania* spp., *Pomacea* spp., *Succinea* spp.

Animal parasites from the phyla of: Plathelminthes and Nematoda, especially from the class of the helminths, for example, *Ancylostoma duodenale, Ancylostoma ceylanicum, Acylostoma braziliensis, Ancylostoma* spp., *Ascaris* spp., *Brugia malayi, Brugia timori, Bunostomum* spp., *Chabertia* spp., *Clonorchis* spp., *Cooperia* spp., *Dicrocoelium* spp., *Dictyocaulus filaria, Diphyllobothrium latum, Dracunculus medinensis, Echinococcus granulosus, Echinococcus multilocularis, Enterobius vermicularis, Faciola* spp., *Haemonchus* spp., *Heterakis* spp., *Hymenolepis nana, Hyostrongulus* spp., *Loa Loa, Nematodirus* spp., *Oesophagostomum* spp., *Opisthorchis* spp., *Onchocerca volvulus, Ostertagia* spp., *Paragonimus* spp., *Schistosomen* spp., *Strongyloides fuelleborni, Strongyloides stercoralis, Stronyloides* spp., *Taenia saginata, Taenia solium, Trichinella spiralis, Trichinella nativa, Trichinella britovi, Trichinella nelsoni, Trichinella pseudopsiralis, Trichostrongulus* spp., *Trichuris trichuria, Wuchereria bancrofti.*

Plant pests from the phylum of: Nematoda, i.e. phytoparasitic nematodes, especially *Aphelenchoides* spp., *Bursaphelenchus* spp., *Ditylenchus* spp., *Globodera* spp., *Heterodera* spp., *Longidorus* spp., *Meloidogyne* spp., *Pratylenchus* spp., *Radopholus similis, Trichodorus* spp., *Tylenchulus semipenetrans, Xiphinema* spp.

Subphylum: Protozoa

It is also possible to control protozoa, such as Eimeria.

In some cases, the inventive compounds can, at particular concentrations or application rates, also be used as herbicides, safeners, growth regulators or agents to improve plant properties, or as microbicides, for example as fungicides, antimycotics, bactericides, viricides (including compositions against viroids) or as compositions against MLO (Mycoplasma-like organisms) and RLO (Rickettsia-like organisms). If appropriate, they can also be used as intermediates or precursors for the synthesis of other active ingredients.

The present invention further relates to formulations and use forms prepared therefrom as crop protection compositions and/or pesticides, for example drench, drip and spray liquors, comprising at least one of the inventive active ingredient. In some cases, the use forms comprise further crop protection compositions and/or pesticides and/or adjuvants which improve action, such as penetrants, e.g. vegetable oils, for example rapeseed oil, sunflower oil, mineral oils, for example paraffin oils, alkyl esters of vegetable fatty acids, for example rapeseed oil methyl ester or soya oil methyl ester, or alkanol alkoxylates and/or spreaders, for example alkylsiloxanes and/or salts, for example organic or inorganic ammonium or phosphonium salts, for example ammonium sulphate or diammonium hydrogenphosphate and/or retention promoters, for example dioctyl sulphosuccinate or hydroxypropyl guar polymers and/or humectants, for example glycerol and/or fertilizers, for example ammonium-, potassium- or phosphorus-containing fertilizers.

Customary formulations are, for example, water-soluble liquids (SL), emulsion concentrates (EC), emulsions in water (EW), suspension concentrates (SC, SE, FS, OD), water-dispersible granules (WG), granules (GR) and capsule concentrates (CS); these and further possible formulation types are described, for example, by Crop Life International and in Pesticide Specifications, Manual on development and use of FAO and WHO specifications for pesticides, FAO Plant Production and Protection Papers—173, prepared by the FAO/WHO Joint Meeting on Pesticide Specifications, 2004, ISBN: 9251048576. The formulations optionally comprise, in addition to one or more inventive active ingredients, further active agrochemical ingredients.

These are preferably formulations or use forms which comprise auxiliaries, for example extenders, solvents, spontaneity promoters, carriers, emulsifiers, dispersants, frost protectants, biocides, thickeners and/or further auxiliaries, for example adjuvants. An adjuvant in this context is a component which enhances the biological effect of the formulation, without the component itself having a biological effect. Examples of adjuvants are agents which promote retention, spreading, attachment to the leaf surface or penetration.

These formulations are produced in a known manner, for example by mixing the active ingredients with auxiliaries, for example extenders, solvents and/or solid carriers and/or further auxiliaries, for example surfactants. The formulations are produced either in suitable production plants or else before or during application.

The auxiliaries used may be substances suitable for imparting special properties, such as certain physical, technical and/or biological properties, to the formulation of the active ingredient, or to the use forms prepared from these formulations (for example ready-to-use crop protection compositions such as spray liquors or seed dressing products).

Suitable extenders are, for example, water, polar and nonpolar organic chemical liquids, for example from the classes of the aromatic and non-aromatic hydrocarbons (such as paraffins, alkylbenzenes, alkylnaphthalenes, chlorobenzenes), the alcohols and polyols (which, if appropriate, may also be substituted, etherified and/or esterified), the ketones (such as acetone, cyclohexanone), esters (including fats and oils) and (poly)ethers, the unsubstituted and substituted amines, amides, lactams (such as N-alkylpyrrolidones) and lactones, the sulphones and sulphoxides (such as dimethyl sulphoxide).

If the extender utilized is water, it is also possible to use, for example, organic solvents as auxiliary solvents. Useful liquid solvents are essentially: aromatics such as xylene, toluene or alkylnaphthalenes, chlorinated aromatics and chlorinated aliphatic hydrocarbons such as chlorobenzenes, chloroethylenes or methylene chloride, aliphatic hydrocarbons such as cyclohexane or paraffins, for example mineral oil fractions, mineral and vegetable oils, alcohols such as butanol or glycol and their ethers and esters, ketones such as acetone, methyl ethyl ketone, methyl isobutyl ketone or cyclohexanone, strongly polar solvents such as dimethylformamide and dimethyl sulphoxide, and also water.

In principle it is possible to use all suitable solvents. Examples of suitable solvents are aromatic hydrocarbons, such as xylene, toluene or alkylnaphthalenes, chlorinated aromatic or aliphatic hydrocarbons, such as chlorobenzene, chloroethylene or methylene chloride, aliphatic hydrocarbons, such as cyclohexane, paraffins, petroleum fractions, mineral and vegetable oils, alcohols, such as methanol, ethanol, isopropanol, butanol or glycol and their ethers and esters, ketones such as acetone, methyl ethyl ketone, methyl isobutyl ketone or cyclohexanone, strongly polar solvents, such as dimethyl sulphoxide, and also water.

In principle it is possible to use all suitable carriers. Useful carriers include especially: for example ammonium salts and ground natural minerals such as kaolins, clays, talc, chalk, quartz, attapulgite, montmorillonite or diatomaceous earth, and ground synthetic materials such as finely divided silica, alumina and natural or synthetic silicates, resins, waxes and/or solid fertilizers. Mixtures of such carriers can likewise be used. Useful carriers for granules include: for example crushed and fractionated natural rocks such as calcite, marble, pumice, sepiolite, dolomite, and synthetic granules of inorganic and organic meals, and also granules of organic material such as sawdust, paper, coconut shells, maize cobs and tobacco stalks.

Liquefied gaseous extenders or solvents can also be used. Particularly suitable extenders or carriers are those which are gaseous at ambient temperature and under atmospheric pressure, for example aerosol propellant gases, such as halohydrocarbons, and also butane, propane, nitrogen and carbon dioxide.

Examples of emulsifiers and/or foam formers, dispersants or wetting agents with ionic or nonionic properties, or mixtures of these surfactants, are salts of polyacrylic acid, salts of lignosulphonic acid, salts of phenolsulphonic acid or naphthalenesulphonic acid, polycondensates of ethylene oxide with fatty alcohols or with fatty acids or with fatty amines, with substituted phenols (preferably alkylphenols or arylphenols), salts of sulphosuccinic esters, taurine derivatives (preferably alkyl taurates), phosphoric esters of polyethoxylated alcohols or phenols, fatty esters of polyols, and derivatives of the compounds containing sulphates, sulphonates and phosphates, for example alkylaryl polyglycol ethers, alkylsulphonates, alkyl sulphates, arylsulphonates, protein hydrolysates, lignosulphite waste liquors and methylcellulose. The presence of a surfactant is advantageous when one of the active ingredients and/or one of the inert carriers is insoluble in water and when application is effected in water.

Further auxiliaries which may be present in the formulations and the use forms derived therefrom include dyes such as inorganic pigments, for example iron oxide, titanium oxide and Prussian Blue, and organic dyes such as alizarin dyes, azo dyes and metal phthalocyanine dyes, nutrients and trace nutrients such as salts of iron, manganese, boron, copper, cobalt, molybdenum and zinc.

Additional components may be stabilizers, such as cold stabilizers, preservatives, antioxidants, light stabilizers, or other agents which improve chemical and/or physical stability. Foam formers or antifoams may also be present.

Tackifiers such as carboxymethylcellulose and natural and synthetic polymers in the form of powders, granules or latices, such as gum arabic, polyvinyl alcohol and polyvinyl acetate, or else natural phospholipids such as cephalins and lecithins and synthetic phospholipids may also be present as additional auxiliaries in the formulations and the use forms derived therefrom. Further auxiliaries may be mineral and vegetable oils.

If appropriate, the formulations and the use forms derived therefrom may also comprise further auxiliaries. Examples of such additives include fragrances, protective colloids, binders, adhesives, thickeners, thixotropic agents, penetrants, retention promoters, stabilizers, sequestrants, complexing agents, humectants, spreaders. In general, the active ingredients can be combined with any solid or liquid additive commonly used for formulation purposes.

Useful retention promoters include all those substances which reduce the dynamic surface tension, for example dioctyl sulphosuccinate, or increase the viscoelasticity, for example hydroxypropylguar polymers.

Useful penetrants in the present context are all those substances which are typically used to improve the penetration of active agrochemical ingredients into plants. Penetrants are defined in this context by their ability to penetrate from the (generally aqueous) application liquor and/or from the spray coating into the cuticle of the plant and thereby increase the mobility of active ingredients in the cuticle. The method described in the literature (Baur et al., 1997, Pesticide Science 51, 131-152) can be used to determine this property. Examples include alcohol alkoxylates such as coconut fatty ethoxylate (10) or isotridecyl ethoxylate (12), fatty acid esters, for example rapeseed oil methyl ester or soya oil methyl ester, fatty amine alkoxylates, for example tallowamine ethoxylate (15), or ammonium and/or phosphonium salts, for example ammonium sulphate or diammonium hydrogenphosphate.

The formulations contain generally between 0.01 and 98% by weight of active ingredient, preferably between 0.5 and 90%.

The inventive active ingredients may be used as such or in formulations thereof, including in a mixture with one or more suitable fungicides, bactericides, acaricides, nematicides, insecticides, microbicides, fertilizers, attractants, phytotonics, sterilants, synergists, safeners, semiochemicals and/or plant growth regulators, in order thus, for example, to broaden the spectrum of action, to prolong the duration of action, to increase the rate of action, to prevent repulsion or prevent evolution of resistance. In addition, plant growth can be improved by those combinations which enhance tolerance to abiotic factors, for example high or low temperatures, to drought or to elevated water content or soil salinity. It is also possible to improve flowering and fruiting performance, optimize germination capacity and root development, facilitate harvesting and improve yields, influence maturation, improve the quality and/or the nutritional value of the harvested products, prolong storage life and/or improve the processibility of the harvested products. In general, combination of the inventive active ingredients and mixing partners results in synergistic effects, which means that the efficacy of the mixture in question is greater than the efficacy of the individual components. It is generally possible to use the combinations in premixes, tank mixes or ready mixes, and also in seed applications.

Particularly favorable examples of mixing partners are the following compounds:

Insecticides/acaricides/nematicides:

(1) Acetylcholinesterase (AChE) inhibitors, for example carbamates, for example alanycarb, aldicarb, bendiocarb, benfuracarb, butocarboxim, butoxycarboxim, carbaryl, carbofuran, carbosulfan, ethiofencarb, fenobucarb, formetanate, furathiocarb, isoprocarb, methiocarb, methomyl, metolcarb, oxamyl, pirimicarb, propoxur, thiodicarb, thiofanox, triazamate, trimethacarb, XMC and xylylcarb; or organophosphates, for example acephate, azamethiphos, azinphos (-methyl, -ethyl), cadusafos, chlorethoxyfos, chlorfenvinphos, chlormephos, chlorpyrifos (-methyl), coumaphos, cyanophos, demeton-S-methyl, diazinon, dichlorvos/DDVP, dicrotophos, dimethoate, dimethylvinphos, disulfoton, EPN, ethion, ethoprophos, famphur, fenamiphos, fenitrothion, fenthion, fosthiazate, heptenophos, isofenphos, isopropyl O-(methoxyaminothiophosphoryl)salicylate, isoxathion, malathion, mecarbam, methamidophos, methidathion, mevinphos, monocrotophos, naled, omethoate, oxydemeton-methyl, parathion (-methyl), phenthoate, phorate, phosalone, phosmet, phosphamidon, phoxim, pirimiphos (-methyl), profenofos, propetamphos, prothiofos, pyraclofos, pyridaphenthion, quinalphos, sulfotep, tebupirimfos, temephos, terbufos, tetrachlorvinphos, thiometon, triazophos, triclorfon and vamidothion.

(2) GABA-gated chloride channel antagonists, for example organochlorines, for example chlordane and endosulfan (alpha-); or fiproles (phenylpyrazoles), for example ethiprole, fipronil, pyrafluprole and pyriprole.

(3) Sodium channel modulators/voltage-dependent sodium channel blockers, for example pyrethroids, for example acrinathrin, allethrin (d-cis-trans, d-trans), bifenthrin, bioallethrin, bioallethrin-S-cyclopentenyl, bioresmethrin, cycloprothrin, cyfluthrin (beta-), cyhalothrin (gamma-, lambda-), cypermethrin (alpha-, beta-, theta-, zeta-), cyphenothrin [(1R)-trans-isomers], deltamethrin, dimefluthrin, empenthrin [(EZ)-(1R)-isomers], esfenvalerate, etofenprox, fenpropathrin, fenvalerate, flucythrinate, flumethrin, fluvalinate (tau-), halfenprox, imiprothrin, metofluthrin, permethrin, phenothrin [(1R)-trans-isomer], prallethrin, profluthrin, pyrethrins (pyrethrum), resmethrin, RU 15525, silafluofen, tefluthrin, tetramethrin [(1R)-isomers], tralomethrin, transfluthrin and ZXI 8901; or DDT; or methoxychlor.

(4) Nicotinergic acetylcholine receptor agonists, for example neonicotinoids, for example acetamiprid, clothianidin, dinotefuran, imidacloprid, nitenpyram, thiacloprid, thiamethoxam; or nicotine.

(5) Allosteric acetylcholine receptor modulators (agonists), for example spinosyns, for example spinetoram and spinosad.

(6) Chloride channel activators, for example avermectins/milbemycins, for example abamectin, emamectin benzoate, lepimectin and milbemectin.

(7) Juvenile hormone analogues, for example hydroprene, kinoprene, methoprene; or fenoxycarb; pyriproxyfen.

(8) Active ingredients with unknown or nonspecific mechanisms of action, for example fumigants, for example methyl bromide and other alkyl halides; or chloropicrin; sulphuryl fluoride; borax; tartar emetic.

(9) Selective antifeedants, for example pymetrozine; or flonicamid.

(10) Mite growth inhibitors, for example clofentezine, diflovidazin, hexythiazox, etoxazole.

(11) Microbial disruptors of the insect gut membrane, for example *Bacillus thuringiensis* subspecies *israelensis, Bacillus sphaericus, Bacillus thuringiensis* subspecies *aizawai, Bacillus thuringiensis* subspecies *kurstaki, Bacillus thuringiensis* subspecies *tenebrionis*, and BT plant proteins, for example Cry1Ab, Cry1Ac, Cry1Fa, Cry2Ab, mCry3A, Cry3Ab, Cry3Bb, Cry34/35Ab1.

(12) Oxidative phosphorylation inhibitors, ATP disruptors, for example diafenthiuron; or organotin compounds, for example azocyclotin, cyhexatin, fenbutatin oxide; or propargite; tetradifon.

(13) Oxidative phosphorylation decouplers acting by interrupting the H proton gradient, for example chlorfenapyr and DNOC.

(14) Nicotinergic acetylcholine receptor antagonists, for example bensultap, cartap (hydrochloride), thiocylam, and thiosultap (sodium).

(15) Chitin biosynthesis inhibitors, type 0, for example benzoylureas, for example bistrifluoron, chlorfluazuron, diflubenzuron, flucycloxuron, flufenoxuron, hexaflumuron, lufenuron, novaluron, noviflumuron, teflubenzuron and triflumuron.

(16) Chitin biosynthesis inhibitors, type 1, for example buprofezin.

(17) Moulting disruptors, for example cyromazine.

(18) Ecdysone agonists/disruptors, for example diacylhydrazines, for example chromafenozide, halofenozide, methoxyfenozide and tebufenozide.

(19) Octopaminergic agonists, for example amitraz.

(20) Complex-III electron transport inhibitors, for example hydramethylnone; acequinocyl; fluacrypyrim.

(21) Complex-I electron transport inhibitors, for example from the group of the METI acaricides, for example fenazaquin, fenpyroximate, pyrimidifen, pyridaben, tebufenpyrad, tolfenpyrad; or rotenone (Denis).

(22) Voltage-dependent sodium channel blockers, for example indoxacarb; metaflumizone.

(23) Inhibitors of acetyl-CoA carboxylase, for example tetronic acid derivatives, for example spirodiclofen and spiromesifen; or tetramic acid derivatives, for example spirotetramat.

(24) Complex-IV electron transport inhibitors, for example phosphines, for example aluminium phosphide, calcium phosphide, phosphine, zinc phosphide; or cyanide.

(25) Complex-II electron transport inhibitors, for example cyenopyrafen.

(28) Ryanodine receptor effectors, for example diamides, for example flubendiamide, chlorantraniliprole (Rynaxypyr), cyantraniliprole (Cyazypyr) and also 3-bromo-N-{2-bromo-4-chloro-6-[(1-cyclopropylethyl)carbamoyl]phenyl}-1-(3-chloropyridin-2-yl)-1H-pyrazole-5-carboxamide (known from WO2005/077934) or methyl 2-[3,5-dibromo-2-({[3-bromo-1-(3-chloropyridin-2-yl)-1H-pyrazol-5-yl]carbonyl}amino)benzoyl]-1,2-dimethylhydrazinecarboxylate (known from WO2007/043677).

Further active ingredients with unknown mechanism of action, for example azadirachtin, amidoflumet, benzoximate, bifenazate, chinomethionat, cryolite, cyflumetofen, dicofol, fluensulfone (5-chloro-2-[(3,4,4-trifluorobut-3-en-1-yl)sulphonyl]-1,3-thiazole), flufenerim, pyridalyl and pyrifluquinazon; and also products based on *Bacillus firmus* (I-1582, BioNeem, Votivo) and the following known active compounds:

4-{[(6-bromopyrid-3-yl)methyl](2-fluoroethyl)amino}furan-2(5H)-one (known from WO 2007/115644), 4-{[(6-fluoropyrid-3-yl)methyl](2,2-difluoroethyl)amino}furan-2(5H)-one (known from WO 2007/115644), 4-{[(2-chloro-1,3-thiazol-5-yl)methyl](2-fluoroethyl)amino}furan-2(5H)-one (known from WO 2007/115644), 4-{[(6-chloropyrid-3-yl)methyl](2-fluoroethyl)amino}furan-2(5H)-one (known from WO 2007/115644), 4-{[(6-chloropyrid-3-yl)methyl](2,2-difluoroethyl)amino}furan-2(5H)-one (known from WO 2007/115644), 4-{[(6-chloro-5-fluoropyrid-3-yl)methyl](methyl)amino}furan-2(5H)-one (known from WO 2007/115643), 4-{[(5,6-dichloropyrid-3-yl)methyl](2-fluoroethyl)amino}furan-2(5H)-one (known from WO 2007/115646), 4-{[(6-chloro-5-fluoropyrid-3-yl)methyl](cyclopropyl)amino}furan-2(5H)-one (known from WO 2007/115643), 4-{[(6-chloropyrid-3-yl)methyl](cyclopropyl)amino}furan-2(5H)-one (known from EP-A-0 539 588), 4-{[(6-chloropyrid-3-yl)methyl](methyl)amino}furan-2(5H)-one (known from EP-A-0 539 588), [(6-chloropyridin-3-yl)methyl](methyl)oxido-λ4-sulphanylidenecyanamide (known from WO 2007/149134), [1-(6-chloropyridin-3-yl)ethyl](methyl)oxido-λ4-sulphanylidenecyanamide (known from WO 2007/149134) and its diastereomers (A) and (B)

(A)

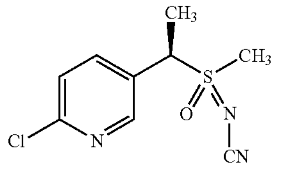

(B)

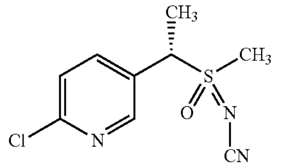

(likewise known from WO 2007/149134), [(6-trifluoromethylpyridin-3-yl)methyl](methyl)oxido-sulphanylidenecyanamide (known from WO 2007/095229), sulfoxaflor (likewise known from WO 2007/149134), 11-(4-chloro-2,6-dimethylphenyl)-12-hydroxy-1,4-dioxa-9-azadispiro[4.2.4.2]tetradec-11-en-10-one (known from WO 2006/089633), 3-(4'-fluoro-2,4-dimethylbiphenyl-3-yl)-4-hydroxy-8-oxa-1-azaspiro[4.5]dec-3-en-2-one (known from WO 2008/067911), 1-[2-fluoro-4-methyl-5-[(2,2,2-trifluoroethyl)sulphinyl]phenyl]-3-(trifluoromethyl)-1H-1,2,4-triazole-5-amine (known from WO 2006/043635),

[(3S,4aR,12R,12aS,12bS)-3-[(cyclopropylcarbonyl)oxy]-6,12-dihydroxy-4,12b-dimethyl-11-oxo-9-(pyridin-3-yl)-1,3,4,4a,5,6,6a,12,12a,12b-decahydro-2H,11H-benzo[f]pyrano[4,3-b]chromen-4-yl]methyl cyclopropanecarboxylate (known from WO 2006/129714), 2-cyano-3-(difluoromethoxy)-N,N-dimethylbenzenesulphonamide (known from WO2006/056433), 2-cyano-3-(difluoromethoxy)-N-methylbenzenesulphonamide (known from WO2006/100288), 2-cyano-3-(difluoromethoxy)-N-ethylbenzenesulphonamide (known from WO2005/035486), 4-(difluoromethoxy)-N-ethyl-N-methyl-1,2-benzothiazole-3-amine 1,1-dioxide (known from WO2007/057407) and N-[1-(2,3-dimethylphenyl)-2-(3,5-dimethylphenyl)ethyl]-4,5-dihydro-1,3-thiazole-2-amine (known from WO2008/104503).

Fungicides:

(1) ergosterol biosynthesis inhibitors, for example aldimorph, azaconazole, bitertanol, bromuconazole, cyproconazole, diclobutrazole, difenoconazole, diniconazole, diniconazole-M, dodemorph, dodemorph acetate, epoxiconazole, etaconazole, fenarimol, fenbuconazole, fenhexamid, fenpropidin, fenpropimorph, fluquinconazole, flurprimidol, flusilazole, flutriafol, furconazole, furconazole-cis, hexaconazole, imazalil, imazalil sulfate, imibenconazole, ipconazole, metconazole, myclobutanil, naftifin, nuarimol, oxpoconazole, paclobutrazole, pefurazoate, penconazole, piperalin, prochloraz, propiconazole, prothioconazole, pyributicarb, pyrifenox, quinconazole, simeconazole, spiroxamine, tebuconazole, terbinafine, tetraconazole, triadimefon, triadimenol, tridemorph, triflumizole, triforine, triticonazole, uniconazole, uniconazole-p, viniconazole, voriconazole, 1-(4-chlorophenyl)-2-(1H-1,2,4-triazol-1-yl)cycloheptanol, methyl 1-(2,2-dimethyl-2,3-dihydro-1H-inden-1-yl)-1H-imidazole-5-carboxylate, N'-{5-(difluoromethyl)-2-methyl-4-[3-(trimethylsilyl)propoxy]phenyl}-N-ethyl-N-methylimidoformamide, N-ethyl-N-methyl-N'-{2-methyl-5-(trifluoromethyl)-4-[3-(trimethylsilyl)propoxy]phenyl}imidoformamide and O-[1-(4-methoxyphenoxy)-3,3-dimethylbutan-2-yl] 1H-imidazole-1-carbothioate, (2) respiration inhibitors (respiratory chain inhibitors), for example bixafen, boscalid, carboxin, diflumetorim, fenfuram, fluopyram, flutolanil, fluxapyroxad, furametpyr, furmecyclox, isopyrazam mixture of the syn-epimeric racemate 1RS,4SR,9RS and of the anti-epimeric racemate 1RS,4SR,9SR, isopyrazam (anti-epimeric racemate), isopyrazam (anti-epimeric enantiomer 1R,4S,9S), isopyrazam (anti-epimeric enantiomer 1S,4R,9R), isopyrazam (syn-epimeric racemate 1RS,4SR,9RS), isopyrazam (syn-epimeric enantiomer 1R,4S,9R), isopyrazam (syn-epimeric enantiomer 1S,4R,9S), mepronil, oxycarboxin, penflufen, penthiopyrad, sedaxane, thifluzamide, 1-methyl-N-[2-(1,1,2,2-tetrafluoroethoxy)phenyl]-3-(trifluoromethyl)-1H-pyrazole-4-carboxamide, 3-(difluoromethyl)-1-methyl-N-[2-(1,1,2,2-tetrafluoroethoxy)phenyl]-1H-pyrazole-4-carboxamide, 3-(difluoromethyl)-N-[4-fluoro-2-(1,1,2,3,3,3-hexafluoropropoxy)phenyl]-1-methyl-1H-pyrazole-4-carboxamide and N-[1-(2,4-dichlorophenyl)-1-methoxypropan-2-yl]-3-(difluoromethyl)-1-methyl-1H-pyrazole-4-carboxamide, (3) respiration inhibitors (respiratory chain inhibitors) acting on complex III of the respiratory chain, for example ametoctradin, amisulbrom, azoxystrobin, cyazofamid, dimoxystrobin, enestroburin, famoxadone, fenamidone, fluoxastrobin, kresoxim-methyl, metominostrobin, orysastrobin, picoxystrobin, pyraclostrobin, pyrametostrobin, pyraoxystrobin, pyribencarb, trifloxystrobin, (2E)-2-(2-{[6-(3-chloro-2-methylphenoxy)-5-fluoropyrimidin-4-yl]oxy}phenyl)-2-(methoxyimino)-N-methylethanamide, (2E)-2-(methoxyimino)-N-methyl-2-(2-{[({(1E)-1-[3-(trifluoromethyl)phenyl]ethylidene}amino)oxy]methyl}phenyl)ethanamide, (2E)-2-(methoxyimino)-N-methyl-2-{2-[(E)-({1-[3-(trifluoromethyl)phenyl]ethoxy}imino)methyl]phenyl}ethanamide, (2E)-2-{2-[({[(1E)-1-(3-{[(E)-1-fluoro-2-phenylethenyl]oxy}phenyl)ethylidene]amino}oxy)methyl]phenyl}-2-(methoxyimino)-N-methylethanamide, (2E)-2-{2-[({[(2E,3E)-4-(2,6-dichlorophenyl)but-3-en-2-ylidene]amino}oxy)methyl]phenyl}-2-(methoxyimino)-N-methylethanamide, 2-chloro-N-(1,1,3-trimethyl-2,3-dihydro-1H-inden-4-yl)pyridine-3-carboxamide, 5-methoxy-2-methyl-4-(2-{[({(1E)-1-[3-(trifluoromethyl)phenyl]ethylidene}amino)oxy]methyl}phenyl)-2,4-dihydro-3H-1,2,4-triazol-3-one, methyl (2E)-2-{2-[({cyclopropyl[(4-methoxyphenyl)imino]methyl}sulphanyl)methyl]phenyl}-3-methoxyprop-2-enoate, N-(3-ethyl-3,5,5-trimethylcyclohexyl)-3-(formylamino)-2-hydroxybenzamide, 2-{2-[(2,5-dimethylphenoxy)methyl]phenyl}-2-methoxy-N-methylacetamide and (2R)-2-{2-[(2,5-dimethylphenoxy)methyl]phenyl}-2-methoxy-N-methylacetamide, (4) mitosis and cell division inhibitors, for example benomyl, carbendazim, chlorfenazole, diethofencarb, ethaboxam, fluopicolide, fuberidazole, pencycuron, thiabendazole, thiophanate-methyl, thiophanate, zoxamide, 5-chloro-7-(4-methylpiperidin-1-yl)-6-(2,4,6-trifluorophenyl)[1,2,4]triazolo[1,5-a]pyrimidine and 3-chloro-5-(6-chloropyridin-3-yl)-6-methyl-4-(2,4,6-trifluorophenyl)pyridazine, (5) compounds with multisite activity, for example Bordeaux mixture, captafol, captan, chlorothalonil, copper formulations such as copper hydroxide, copper naphthenate, copper oxide, copper oxychloride, copper sulphate, dichlofluanid, dithianon, dodine, dodine free base, ferbam, fluorofolpet, folpet, guazatine, guazatine acetate, iminoctadine, iminoctadine albesilate, iminoctadine triacetate, mancopper, mancozeb, maneb, metiram, metiram zinc, oxine-copper, propamidine, propineb, sulphur and sulphur preparations, for example calcium polysulphide, thiram, tolylfluanid, zineb and ziram, (6) resistance inductors, for example acibenzolar-S-methyl, isotianil, probenazole and tiadinil, (7) amino acid and protein biosynthesis inhibitors, for example andoprim, blasticidin-S, cyprodinil, kasugamycin, kasugamycin hydrochloride hydrate, mepanipyrim and pyrimethanil, (8) ATP production inhibitors, for example fentin acetate, fentin chloride, fentin hydroxide and silthiofam, (9) cell wall synthesis inhibitors, for example benthiavalicarb, dimethomorph, flumorph, iprovalicarb, mandipropamid, polyoxins, polyoxorim, validamycin A and valifenalate,

(10) lipid and membrane synthesis inhibitors, for example biphenyl, chloroneb, dicloran, edifenphos, etridiazole, iodocarb, iprobenfos, isoprothiolane, propamocarb, propamocarb hydrochloride, prothiocarb, pyrazophos, quintozene, tecnazene and tolclofos-methyl,

(11) melanin biosynthesis inhibitors, for example carpropamid, diclocymet, fenoxanil, phthalide, pyroquilon and tricyclazole,

(12) nucleic acid synthesis inhibitors, for example benalaxyl, benalaxyl-M (kiralaxyl), bupirimate, clozylacon, dimethirimol, ethirimol, furalaxyl, hymexazol, metalaxyl, metalaxyl-M (mefenoxam), ofurace, oxadixyl, oxolinic acid,

(13) signal transduction inhibitors, for example chlozolinate, fenpiclonil, fludioxonil, iprodione, procymidone, quinoxyfen and vinclozolin,

(14) decouplers, for example binapacryl, dinocap, ferimzone, fluazinam and meptyldinocap,

(15) further compounds, for example benthiazole, bethoxazin, capsimycin, carvone, chinomethionat, chlazafenone, cufraneb, cyflufenamid, cymoxanil, cyprosulfamide, dazomet, debacarb, dichlorophen, diclomezine, difenzoquat, difenzoquat methylsulphate, diphenylamine, ecomat, fenpyrazamine, flumetover, fluoromide, flusulfamide, flutianil, fosetyl-aluminium, fosetyl-calcium, fosetyl-sodium, hexachlorobenzene, irumamycin, methasulfocarb, methyl isothiocyanate, metrafenon, mildiomycin, natamycin, nickel dimethyldithiocarbamate, nitrothal-isopropyl, octhilinone, oxamocarb, oxyfenthiin, pentachlorophenol and salts thereof, phenothrin, phosphoric acid and salts thereof, propamocarb-fosetylate, propanosine-sodium, proquinazid, pyrrolnitrin, tebufloquin, tecloftalam, tolnifanid, triazoxide, trichlamide, zarilamide, 1-(4-{4-[(5R)-5-(2,6-difluorophenyl)-4,5-dihydro-1,2-oxazol-3-yl]-1,3-thiazol-2-yl}piperidin-1-yl)-2-[5-methyl-3-(trifluoromethyl)-1H-pyrazol-1-yl]ethanone, 1-(4-{4-[(5S)-5-(2,6-difluorophenyl)-4,5-dihydro-1,2-oxazol-3-yl]-1,3-thiazol-2-yl}piperidin-1-yl)-2-[5-methyl-3-(trifluoromethyl)-1H-pyrazol-1-yl]ethanone, 1-(4-{4-[5-(2,6-difluorophenyl)-4,5-dihydro-1,2-oxazol-3-yl]-1,3-thiazol-2-yl}piperidin-1-yl)-2-[5-methyl-3-(trifluoromethyl)-1H-pyrazol-1-yl]ethanone, 1-(4-methoxyphenoxy)-3,3-dimethylbutan-2-yl 1H-imidazole-1-carboxylate, 2,3,5,6-tetrachloro-4-(methylsulphonyl)pyridine, 2,3-dibutyl-6-chlorothieno[2,3-d]pyrimidin-4(3H)-one, 2-[5-methyl-3-(trifluoromethyl)-1H-pyrazol-1-yl]-1-(4-{4-[(5R)-5-phenyl-4,5-dihydro-1,2-oxazol-3-yl]-1,3-thiazol-2-yl}piperidin-1-yl)ethanone, 2-[5-methyl-3-(trifluoromethyl)-1H-pyrazol-1-yl]-1-(4-{4-[(5S)-5-phenyl-4,5-dihydro-1,2-oxazol-3-yl]-1,3-thiazol-2-yl}piperidin-1-yl)ethanone, 2-[5-methyl-3-(trifluoromethyl)-1H-pyrazol-1-yl]-1-{4-[4-(5-phenyl-4,5-dihydro-1,2-oxazol-3-yl)-1,3-thiazol-2-yl]piperidin-1-yl}ethanone, 2-butoxy-6-iodo-3-propyl-4H-chromen-4-one, 2-chloro-5-[2-chloro-1-(2,6- difluoro-4-methoxyphenyl)-4-methyl-1H-imidazol-5-yl] pyridine, 2-phenylphenol and salts thereof, 3,4,5-trichloropyridine-2,6-dicarbonitrile, 3-[5-(4-chlorophenyl)-2,3-dimethyl-1,2-oxazolidin-3-yl]pyridine, 3-chloro-5-(4-chlorophenyl)-4-(2,6-difluorophenyl)-6-methylpyridazine, 4-(4-chlorophenyl)-5-(2,6-difluorophenyl)-3,6-dimethyl-pyridazine, 5-amino-1,3,4-thiadiazole-2-thiol, 5-chloro-N'-phenyl-N'-(prop-2-yn-1-yl)thiophene-2-sulphonohydrazide, 5-methyl-6-octyl[1,2,4]triazolo[1,5-a]pyrimidine-7-amine, ethyl (2Z)-3-amino-2-cyano-3-phenylprop-2-enoate, N-(4-chlorobenzyl)-3-[3-methoxy-4-(prop-2-yn-1-yloxy)phenyl] propanamide, N-[(4-chlorophenyl)(cyano)methyl]-3-[3-methoxy-4-(prop-2-yn-1-yloxy)phenyl]propanamide, N-[(5-bromo-3-chloropyridin-2-yl)methyl]-2,4-dichloro-pyridine-3-carboxamide, N-[1-(5-bromo-3-chloropyridin-2-yl)ethyl]-2,4-dichloropyridine-3-carboxamide, N-[1-(5-bromo-3-chloropyridin-2-yl)ethyl]-2-fluoro-4-iodopyridine-3-carboxamide, N-{(E)-[(cyclopropylmethoxy)imino][6-(difluoromethoxy)-2,3-difluorophenyl]methyl}-2-phenylacetamide, N-{(Z)-[(cyclopropylmethoxy)imino][6-(difluoromethoxy)-2,3-difluorophenyl]methyl}-2-phenylacetamide, N-methyl-2-(1-{[5-methyl-3-(trifluoromethyl)-1H-pyrazol-1-yl] acetyl}piperidin-4-yl)-N-(1,2,3,4-tetrahydronaphthalen-1-yl)-1,3-thiazole-4-carboxamide, N-methyl-2-(1-{[5-methyl-3-(trifluoromethyl)-1H-pyrazol-1-yl]acetyl}piperidin-4-yl)-N-[(1R)-1,2,3,4-tetrahydronaphthalen-1-yl]-1,3-thiazole-4-carboxamide, N-methyl-2-(1-{[5-methyl-3-(trifluoromethyl)-1H-pyrazol-1-yl]acetyl}piperidin-4-yl)-N-[(1S)-1,2,3,4-tetrahydronaphthalen-1-yl]-1,3-thiazole-4-carboxamide, pentyl {6-[({[(1-methyl-1H-tetrazol-5-yl)(phenyl)methylidene]amino}oxy)methyl]pyridin-2-yl}carbamate, phenazine-1-carboxylic acid, quinolin-8-ol and quinolin-8-ol sulphate (2:1),

(16) further compounds, for example 1-methyl-3-(trifluoromethyl)-N-[2'-(trifluoromethyl)biphenyl-2-yl]-1H-pyrazole-4-carboxamide, N-(4'-chlorobiphenyl-2-yl)-3-(difluoromethyl)-1-methyl-1H-pyrazole-4-carboxamide, N-(2',4'-dichlorobiphenyl-2-yl)-3-(difluoromethyl)-1-methyl-1H-pyrazole-4-carboxamide, 3-(difluoromethyl)-1-methyl-N-[4'-(trifluoromethyl)biphenyl-2-yl]-1H-pyrazole-4-carboxamide, N-(2',5'-difluorobiphenyl-2-yl)-1-methyl-3-(trifluoromethyl)-1H-pyrazole-4-carboxamide, 3-(difluoromethyl)-1-methyl-N-[4'-(prop-1-yn-1-yl)biphenyl-2-yl]-1H-pyrazole-4-carboxamide, 5-fluoro-1,3-dimethyl-N-[4'-(prop-1-yn-1-yl)biphenyl-2-yl]-1H-pyrazole-4-carboxamide, 2-chloro-N-[4'-(prop-1-yn-1-yl)biphenyl-2-yl]pyridine-3-carboxamide, 3-(difluoromethyl)-N-[4'-(3,3-dimethylbut-1-yn-1-yl)biphenyl-2-yl]-1-methyl-1H-pyrazole-4-carboxamide, N-[4'-(3,3-dimethylbut-1-yn-1-yl) biphenyl-2-yl]-5-fluoro-1,3-dimethyl-1H-pyrazole-4-carboxamide, 3-(difluoromethyl)-N-(4'-ethynylbiphenyl-2-yl)-1-methyl-1H-pyrazole-4-carboxamide, N-(4'-ethynylbiphenyl-2-yl)-5-fluoro-1,3-dimethyl-1H-pyrazole-4-carboxamide, 2-chloro-N-(4'-ethynylbiphenyl-2-yl) pyridine-3-carboxamide, 2-chloro-N-[4'-(3,3-dimethylbut-1-yn-1-yl)biphenyl-2-yl]pyridine-3-carboxamide, 4-(difluoromethyl)-2-methyl-N-[4'-(trifluoromethyl)biphenyl-2-yl]-1,3-thiazole-5-carboxamide, 5-fluoro-N-[4'-(3-hydroxy-3-methylbut-1-yn-1-yl)biphenyl-2-yl]-1,3-dimethyl-1H-pyrazole-4-carboxamide, 2-chloro-N-[4'-(3-hydroxy-3-methylbut-1-yn-1-yl)biphenyl-2-yl]pyridine-3-carboxamide, 3-(difluoromethyl)-N-[4'-(3-methoxy-3-methylbut-1-yn-1-yl)biphenyl-2-yl]-1-methyl-1H-pyrazole-4-carboxamide, 5-fluoro-N-[4'-(3-methoxy-3-methylbut-1-yn-1-yl)biphenyl-2-yl]-1,3-dimethyl-1H-pyrazole-4-carboxamide, 2-chloro-N-[4'-(3-methoxy-3-methylbut-1-yn-1-yl)biphenyl-2-yl]pyridine-3-carboxamide, (5-bromo-2-methoxy-4-methylpyridin-3-yl)(2,3,4-trimethoxy-6-methylphenyl)methanone and N-[2-(4-{[3-(4-chlorophenyl) prop-2-yn-1-yl]oxy}-3-methoxyphenyl)ethyl]-N2-(methylsulphonyl)valinamide.

All mixing partners mentioned in classes (1) to (16) can, if they are capable on the basis of their functional groups, optionally form salts with suitable bases or acids.

The active ingredients identified here by their common names are known and are described, for example, in the pesticide handbook ("The Pesticide Manual" 14th Ed., British Crop Protection Council 2006) or can be found on the Internet (e.g. http://www.alanwood.net/pesticides).

A mixture with other known active ingredients, such as herbicides, fertilizers, growth regulators, safeners, semiochemicals, or else with agents for improving the plant properties, is also possible.

When used as insecticides, the inventive active ingredients may also be present in their commercially available formulations and in the use forms, prepared from these formulations, as a mixture with synergists. Synergists are compounds which enhance the action of the active ingredients, without any need for the synergist added to be active itself.

When used as insecticides, the inventive active ingredients may also be present in their commercially available formulations and in the use forms, prepared from these formulations, as a mixture with inhibitors which reduce degradation of the active ingredient after use in the environment of the plant, on the surface of parts of plants or in plant tissues.

The active ingredient content of the use forms prepared from the commercially available formulations may vary within wide limits. The active ingredient concentration of the use forms may be from 0.00000001 to 95% by weight of active ingredient, preferably between 0.00001 and 1% by weight.

The compounds are applied in a customary manner appropriate for the use forms.

All plants and plant parts can be treated in accordance with the invention. Plants are understood here to mean all plants and plant populations, such as desired and undesired wild plants or crop plants (including naturally occurring crop plants). Crop plants may be plants which can be obtained by conventional breeding and optimization methods or by biotechnological and genetic engineering methods or combinations of these methods, including the transgenic plants and including the plant varieties which are protectable and non-protectable by plant breeders' rights. Parts of plants shall be understood to mean all above-ground and below-ground parts and organs of plants, such as shoot, leaf, flower and root, examples including leaves, needles, stems, trunks, flowers, fruit bodies, fruits and seeds, and also roots, tubers and rhizomes. The plant parts also include harvested material and vegetative and generative propagation material, for example cuttings, tubers, rhizomes, slips and seeds.

The inventive treatment of the plants and plant parts with the active ingredients is effected directly or by allowing them to act on the surroundings, habitat or storage space thereof by the customary treatment methods, for example by dipping, spraying, evaporating, fogging, scattering, painting on, injecting, and, in the case of propagation material, especially in the case of seeds, also by applying one or more coats.

As already mentioned above, it is possible to treat all plants and their parts in accordance with the invention. In a preferred embodiment, wild plant species and plant cultivars, or those obtained by conventional biological breeding methods, such as crossing or protoplast fusion, and also parts thereof, are treated. In a further preferred embodiment, transgenic plants and plant cultivars obtained by genetic engineering methods, if appropriate in combination with conventional methods (Genetically Modified Organisms), and parts thereof are treated. The terms "parts" or "parts of plants" or "plant parts" have been explained above.

More preferably, plants of the plant cultivars which are commercially available or are in use are treated in accordance with the invention. Plant cultivars are understood to mean plants having new properties ("traits") and which have been obtained by conventional breeding, by mutagenesis or by recombinant DNA techniques. They may be cultivars, biotypes and genotypes.

Depending on the plant species or plant cultivars, and the location and growth conditions (soils, climate, vegetation period, diet) thereof, the inventive treatment may also result in superadditive ("synergistic") effects. For example, possibilities include reduced application rates and/or broadening of the activity spectrum and/or an increase in the activity of the compounds and compositions usable in accordance with the invention, better plant growth, increased tolerance to high or low temperatures, increased tolerance to drought or to levels of water or soil salinity, enhanced flowering performance, easier harvesting, accelerated ripening, higher yields, higher quality and/or higher nutritional value of the harvested products, increased storage life and/or processibility of the harvested products, which exceed the effects normally to be expected.

The transgenic plants or plant cultivars (those obtained by genetic engineering) which are to be treated with preference in accordance with the invention include all plants which, through the genetic modification, received genetic material which imparts particular advantageous useful properties ("traits") to these plants. Examples of such properties are better plant growth, increased tolerance to high or low temperatures, increased tolerance to drought or to levels of water or soil salinity, enhanced flowering performance, easier harvesting, accelerated ripening, higher yields, higher quality and/or a higher nutritional value of the harvested products, longer storage life and/or processibility of the harvested products. Further and particularly emphasized examples of such properties are an improved defence of the plants against animal and microbial pests, such as against insects, mites, phytopathogenic fungi, bacteria and/or viruses, and also increased tolerance of the plants to certain herbicidally active ingredients. Examples of transgenic plants include the important crop plants, such as cereals (wheat, rice), maize, soya, potatoes, sugarbeet, tomatoes, peas and other vegetable types, cotton, tobacco, oilseed rape, and also fruit plants (with the fruits of apples, pears, citrus fruits and grapes), particular emphasis being given to maize, soya, potatoes, cotton, tobacco and oilseed rape. Traits that are particularly emphasized are improved defence of the plants against insects, arachnids, nematodes, slugs and snails by toxins formed in the plants, especially those formed in the plants by the genetic material from *Bacillus thuringiensis* (for example by the genes CryIA(a), CryIA(b), CryIA(c), CryIIA, CryIIIA, CryIIIB2, Cry9c, Cry2Ab, Cry3Bb and CryIF, and also combinations thereof) (referred to hereinafter as "Bt plants"). Traits that are also particularly emphasized are the improved defence of plants against fungi, bacteria and viruses by systemic acquired resistance (SAR), systemin, phytoalexins, elicitors and also resistance genes and correspondingly expressed proteins and toxins. Traits that are additionally particularly emphasized are the increased tolerance of the plants to certain active herbicidal ingredients, for example imidazolinones, sulphonylureas, glyphosate or phosphinothricin (for example the "PAT" gene). The genes which impart the desired traits in question may also be present in combinations with one another in the transgenic plants. Examples of "Bt plants" include maize varieties, cotton varieties, soya varieties and potato varieties which are sold under the trade names YIELD GARD® (for example maize, cotton, soya), KnockOut® (for example maize), StarLink® (for example maize), Bollgard® (cotton), Nucotn® (cotton) and NewLeaf® (potato). Examples of herbicide-tolerant plants include maize varieties, cotton varieties and soya varieties which are sold under the trade names Roundup Ready® (tolerance to glyphosate, for example maize, cotton, soya), Liberty Link® (tolerance to phosphinothricin, for example oilseed rape), IMI® (tolerance to imidazolinones) and STS® (tolerance to sulphonylureas, for example maize). Herbicide-resistant plants (plants bred in a conventional manner for herbicide tolerance) also include the varieties sold under the Clearfield® name (for example maize). Of course, these statements also apply to plant cultivars which have these genetic traits or genetic traits which are still to be developed and will be developed and/or marketed in the future.

The plants listed can be treated in accordance with the invention in a particularly advantageous manner with the compounds of the general formula I and/or the active ingredient mixtures according to the invention. The preferred ranges stated above for the active ingredients or mixtures also apply to the treatment of these plants. Particular emphasis is given to the treatment of plants with the compounds or mixtures specifically mentioned in the present text.

In addition, the inventive active ingredients can be used to control a multitude of different pests, including, for example, harmful sucking insects, biting insects and other pests which are plant parasites, stored material pests, pests which destroy industrial material, and hygiene pests including parasites in the animal health sector, and for the control thereof, for example the elimination and eradication thereof. The present invention thus also includes a method for controlling pests.

In the animal health sector, i.e. in the field of veterinary medicine, the active ingredients according to the present invention act against animal parasites, especially ectoparasites or endoparasites. The term "endoparasites" includes especially helminths such as cestodes, nematodes or trematodes, and protozoa such as coccidia. Ectoparasites are typically and preferably arthropods, especially insects such as flies (biting and licking), parasitic fly larvae, lice, hair lice, bird lice, fleas and the like; or acaricides such as ticks, for example hard ticks or soft ticks, or mites such as scab mites, harvest mites, bird mites and the like.

These parasites include:

From the order of the Anoplurida, for example, *Haematopinus* spp., *Linognathus* spp., *Pediculus* spp., *Phtirus* spp. and *Solenopotes* spp.; specific examples are: *Linognathus setosus, Linognathus vituli, Linognathus ovillus, Linognathus oviformis, Linognathus pedalis, Linognathus stenopsis, Haematopinus asini macrocephalus, Haematopinus eurysternus, Haematopinus suis, Pediculus humanus capitis, Pediculus humanus corporis, Phylloera vastatrix, Phthirus pubis, Solenopotes capillatus;*

From the order of the Mallophagida and the suborders Amblycerina and Ischnocerina, for example, *Trimenopon* spp., *Menopon* spp., *Trinoton* spp., *Bovicola* spp., *Werneckiella* spp., *Lepikentron* spp., *Damalina* spp., *Trichodectes* spp. and *Felicola* spp.; specific examples are: *Bovicola*

*bovis, Bovicola ovis, Bovicola limbata, Damalina bovis, Trichodectes canis, Felicola subrostratus, Bovicola caprae, Lepikentron ovis, Werneckiella equi;*

From the order of the Diptera and the suborders Nematocerina and Brachycerina, for example, *Aedes* spp., *Anopheles* spp., *Culex* spp., *Simulium* spp., *Eusimulium* spp., *Phlebotomus* spp., *Lutzomyia* spp., *Culicoides* spp., *Chrysops* spp., *Odagmia* spp., *Wilhelmia* spp., *Hybomitra* spp., *Atylotus* spp., *Tabanus* spp., *Haematopota* spp., *Philipomyia* spp., *Braula* spp., *Musca* spp., *Hydrotaea* spp., *Stomoxys* spp., *Haematobia* spp., *Morellia* spp., *Fannia* spp., *Glossina* spp., *Calliphora* spp., *Lucilia* spp., *Chrysomyia* spp., *Wohlfahrtia* spp., *Sarcophaga* spp., *Oestrus* spp., *Hypoderma* spp., *Gasterophilus* spp., *Hippobosca* spp., *Lipoptena* spp., *Melophagus* spp., *Rhinoestrus* spp., *Tipula* spp.; specific examples are: *Aedes aegypti, Aedes albopictus, Aedes taeniorhynchus, Anopheles gambiae, Anopheles maculipennis, Calliphora erythrocephala, Chrysozona pluvialis, Culex quinquefasciatus, Culex pipiens, Culex tarsalis, Fannia canicularis, Sarcophaga carnaria, Stomoxys calcitrans, Tipula paludosa, Lucilia cuprina, Lucilia sericata, Simulium reptans, Phlebotomus papatasi, Phlebotomus longipalpis, Odagmia ornata, Wilhelmia equina, Boophthora erythrocephala, Tabanus bromius, Tabanus spodopterus, Tabanus atratus, Tabanus sudeticus, Hybomitra ciurea, Chrysops caecutiens, Chrysops relictus, Haematopota pluvialis, Haematopota italica, Musca autumnalis, Musca domestica, Haematobia irritans irritans, Haematobia irritans exigua, Haematobia stimulans, Hydrotaea irritans, Hydrotaea albipuncta, Chrysomya chloropyga, Chrysomya bezziana, Oestrus ovis, Hypoderma bovis, Hypoderma lineatum, Przhevalskiana silenus, Dermatobia hominis, Melophagus ovinus, Lipoptena capreoli, Lipoptena cervi, Hippobosca variegata, Hippobosca equina, Gasterophilus intestinalis, Gasterophilus haemorroidalis, Gasterophilus inermis, Gasterophilus nasalis, Gasterophilus nigricornis, Gasterophilus pecorum, Braula coeca;*

From the order of the Siphonapterida, for example *Pulex* spp., *Ctenocephalides* spp., *Tunga* spp., *Xenopsylla* spp., *Ceratophyllus* spp.; specific examples are: *Ctenocephalides canis, Ctenocephalides felis, Pulex irritans, Tunga penetrans, Xenopsylla cheopis;*

From the order of the Heteropterida, for example, *Cimex* spp., *Triatoma* spp., *Rhodnius* spp. and *Panstrongylus* spp.

From the order of the Blattarida, for example *Blatta orientalis, Periplaneta americana, Blattela germanica* and *Supella* spp. (e.g. *Suppella longipalpa*);

From the subclass of the Acari (Acarina) and the orders of the Meta- and Mesostigmata, for example, *Argas* spp., *Ornithodorus* spp., *Otobius* spp., *Ixodes* spp., *Amblyomma* spp., *Rhipicephalus* (*Boophilus*) spp., *Dermacentor* spp., *Haemophysalis* spp., *Hyalomma* spp., *Dermanyssus* spp., *Rhipicephalus* spp. (the original genus of multihost ticks), *Ornithonyssus* spp., *Pneumonyssus* spp., *Raillietia* spp., *Pneumonyssus* spp., *Sternostoma* spp., *Varroa* spp., *Acarapis* spp.; specific examples are: *Argas persicus, Argas reflexus, Ornithodorus moubata, Otobius megnini, Rhipicephalus* (*Boophilus*) *microplus, Rhipicephalus* (*Boophilus*) *decoloratus, Rhipicephalus* (*Boophilus*) *annulatus, Rhipicephalus* (*Boophilus*) *calceratus, Hyalomma anatolicum, Hyalomma aegypticum, Hyalomma marginatum, Hyalomma transiens, Rhipicephalus evertsi, Ixodes ricinus, Ixodes hexagonus, Ixodes canisuga, Ixodes pilosus, Ixodes rubicundus, Ixodes scapularis, Ixodes holocyclus, Haemaphysalis concinna, Haemaphysalis punctata, Haemaphysalis cinnabarina, Haemaphysalis otophila, Haemaphysalis leachi, Haemaphysalis longicorni, Dermacentor marginatus, Dermacentor reticulatus, Dermacentor pictus, Dermacentor albipictus, Dermacentor andersoni, Dermacentor variabilis, Hyalomma mauritanicum, Rhipicephalus sanguineus, Rhipicephalus bursa, Rhipicephalus appendiculatus, Rhipicephalus capensis, Rhipicephalus turanicus, Rhipicephalus zambeziensis, Amblyomma americanum, Amblyomma variegatum, Amblyomma maculatum, Amblyomma hebraeum, Amblyomma cajennense, Dermanyssus gallinae, Ornithonyssus bursa, Ornithonyssus sylviarum, Varroa jacobsoni;*

From the order of the Actinedida (Prostigmata) and Acaridida (Astigmata), for example, *Acarapis* spp., *Cheyletiella* spp., *Ornithocheyletia* spp., *Myobia* spp., *Psorergates* spp., *Demodex* spp., *Trombicula* spp., *Listrophorus* spp., *Acarus* spp., *Tyrophagus* spp., *Caloglyphus* spp., *Hypodectes* spp., *Pterolichus* spp., *Psoroptes* spp., *Chorioptes* spp., *Otodectes* spp., *Sarcoptes* spp., *Notoedres* spp., *Knemidocoptes* spp., *Cytodites* spp. and *Laminosioptes* spp.; specific examples are: *Cheyletiella yasguri, Cheyletiella blakei, Demodex canis, Demodex bovis, Demodex ovis, Demodex caprae, Demodex equi, Demodex caballi, Demodex suis, Neotrombicula autumnalis, Neotrombicula desaleri, Neoschongastia xerothermobia, Trombicula akamushi, Otodectes cynotis, Notoedres cati, Sarcoptis canis, Sarcoptes bovis, Sarcoptes ovis, Sarcoptes rupicaprae* (=*S. caprae*), *Sarcoptes equi, Sarcoptes suis, Psoroptes ovis, Psoroptes cuniculi, Psoroptes equi, Chorioptes bovis, Psoergates ovis, Pneumonyssoidic mange, Pneumonyssoides caninum, Acarapis woodi.*

The inventive active ingredients are also suitable for controlling arthropods, helminths and protozoa which attack animals. The animals include agricultural livestock, for example cattle, sheep, goats, horses, pigs, donkeys, camels, buffalo, rabbits, chickens, turkeys, ducks, geese, cultured fish, honeybees. The animals also include domestic animals—also referred to as companion animals—for example dogs, cats, caged birds, aquarium fish, and what are known as test animals, for example hamsters, guinea pigs, rats and mice.

The control of these arthropods, helminths and/or protozoa should reduce cases of death and improve the performance (for meat, milk, wool, hides, eggs, honey etc.) and the health of the host animal, and so the use of the inventive active ingredients enables more economically viable and easier animal husbandry.

For example, it is desirable to prevent or to interrupt the uptake of blood from the host by the parasites (if relevant). Control of the parasites can also contribute to preventing the transmission of infectious substances.

The term "control" as used herein with regard to the field of animal health means that the active ingredients act by reducing the occurrence of the parasite in question in an animal infested with such parasites to a harmless level. More specifically, "control" as used herein means that the active ingredient kills the parasite in question, retards its growth or inhibits its proliferation.

In general, the inventive active ingredients can employed directly when they are used for the treatment of animals. They are preferably employed in the form of pharmaceutical compositions which may comprise the pharmaceutically acceptable excipients and/or auxiliaries known in the prior art.

In the sector of animal health and in animal husbandry, the active ingredients are employed (administered) in a known manner, by enteral administration in the form of, for example, tablets, capsules, potions, drenches, granules, pastes, boluses, the feed-through process and suppositories, by parenteral administration, for example by injection (intramuscular, subcutaneous, intravenous, intraperitoneal inter alia), implants, by nasal administration, by dermal administration in the form, for example, of dipping or bathing, spraying, pouring on and spotting on, washing and powdering, and also with the aid of moulded articles containing the active ingredient, such as collars, earmarks, tailmarks, limb bands, halters, marking devices, etc. The active ingredients can be formulated as a shampoo or as suitable formulations applicable in aerosols or unpressurized sprays, for example pump sprays and atomizer sprays, In the case of employment for livestock, poultry, domestic pets, etc., the inventive active ingredients can be employed as formulations (for example powders, wettable powders ["WP"], emulsions, emulsifiable concentrates ["EC"], free-flowing compositions, homogeneous solutions and suspension concentrates ["SC"]), which contain the active ingredients in an amount of 1 to 80% by weight, directly or after dilution (e.g. 100- to 10 000-fold dilution), or they can be used as a chemical bath.

It has also been found that the inventive compounds have strong insecticidal action against insects which destroy industrial materials.

Preferred but nonlimiting examples include the following insects:

beetles, such as *Hylotrupes bajulus, Chlorophorus pilosis, Anobium punctatum, Xestobium rufovillosum, Ptilinus pecticornis, Dendrobium pertinex, Ernobius mollis, Priobium carpini, Lyctus brunneus, Lyctus africanus, Lyctus planicollis, Lyctus linearis, Lyctus pubescens, Trogoxylon aequale, Minthes rugicollis, Xyleborus* spec. *Tryptodendron* spec., *Apate monachus, Bostrychus capucins, Heterobostrychus brunneus, Sinoxylon* spec. *Dinoderus minutus;* dermapterans, such as *Sirex juvencus, Urocerus gigas, Urocerus gigas taignus, Urocerus augur;* termites, such as *Kalotermes flavicollis, Cryptotermes brevis, Heterotermes indicola, Reticulitermes flavipes, Reticulitermes santonensis, Reticulitermes lucifugus, Mastotermes darwiniensis, Zootermopsis nevadensis, Coptotermes formosanus;*

Bristletails such as *Lepisma saccharina.*

Industrial materials in the present context are understood to mean inanimate materials, such as preferably plastics, adhesives, sizes, papers and cards, leather, wood, processed wood products and coating compositions.

The ready-to-use compositions may optionally also comprise other insecticides, and optionally also one or more fungicides.

With respect to possible additional mixing partners, reference is made to the insecticides and fungicides mentioned above.

At the same time, the inventive compounds can be used for protection of objects which come into contact with saltwater or brackish water, especially hulls, screens, nets, buildings, moorings and signalling systems, against fouling.

In addition, the inventive compounds can be used as antifouling compositions, alone or in combinations with other active ingredients.

The active ingredients are also suitable for controlling animal pests in the domestic sector, in the hygiene sector and in the protection of stored products, especially insects, arachnids and mites, which are found in enclosed spaces, for example homes, factory halls, offices, vehicle cabins and the like. They can be used to control these pests alone or in combination with other active ingredients and auxiliaries in domestic insecticide products. They are effective against sensitive and resistant species, and against all developmental stages. These pests include:

From the order of the Scorpionidea, for example, *Buthus occitanus.*

From the order of the Acarina, for example, *Argas persicus, Argas reflexus, Bryobia* spp., *Dermanyssus gallinae, Glyciphagus domesticus, Ornithodorus moubat, Rhipicephalus sanguineus, Trombicula alfreddugesi, Neutrombicula autumnalis, Dermatophagoides pteronissimus, Dermatophagoides forinae.*

From the order of the Araneae, for example, *Aviculariidae, Araneidae.*

From the order of the Opiliones, for example, *Pseudoscorpiones chelifer, Pseudoscorpiones cheiridium, Opiliones phalangium.*

From the order of the Isopoda, for example, *Oniscus asellus, Porcellio scaber.*

From the order of the Diplopoda, for example, *Blaniulus guttulatus, Polydesmus* spp.

From the order of the Chilopoda, for example, *Geophilus* spp.

From the order of the Zygentoma, for example, *Ctenolepisma* spp., *Lepisma saccharina, Lepismodes inquilinus.*

From the order of the Blattaria, for example, *Blatta orientalies, Blattella germanica, Blattella asahinai, Leucophaea maderae, Panchlora* spp., *Parcoblatta* spp., *Periplaneta australasiae, Periplaneta americana, Periplaneta brunnea, Periplaneta fuliginosa, Supella longipalpa.*

From the order of the Saltatoria, for example, *Acheta domesticus.*

From the order of the Isoptera, for example, *Kalotermes* spp., *Reticulitermes* spp.

From the order of the Psocoptera, for example, *Lepinatus* spp., *Liposcelis* spp.

From the order of the Coleoptera, for example, *Anthrenus* spp., *Attagenus* spp., *Dermestes* spp., *Latheticus oryzae, Necrobia* spp., *Ptinus* spp., *Rhizopertha dominica, Sitophilus granarius, Sitophilus oryzae, Sitophilus zeamais, Stegobium paniceum.*

From the order of the Diptera, for example, *Aedes aegypti, Aedes albopictus, Aedes taeniorhynchus, Anopheles* spp., *Calliphora erythrocephala, Chrysozona pluvialis, Culex quinquefasciatus, Culex pipiens, Culex tarsalis, Drosophila* spp., *Fannia canicularis, Musca domestica, Phlebotomus* spp., *Sarcophaga carnaria, Simulium* spp., *Stomoxys calcitrans, Tipula paludosa.*

From the order of the Lepidoptera, for example, *Achroia grisella, Galleria mellonella, Plodia interpunctella, Tinea cloacella, Tinea pellionella, Tineola bisselliella.*

From the order of the Siphonaptera, for example, *Ctenocephalides canis, Ctenocephalides felis, Pulex irritans, Tunga penetrans, Xenopsylla* cheopis.

From the order of the Hymenoptera, for example, *Camponotus herculeanus, Lasius fuliginosus, Lasius niger, Lasius umbratus, Monomorium pharaonis, Paravespula* spp., *Tetramorium caespitum.*

From the order of the Anoplura, for example, *Pediculus humanus capitis, Pediculus humanus corporis, Pemphigus* spp., *Phylloera vastatrix, Phthirus pubis.*

From the order of the Heteroptera, for example, *Cimex hemipterus, Cimex lectularius, Rhodinus prolixus, Triatoma infestans.*

In the field of domestic insecticides, they are used alone or in combination with other suitable active ingredients, such as phosphoric esters, carbamates, pyrethroids, neonicotinoids, growth regulators or active ingredients from other known classes of insecticides.

They are employed in aerosols, unpressurized spray products, for example pump and atomizer sprays, automatic fogging systems, foggers, foams, gels, evaporator products with evaporator tablets made of cellulose or plastic, liquid evaporators, gel and membrane evaporators, propeller-driven evaporators, energy-free or passive evaporation systems, moth papers, moth bags and moth gels, as granules or dusts, in baits for spreading or in bait stations.

Elucidation of the preparation processes and intermediates

PREPARATION EXAMPLES

Example No. B

Synthesis of methyl 4-amino-3-(tert-butylcarbamoyl)-5-methylbenzoate 3.0 g (8.04 mmol) of 2-amino-N-tert-butyl-5-iodo-3-methylbenzamide, 1.78 g (17.68 mmol) of triethylamine and 0.56 g (0.80 mmol) of bis(triphenylphosphine)palladium dichloride are added to 40 ml of methanol, and the mixture is stirred in an autoclave at 110° C. under 115 bar of carbon monoxide for 9 h. The mixture is filtered, the solids are washed with methanol and the organic phase is concentrated. The desired product is obtained by chromatographic purification.

(log P: 2.48; MH+: 265; 1H NMR (400 MHz, DMSO, 6, ppm): 1.38 (s, 9H), 2.11 (s, 3H), 3.77 (s, 3H), 6.63 (br. s, 2H), 7.63 (s, 1H), 7.84 (s, 1H), 7.88 (s, 1H)

PREPARATION EXAMPLES

The preparation processes described above can be used to obtain the compounds of the formula (I), and some of the compounds of the formula (I) may be present as regioisomers. In the table which follows, in relation to the NMR data, the chemical shifts and the corresponding signal intensities are reported in each case, for example for compound 1:

Signal 1

10.310; 0.82; for 10.310 ppm (chemical shift) 0.82 (signal intensity);

Signal 2

8.477; 0.62; for 8.477 ppm (chemical shift) 0.62 (signal intensity);

| No. | Structure | LOGP (HCOOH) | MH+ | NMR(DMSO-d6) |
|---|---|---|---|---|
| 1 | 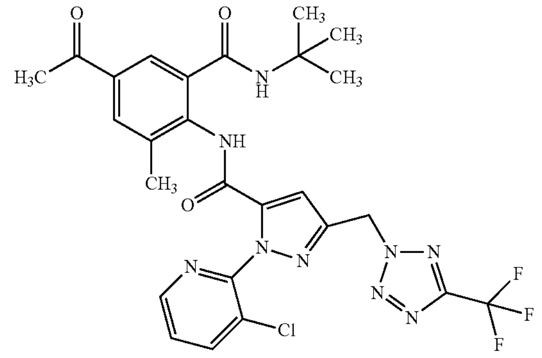 [SMILES: CC(=O)c1cc(C)c(NC(=O)c2cc(Cn3nnc(C(F)(F)F)n3)nn2-c2ncccc2Cl)c(C(=O)NC(C)(C)C)c1] | 3.26 | 604 | (10.310; 0.82), (8.477; 0.62), (8.474; 0.66), (8.466; 0.67), (8.462; 0.65), (8.156; 0.60), (8.152; 0.61), (8.135; 0.68), (8.132; 0.64), (7.891; 0.74), (7.887; 0.77), (7.753; 0.84), (7.748; 0.78), (7.606; 0.69), (7.594; 1.39), (7.586; 0.77), (7.574; 0.61), (7.344; 1.10), (6.324; 2.53), (3.289; 48.00), (2.574; 5.25), (2.538; 0.40), (2.521; 0.32), (2.508; 4.90), (2.503; 9.61), (2.499; 12.79), (2.494; 9.10), (2.490; 4.30), (2.222; 3.51), (1.225; 15.00), (−0.000; 1.27) |
| 2 | 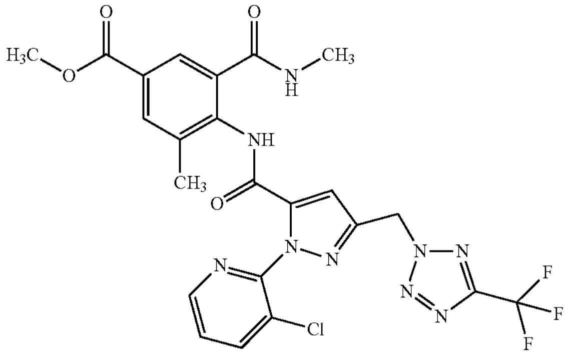 [SMILES: CNC(=O)c1cc(C(=O)OC)cc(C)c1NC(=O)c1cc(Cn2nnc(C(F)(F)F)n2)nn1-c1ncccc1Cl] | 2.77 | 578 | (10.469; 2.41), (8.483; 1.92), (8.480; 2.04), (8.472; 2.17), (8.468; 2.27), (8.457; 0.47), (8.453; 0.42), (8.326; 1.11), (8.315; 1.10), (8.160; 1.81), (8.156; 1.82), (8.140; 2.17), (8.136; 2.06), (8.118; 0.41), (8.114; 0.37), (7.923; 2.36), (7.920; 2.57), (7.866; 2.74), (7.862; 2.43), (7.606; 1.89), (7.594; 1.89), (7.591; 0.77), (7.586; 1.82), (7.579; 0.63), (7.574; 1.82), (7.570; 0.57), (7.559; 0.37), (7.380; 2.39), (7.330; 0.42), (6.318; 7.13), (6.100; 1.16), (3.940; 0.32), (3.858; 16.00), (3.313; 473.05), (3.290; 6.23), (2.677; 7.60), (2.665; 7.72), (2.540; 0.73), (2.523; 2.22), (2.510; 26.00), (2.505; 47.75), (2.501; 62.03), (2.496; 43.35), (2.492; 21.02), (2.405; 0.79), (2.332; 0.35), (2.327; 0.45), (2.217; 10.00), (1.987; 0.78), (1.175; 0.42), (−0.000; 0.93) |

-continued
| | | | | |
|---|---|---|---|---|
| 3 | 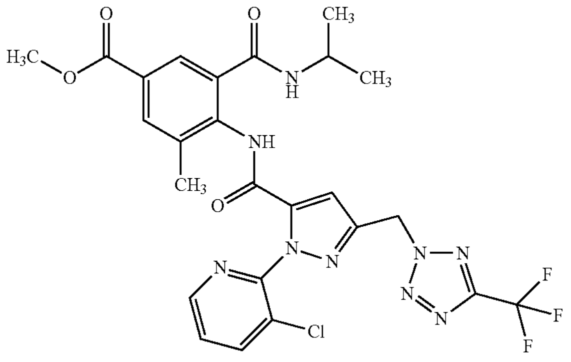 [SMILES: COC(=O)c1cc(C)c(NC(=O)c2cc(Cn3nnc(C(F)(F)F)n3)nn2-c2ncccc2Cl)c(C(=O)NC(C)C)c1] | 3.21 | 606 | (10.377; 2.77), (8.471; 1.97), (8.467; 2.08), (8.459; 2.16), (8.455; 2.19), (8.444; 0.40), (8.441; 0.38), (8.147; 2.06), (8.143; 2.12), (8.132; 1.77), (8.127; 2.89), (8.123; 2.55), (8.113; 1.56), (8.105; 0.68), (8.101; 0.49), (7.914; 2.53), (7.911; 2.68), (7.819; 2.77), (7.815; 2.62), (7.602; 1.95), (7.590; 1.97), (7.586; 0.79), (7.581; 1.88), (7.574; 0.63), (7.569; 1.85), (7.381; 2.98), (7.332; 0.46), (6.321; 7.37), (6.102; 1.07), (3.943; 0.72), (3.939; 0.67), (3.927; 1.06), (3.908; 1.00), (3.891; 0.92), (3.861; 16.00), (3.303; 208.29), (3.280; 1.94), (2.669; 0.36), (2.539; 0.70), (2.509; 21.88), (2.504; 40.04), (2.500; 51.92), (2.496; 36.82), (2.491; 18.21), (2.327; 0.39), (2.226; 10.27), (2.070; 0.45), (1.072; 0.32), (1.031; 4.19), (1.025; 14.08), (1.015; 4.81), (1.009; 14.03), (−0.000; 4.52) |
| 4 | 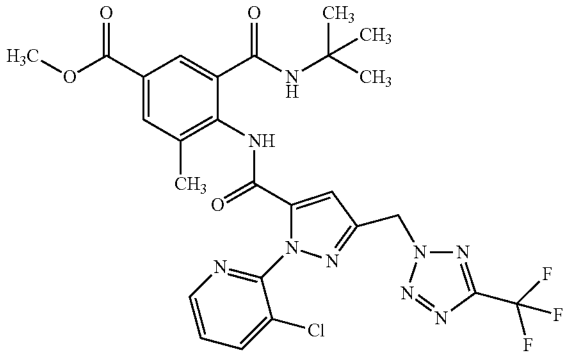 [SMILES: COC(=O)c1cc(C)c(NC(=O)c2cc(Cn3nnc(C(F)(F)F)n3)nn2-c2ncccc2Cl)c(C(=O)NC(C)(C)C)c1] | 3.52 | 620 | (10.310; 1.08), (8.478; 0.71), (8.474; 0.73), (8.466; 0.80), (8.462; 0.77), (8.159; 0.68), (8.155; 0.65), (8.139; 0.81), (8.135; 0.74), (7.891; 0.94), (7.887; 0.99), (7.770; 1.00), (7.766; 1.00), (7.650; 1.09), (7.607; 0.69), (7.595; 0.70), (7.587; 0.67), (7.575; 0.66), (7.343; 1.30), (6.327; 2.65), (6.108; 0.40), (3.857; 5.71), (3.307; 43.52), (2.509; 4.45), (2.505; 7.99), (2.500; 10.19), (2.496; 7.14), (2.492; 3.45), (2.217; 3.80), (2.208; 0.91), (1.221; 4.21), (1.214; 16.00) |
| 5 | 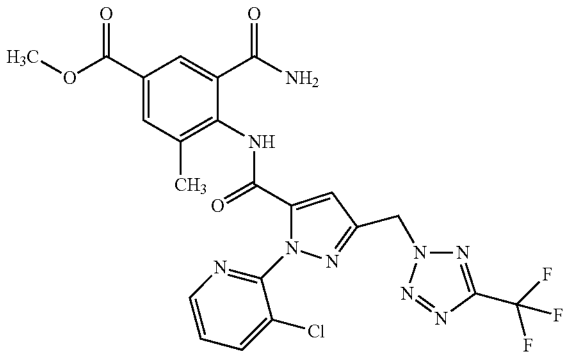 [SMILES: COC(=O)c1cc(C)c(NC(=O)c2cc(Cn3nnc(C(F)(F)F)n3)nn2-c2ncccc2Cl)c(C(N)=O)c1] | 2.56 | 564 | (10.527; 1.78), (8.491; 1.97), (8.487; 2.10), (8.479; 2.23), (8.475; 2.25), (8.465; 0.46), (8.462; 0.41), (8.159; 1.68), (8.155; 1.68), (8.139; 2.10), (8.135; 1.99), (8.118; 0.38), (8.114; 0.35), (7.952; 2.10), (7.920; 2.35), (7.863; 0.75), (7.605; 1.73), (7.593; 1.82), (7.585; 1.74), (7.579; 0.68), (7.573; 1.69), (7.559; 0.40), (7.556; 0.35), (7.536; 0.52), (7.517; 0.41), (7.476; 1.19), (7.362; 1.25), (7.026; 0.68), (7.007; 0.63), (6.308; 7.01), (6.090; 1.15), (5.747; 1.88), (4.040; 0.38), (4.022; 0.36), (3.890; 0.41), (3.862; 16.00), (3.835; 0.44), (3.306; 149.57), (2.539; 0.65), (2.509; 18.46), (2.505; 33.45), (2.500; 43.01), (2.496; 30.51), (2.492; 15.15), (2.405; 5.46), (2.199; 9.30), (2.070; 0.47), (1.987; 1.54), (1.193; 0.42), (1.175; 0.84), (1.157; 0.43), (−0.000; 2.30) |

-continued
| No. | Structure | LOGP | MH+ | NMR |
|---|---|---|---|---|
| 6 | 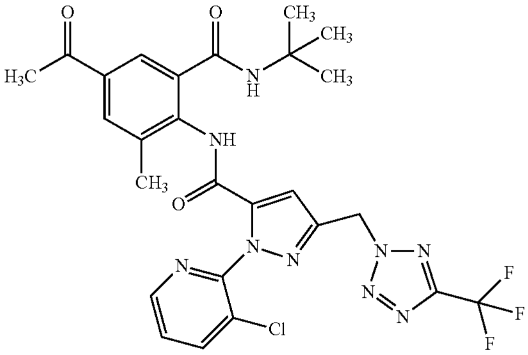 [SMILES: CC(=O)c1cc(C)c(NC(=O)c2cc(Cn3nnc(C(F)(F)F)n3)nn2-c2ncccc2Cl)c(C(=O)NC(C)(C)C)c1] | 2.87 | 606 | (10.083; 1.10), (8.474; 0.71), (8.470; 0.76), (8.462; 0.77), (8.458; 0.75), (8.153; 0.69), (8.150; 0.69), (8.133; 0.77), (8.130; 0.73), (7.604; 0.72), (7.592; 0.71), (7.583; 0.69), (7.572; 0.66), (7.311; 1.98), (7.250; 0.91), (7.190; 1.10), (7.182; 1.39), (6.319; 2.89), (5.746; 0.79), (5.171; 0.92), (5.160; 0.94), (4.686; 0.33), (4.682; 0.34), (3.312; 126.86), (2.509; 7.69), (2.505; 14.02), (2.500; 18.07), (2.496; 12.68), (2.492; 6.18), (2.128; 3.90), (1.305; 2.43), (1.289; 2.42), (1.195; 16.00), (−0.000; 1.02) |
| 7 | 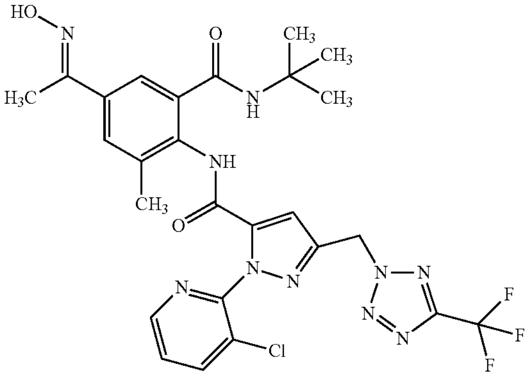 [SMILES: C/C(=N\O)c1cc(C)c(NC(=O)c2cc(Cn3nnc(C(F)(F)F)n3)nn2-c2ncccc2Cl)c(C(=O)NC(C)(C)C)c1] | 3 | 619 | (11.241; 2.57), (10.161; 1.13), (8.476; 0.72), (8.473; 0.75), (8.465; 0.77), (8.461; 0.74), (8.156; 0.70), (8.153; 0.68), (8.136; 0.78), (8.132; 0.72), (7.606; 0.72), (7.594; 0.72), (7.585; 0.69), (7.574; 0.69), (7.556; 0.85), (7.553; 0.92), (7.480; 0.97), (7.475; 0.87), (7.438; 1.15), (7.324; 1.87), (6.320; 2.76), (3.315; 271.67), (2.540; 0.59), (2.510; 14.54), (2.505; 26.34), (2.501; 33.77), (2.496; 23.56), (2.492; 11.48), (2.167; 3.92), (2.134; 5.79), (1.987; 0.65), (1.207; 16.00), (1.193; 0.52), (1.175; 0.43) |
| No. | Structure | LOGP | MH+ | NMR |
| 8 | 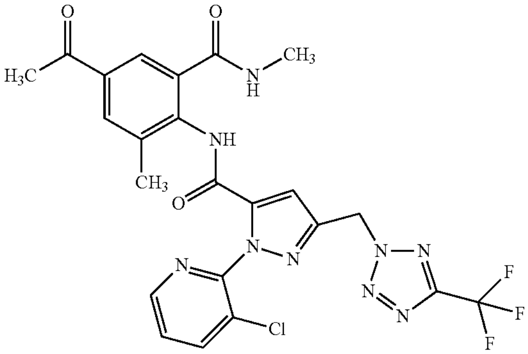 [SMILES: CNC(=O)c1cc(C(C)=O)cc(C)c1NC(=O)c1cc(Cn2nnc(C(F)(F)F)n2)nn1-c1ncccc1Cl] | 2.53 | 562 | (10.4922; 2.63), (8.4851; 1.95), (8.4814; 2.05), (8.4734; 2.09), (8.4696; 1.98), (8.3314; 1.16), (8.3200; 1.13), (8.1605; 1.89), (8.1568; 1.88), (8.1403; 2.10), (8.1366; 1.93), (7.9219; 2.31), (7.9186; 2.51), (7.8666; 2.70), (7.8623; 2.31), (7.6066; 1.96), (7.5948; 1.91), (7.5864; 1.82), (7.5747; 1.78), (7.3828; 3.06), (6.3196; 7.87), (4.0393; 0.85), (4.0215; 0.84), (3.3049; 223.69), (2.7305; 0.48), (2.7191; 0.53), (2.6939; 6.95), (2.6824; 6.88), (2.6693; 0.63), (2.6646; 0.45), (2.6231; 0.99), (2.5789; 16.00), (2.5391; 0.83), (2.5087; 22.53), (2.5044; 40.54), (2.5000; 52.50), (2.4957; 36.63), (2.4915; 18.05), (2.3310; 0.34), (2.3225; 0.85), (2.2212; 10.86), (2.1698; 0.60), (1.9868; 3.67), (1.1927; 1.02), (1.1749; 2.01), (1.1571; 1.00), (−0.0002; 0.97) |

-continued
| | | | | |
|---|---|---|---|---|
| 9 | 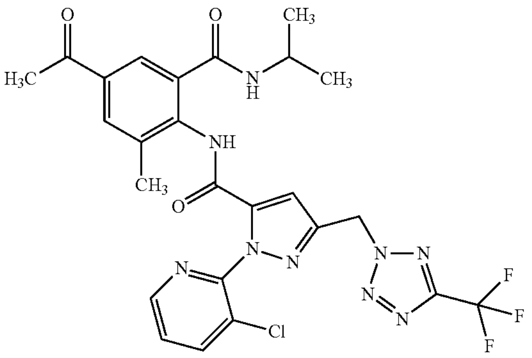 | 2.94 | 590 | (10.3872; 2.90), (8.4727; 2.00), (8.4690; 1.96), (8.4609; 2.08), (8.4573; 1.87), (8.1478; 1.98), (8.1441; 1.83), (8.1275; 2.20), (8.1239; 1.94), (8.1025; 1.58), (8.0833; 1.55), (7.9203; 2.70), (7.9168; 2.71), (7.8023; 2.89), (7.7980; 2.62), (7.6024; 1.90), (7.5907; 1.88), (7.5822; 1.77), (7.5705; 1.67), (7.3829; 3.48), (6.3215; 8.33), (4.0390; 0.36), (4.0217; 0.36), (3.9529; 0.66), (3.9361; 1.02), (3.9178; 0.99), (3.9018; 0.63), (3.3040; 331.95), (2.6735; 0.51), (2.6689; 0.62), (2.6246; 0.64), (2.5797; 16.00), (2.5389; 1.40), (2.5043; 69.68), (2.5000; 84.86), (2.4961; 59.63), (2.3268; 0.96), (2.2324; 11.63), (2.1639; 0.42), (1.9867; 1.49), (1.1927; 0.50), (1.1749; 0.89), (1.1571; 0.43), (1.0887; 0.56), (1.0720; 0.64), (1.0370; 14.81), (1.0205; 14.60), (−0.0002; 1.85) |
| 10 | 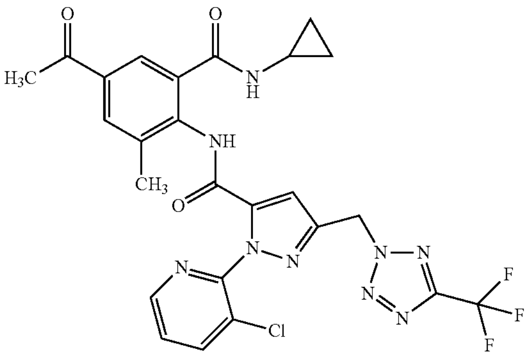 [SMILES: CC(=O)c1cc(C)c(NC(=O)c2cc(Cn3nnc(C(F)(F)F)n3)nn2-c2ncccc2Cl)c(C(=O)NC2CC2)c1] | 2.73 | 588 | (10.4009; 2.73), (10.1948; 0.35), (8.4852; 2.02), (8.4814; 2.30), (8.4735; 2.18), (8.4697; 2.27), (8.3532; 1.65), (8.3428; 1.64), (8.1664; 0.40), (8.1577; 2.11), (8.1540; 2.09), (8.1375; 2.14), (8.1338; 2.07), (7.9132; 2.41), (7.9098; 2.48), (7.7917; 2.67), (7.7872; 2.47), (7.6643; 0.33), (7.6078; 1.99), (7.5960; 1.98), (7.5876; 1.94), (7.5826; 0.55), (7.5758; 1.82), (7.5607; 0.35), (7.3903; 3.26), (7.3571; 0.57), (6.3261; 8.07), (4.0392; 0.56), (4.0213; 0.61), (3.3041; 433.90), (2.7272; 0.33), (2.7164; 0.58), (2.7068; 0.79), (2.6984; 1.24), (2.6887; 1.24), (2.6797; 1.01), (2.6696; 1.17), (2.6645; 0.75), (2.6159; 0.83), (2.5706; 16.00), (2.5390; 1.62), (2.5086; 43.35), (2.5043; 77.99), (2.4999; 99.19), (2.4956; 69.88), (2.3263; 0.99), (2.3070; 1.51), (2.2251; 10.94), (2.1720; 0.64), (2.1608; 1.41), (1.9867; 2.53), (1.9078; 0.48), (1.1926; 0.70), (1.1748; 1.35), (1.1571; 0.67), (0.7787; 0.32), (0.7714; 0.36), (0.6284; 0.77), (0.6157; 2.06), (0.6104; 2.66), (0.5982; 2.55), (0.5924; 2.30), (0.5811; 0.96), (0.5752; 0.45), (0.4471; 0.91), (0.4366; 2.61), (0.4303; 2.49), (0.4266; 2.35), (0.4209; 2.20), (0.4086; 0.84), (−0.0002; 1.84) |

-continued
| | | | | |
|---|---|---|---|---|
| 11 | 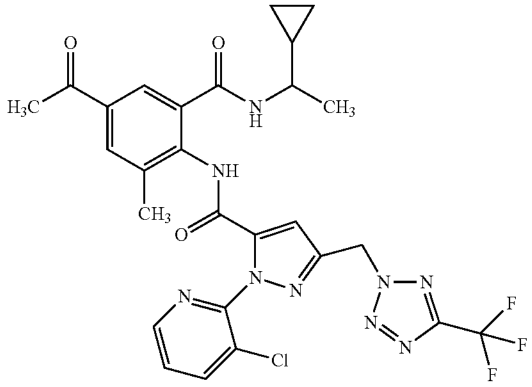 [SMILES: CC(=O)c1cc(C)c(NC(=O)c2cc(Cn3nnc(C(F)(F)F)n3)nn2-c2ncccc2Cl)c(C(=O)NC(C)C2CC2)c1] | 3.23 | 616 | (10.386; 2.96), (8.477; 2.05), (8.473; 2.08), (8.465; 2.16), (8.461; 1.99), (8.172; 1.63), (8.149; 2.80), (8.145; 2.18), (8.128; 2.20), (8.125; 1.94), (7.933; 2.64), (7.930; 2.66), (7.814; 2.87), (7.810; 2.63), (7.604; 1.96), (7.593; 1.90), (7.584; 1.81), (7.572; 1.74), (7.379; 3.54), (6.317; 8.40), (3.310; 368.48), (3.288; 3.46), (2.675; 0.36), (2.671; 0.47), (2.666; 0.35), (2.586; 16.00), (2.540; 1.01), (2.510; 28.26), (2.506; 49.14), (2.501; 61.32), (2.497; 42.84), (2.328; 0.49), (2.234; 11.52), (1.988; 0.82), (1.176; 0.46), (1.078; 6.85), (1.061; 6.75), (0.858; 0.40), (0.850; 0.54), (0.838; 1.00), (0.826; 0.73), (0.817; 0.98), (0.805; 0.59), (0.798; 0.39), (0.371; 0.47), (0.362; 0.98), (0.354; 0.82), (0.350; 0.88), (0.341; 1.05), (0.328; 0.53), (0.319; 0.41), (0.224; 0.59), (0.214; 0.82), (0.207; 0.94), (0.203; 1.02), (0.193; 1.25), (0.188; 1.09), (0.179; 1.03), (0.172; 1.05), (0.167; 1.40), (0.156; 1.17), (0.148; 1.00), (0.144; 0.96), (0.136; 1.11), (0.128; 1.08), (0.115; 0.73), (0.105; 0.46), (0.001; 0.48) |
| 12 | 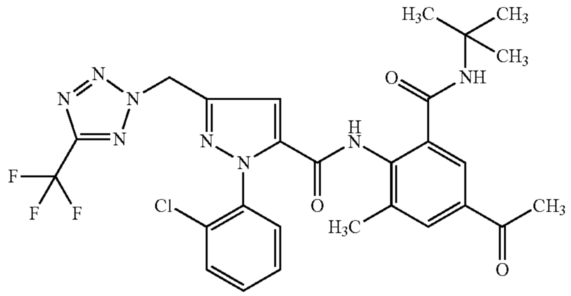 [SMILES: CC(=O)c1cc(C)c(NC(=O)c2cc(Cn3nnc(C(F)(F)F)n3)nn2-c2ccccc2Cl)c(C(=O)NC(C)(C)C)c1] | 3.76 | 603 | (10.2653; 0.87), (7.8981; 0.95), (7.7560; 0.93), (7.7139; 0.81), (7.5783; 0.54), (7.5650; 0.87), (7.4827; 0.84), (7.4709; 1.68), (7.4603; 0.84), (7.4581; 0.83), (7.4487; 0.74), (7.3187; 1.00), (6.8705; 0.55), (6.6603; 0.33), (6.3134; 1.99), (3.6120; 0.85), (3.6105; 0.49), (3.6079; 0.46), (3.6064; 0.38), (3.6051; 0.62), (3.6010; 2.03), (3.5969; 0.64), (3.5941; 0.46), (3.5914; 0.48), (3.5900; 0.87), (3.3557; 1.15), (3.3446; 421.02), (3.3321; 0.84), (3.3209; 7.92), (2.6915; 1.41), (2.6175; 0.47), (2.6144; 0.62), (2.6114; 0.46), (2.5891; 0.94), (2.5784; 5.20), (2.5422; 0.37), (2.5236; 0.99), (2.5219; 1.57), (2.5208; 1.40), (2.5176; 1.13), (2.5088; 30.78), (2.5057; 69.35), (2.5027; 96.24), (2.4996; 69.24), (2.4966; 31.05), (2.3899; 0.41), (2.3869; 0.59), (2.3838; 0.43), (2.2677; 0.69), (2.2178; 3.24), (2.1829; 0.94), (2.0767; 0.75), (1.7707; 0.84), (1.7656; 0.73), (1.7629; 0.45), (1.7596; 2.37), (1.7565; 0.48), (1.7537; 0.73), (1.7486; 0.83), (1.5513; 0.35), (1.3855; 0.32), (1.3544; 7.77), (1.2607; 0.53), (1.2545; 0.34), (1.2494; 0.33), (1.2460; 0.47), (1.2367; 0.47), (1.2111; 16.00), (0.0053; 1.18), (−0.0002; 42.61), (−0.0057; 1.09) |

-continued
| | | | | |
|---|---|---|---|---|
| 13 | 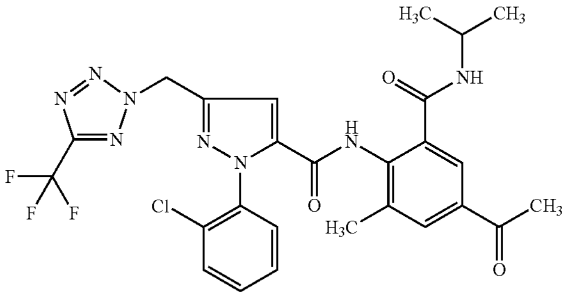 [SMILES: CC(=O)c1cc(C)c(NC(=O)c2cc(Cn3nnc(C(F)(F)F)n3)nn2-c2ccccc2Cl)c(C(=O)NC(C)C)c1] | 3.46 | 589 | (10.3449; 0.96), (10.1893; 0.45), (10.1413; 0.72), (8.2680; 0.44), (8.2001; 0.77), (8.1886; 0.78), (7.9886; 0.53), (7.9763; 0.45), (7.9635; 0.48), (7.9243; 1.89), (7.8884; 0.47), (7.8076; 1.61), (7.7473; 0.47), (7.7108; 0.87), (7.6102; 0.85), (7.6075; 0.86), (7.5700; 0.75), (7.5657; 1.98), (7.5572; 1.01), (7.5531; 2.65), (7.5499; 1.97), (7.5339; 0.41), (7.4879; 2.31), (7.4849; 1.56), (7.4748; 4.20), (7.4654; 2.89), (7.4521; 2.42), (7.4499; 2.33), (7.4414; 1.50), (7.4375; 2.18), (7.4271; 1.03), (7.4056; 0.37), (7.4029; 0.34), (7.3475; 1.40), (7.3186; 1.55), (7.0325; 0.34), (6.8708; 1.34), (6.6615; 0.79), (6.3053; 6.58), (6.0878; 0.96), (3.9490; 0.46), (3.9379; 0.98), (3.9268; 1.52), (3.9153; 1.53), (3.9037; 1.06), (3.8931; 0.48), (3.8458; 0.42), (3.8354; 0.57), (3.8251; 0.42), (3.6010; 0.33), (3.3724; 1.01), (3.3510; 904.54), (3.3273; 5.08), (2.6288; 3.42), (2.6179; 0.63), (2.6149; 0.82), (2.6119; 0.61), (2.6088; 0.33), (2.5830; 14.46), (2.5425; 0.37), (2.5242; 1.04), (2.5211; 1.31), (2.5180; 1.31), (2.5091; 40.92), (2.5061; 89.30), (2.5031; 122.81), (2.5001; 89.47), (2.4972; 40.22), (2.4673; 0.35), (2.4051; 0.45), (2.3903; 0.56), (2.3873; 0.77), (2.3843; 0.56), (2.3258; 2.26), (2.3000; 0.73), (2.2715; 0.46), (2.2547; 0.72), (2.2273; 7.19), (2.2075; 6.53), (2.1830; 2.47), (2.1772; 3.88), (2.1698; 0.79), (2.1617; 2.49), (2.1367; 0.33), (2.0766; 1.12), (1.7596; 0.39), (1.3546; 16.00), (1.1768; 0.32), (1.1659; 0.34), (1.1611; 0.37), (1.1582; 0.67), (1.1480; 0.69), (1.1268; 6.11), (1.1165; 6.11), (1.0835; 3.09), (1.0726; 3.10), (1.0667; 0.90), (1.0549; 1.55), (1.0432; 1.33), (1.0269; 12.07), (1.0159; 12.07), (1.0066; 5.18), (1.0006; 1.54), (0.9956; 4.67), (0.9774; 0.36), (0.0052; 0.42), (−0.0002; 14.01), (−0.0057; 0.43) |

-continued
| | | | | |
|---|---|---|---|---|
| 14 | 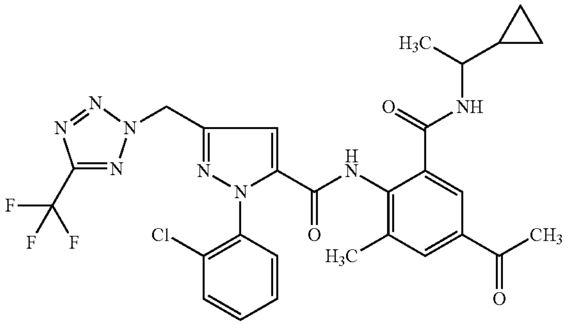 [SMILES: CC(=O)c1cc(C)c(NC(=O)c2cc(Cn3nnc(C(F)(F)F)n3)nn2-c2ccccc2Cl)c(C(=O)NC(C)C2CC2)c1] | 3.74 | 615 | (10.3352; 0.96), (8.2806; 0.44), (8.2533; 0.67), (8.2332; 0.67), (7.9317; 2.10), (7.8934; 0.38), (7.8888; 0.34), (7.8218; 1.82), (7.5717; 0.93), (7.5678; 1.16), (7.5642; 0.74), (7.5543; 1.11), (7.5506; 2.45), (7.5470; 1.38), (7.5416; 0.38), (7.5310; 0.34), (7.5011; 0.71), (7.4939; 0.88), (7.4853; 1.12), (7.4783; 1.91), (7.4716; 1.26), (7.4596; 4.72), (7.4538; 2.75), (7.4426; 1.68), (7.4384; 0.58), (7.4332; 0.43), (7.4290; 0.56), (7.4225 ; 0.35), (7.3408; 2.04), (6.8717; 0.66), (6.6428; 0.34), (6.2962; 6.10), (6.0801; 0.83), (3.3553; 65.57), (3.3507; 68.70), (3.3479; 66.64), (3.3463; 66.86), (3.3400; 99.77), (3.3165; 2.23), (3.2947; 0.61), (2.6323; 2.06), (2.5877; 16.00), (2.5677; 0.33), (2.5254; 0.68), (2.5121; 14.82), (2.5076; 30.85), (2.5030; 41.15), (2.4984; 29.01), (2.4939; 15.04), (2.3264; 1.48), (2.2301; 9.12), (2.1834; 1.38), (2.1611; 1.54), (2.0730; 0.86), (1.3558; 8.10), (1.1336; 0.84), (1.1168; 0.88), (1.0758; 5.18), (1.0591; 5.16), (0.8521; 0.39), (0.8448; 0.44), (0.8320; 0.72), (0.8201; 0.59), (0.8120; 0.70), (0.7997; 0.45), (0.3795; 0.34), (0.3721; 0.53), (0.3677; 0.48), (0.3583; 0.86), (0.3520; 0.73), (0.3465; 0.84), (0.3360; 0.85), (0.3254; 0.49), (0.3166; 0.39), (0.2153; 0.36), (0.2060; 0.64), (0.2006; 0.61), (0.1916; 1.00), (0.1869; 0.92), (0.1789; 0.97), (0.1711; 1.53), (0.1583; 1.38), (0.1440; 1.37), (0.1351; 1.06), (0.1304; 1.00), (0.1230; 0.91), (0.1136; 0.61), (0.1079; 0.52), (−0.0002; 5.35) |
| 15 | 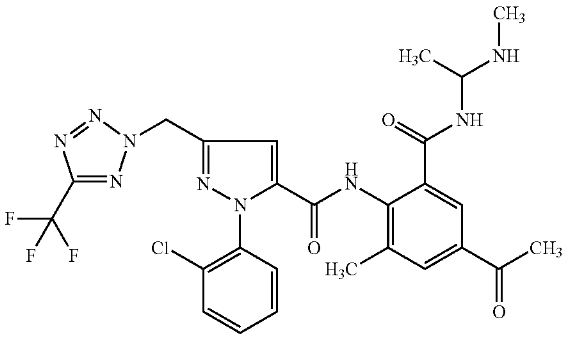 [SMILES: CNC(C)NC(=O)c1cc(C(C)=O)cc(C)c1NC(=O)c1cc(Cn2nnc(C(F)(F)F)n2)nn1-c1ccccc1Cl] | 3.05 | 561 | (10.4300; 2.91), (8.3885; 1.05), (8.3763; 1.04), (7.9230; 2.43), (7.8698; 2.48), (7.5811; 1.30), (7.5761; 1.39), (7.5610; 1.89), (7.5587; 1.84), (7.5109; 0.98), (7.5037; 1.06), (7.4961; 1.17), (7.4933; 1.47), (7.4882; 2.68), (7.4825; 2.58), (7.4768; 1.13), (7.4643; 3.22), (7.4586; 2.60), (7.4462; 1.15), (7.4413; 1.19), (7.4350; 0.42), (7.4269; 0.52), (7.4232; 0.51), (7.3383; 2.87), (6.2996; 7.29), (6.0827; 0.65), (3.3282; 475.99), (3.3048; 1.56), (2.6841; 7.87), (2.6725; 8.09), (2.5808; 16.00), (2.5407; 0.39), (2.5238; 0.98), (2.5057; 58.66), (2.5017; 77.96), (2.3326; 0.40), (2.3283; 0.53), (2.2228; 9.74), (2.0733; 3.72), (−0.0002; 6.77) |

-continued
| | | | | |
|---|---|---|---|---|
| 16 | 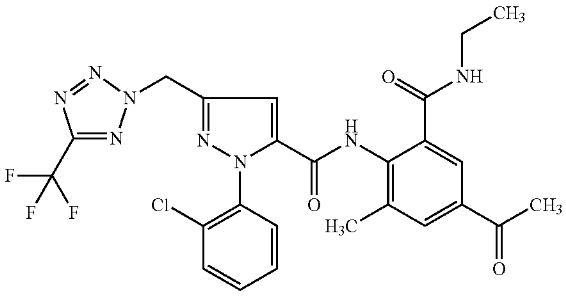 [SMILES: CCNC(=O)c1cc(C(C)=O)cc(C)c1NC(=O)c1cc(Cn2nnc(C(F)(F)F)n2)nn1-c1ccccc1Cl] | 3.27 | 575 | (10.3990; 2.81), (8.3973; 0.62), (8.3830; 1.16), (8.3707; 0.64), (7.9230; 2.21), (7.8491; 2.19), (7.8454; 2.05), (7.5754; 1.30), (7.5711; 0.90), (7.5688; 0.76), (7.5550; 2.25), (7.5512; 1.37), (7.5469; 0.37), (7.5028; 1.08), (7.4950; 1.53), (7.4794; 4.23), (7.4705; 0.41), (7.4626; 2.13), (7.4596; 2.19), (7.4549; 2.11), (7.4465; 0.73), (7.4437; 0.68), (7.4371; 1.27), (7.4227; 0.49), (7.4190; 0.63), (7.4138; 0.33), (7.3390; 2.65), (6.3005; 6.90), (6.0836; 0.72), (3.3254; 340.98), (3.3021; 0.99), (3.1962; 0.57), (3.1784; 1.96), (3.1643; 2.10), (3.1604; 2.13), (3.1464; 2.02), (3.1283; 0.61), (2.6752; 0.32), (2.6706; 0.46), (2.6657; 0.37), (2.5828; 16.00), (2.5406; 0.37), (2.5238; 0.83), (2.5192; 1.18), (2.5058; 47.11), (2.5015; 64.08), (2.4981; 41.95), (2.3282; 0.42), (2.2251; 9.11), (2.0735; 3.10), (1.0450; 0.40), (1.0297; 0.46), (1.0188; 4.12), (1.0007; 9.02), (0.9827; 4.00), (−0.0002; 9.17) |
| 17 | 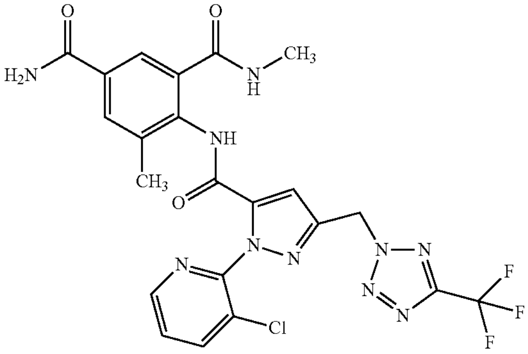 [SMILES: CNC(=O)c1cc(C(N)=O)cc(C)c1NC(=O)c1cc(Cn2nnc(C(F)(F)F)n2)nn1-c1ncccc1Cl] | 1.94 | 563 | (10.3958; 3.78), (8.4852; 2.98), (8.4831; 3.14), (8.4775; 3.27), (8.4753; 3.14), (8.2388; 1.85), (8.2318; 1.83), (8.1647; 2.67), (8.1628; 2.68), (8.1512; 2.82), (7.9826; 2.69), (7.8299; 4.10), (7.8131; 4.04), (7.6054; 2.26), (7.5975; 2.39), (7.5920; 2.41), (7.5842; 2.20), (7.4305; 2.55), (7.3781; 4.75), (6.3252; 10.76), (3.6009; 0.47), (3.3487; 551.50), (3.3253; 3.91), (3.0756; 0.33), (2.7065; 0.45), (2.6988; 0.53), (2.6750; 11.14), (2.6674; 11.21), (2.6146; 0.81), (2.5421; 0.54), (2.5056; 93.86), (2.5030; 119.62), (2.5003; 93.38), (2.3873; 0.77), (2.2676; 0.63), (2.1811; 16.00), (2.1388; 0.77), (1.7595; 0.47), (1.3545; 2.74), (1.2355; 0.42), (1.1056; 1.03), (−0.0002; 9.41) |
| 18 | 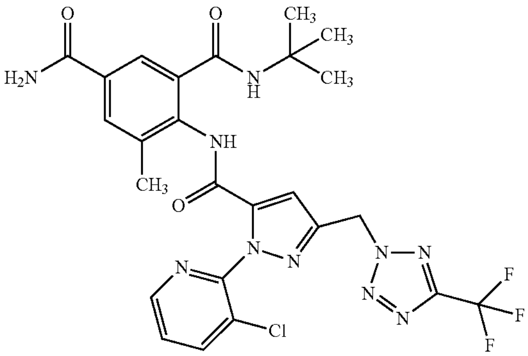 | 2.5 | 605 | (8.4806; 0.74), (8.4782; 0.79), (8.4728; 0.81), (8.4703; 0.83), (8.1661; 0.73), (8.1636; 0.72), (8.1527; 0.76), (8.1502; 0.75), (8.0132; 0.60), (7.8006; 0.88), (7.7981; 0.94), (7.7350; 0.85), (7.7326; 0.81), (7.6084; 0.80), (7.6006; 0.80), (7.5950; 0.74), (7.5872; 0.75), (7.4146; 0.55), (7.3379; 1.32), (6.3338; 2.89), (6.3009; 0.35), (3.6121; 0.52), (3.6078; 0.37), (3.6051; 0.50), (3.6011; 1.27), (3.5971; 0.50), (3.5943; 0.35), (3.5901; 0.53), (3.3514; 72.68), (3.3278; 0.42), (3.0759; 0.85), (2.5093; 5.36), (2.5064; 10.86), (2.5034; 14.50), (2.5004; 10.52), (2.4975; 4.93), (2.1796; 4.26), (2.0728; 0.42), (1.7704; 0.54), (1.7652; 0.59), (1.7594; 1.60), (1.7550; 0.84), (1.7485; 0.53), (1.2365; 2.26), (1.2170; 16.00), (1.1057; 2.67), (−0.0002; 1.54) |

-continued
| | | | | |
|---|---|---|---|---|
| 19 | 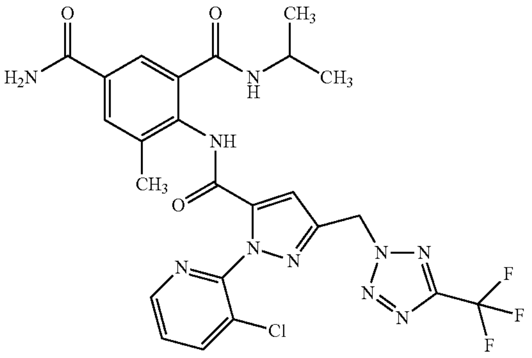 | 2.27 | 591 | (10.3287; 1.73), (8.4822; 2.57), (8.4752; 2.65), (8.1619; 2.35), (8.01487; 2.44), (8.0273; 1.62), (8.0112; 3.37), (7.8295; 3.78), (7.777, 3; 3.57), (7.6120; 1.80), (7.6042; 1.94), (7.5988; 1.93), (7.5909; 1.79), (7.4458; 2.38), (7.3874; 4.19), (6.3388; 9.13), (3.9582; 0.35), (3.9472; 0.86), (3.9360; 1.35), (3.9247; 1.36), (3.9135; 0.87), (3.9024; 0.35), (3.3667; 122.03), (3.3434; 3.13), (3.0856; 0.39), (2.6249; 0.42), (2.5744; 0.58), (2.5133; 44.84), (2.2435; 0.40), (2.2002; 13.88), (1.1152; 1.28), (1.0351; 16.00), (1.0242; 15.82) |
| 20 | 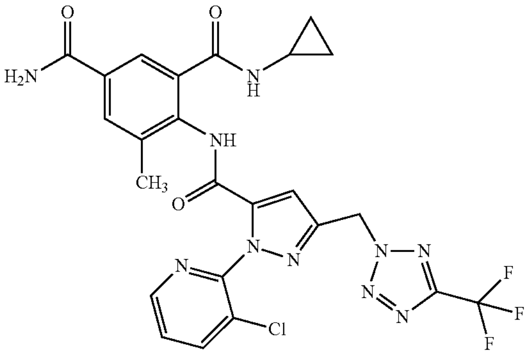 | 2.11 | 589 | (10.3270; 4.42), (8.4844; 3.18), (8.4780; 3.25), (8.2779; 2.92), (8.2717; 2.83), (8.1629; 2.86), (8.1492; 2.92), (7.9791; 3.18), (7.8200; 4.55), (7.7497; 4.46), (7.6073; 2.16), (7.5996; 2.40), (7.5941; 2.37), (7.5863; 2.09), (7.4289; 3.17), (7.3860; 5.63), (6.3335; 11.16), (3.3451; 188.53), (3.3216; 5.52), (2.6974; 1.39), (2.6918; 1.88), (2.6854; 1.87), (2.6799; 1.43), (2.6148; 0.89), (2.5641; 0.79), (2.5028; 120.76), (2.3871; 0.79), (2.2327; 0.49), (2.1836; 16.00), (2.0864; 0.55), (2.0768; 0.46), (1.8815; 0.49), (1.1057; 0.81), (0.6107; 1.33), (0.5999; 4.54), (0.5911; 4.36), (0.4194; 4.99), (−0.0002; 6.30) |
| 21 | 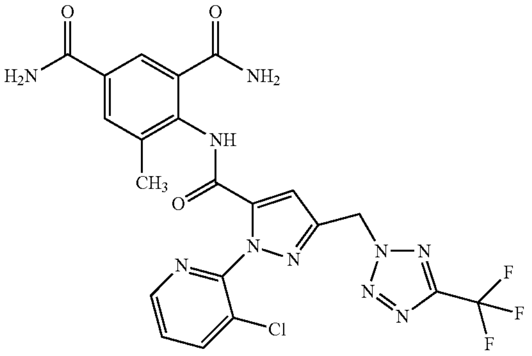 [SMILES: Cc1cc(C(N)=O)cc(C(N)=O)c1NC(=O)c1cc(Cn2nnc(C(F)(F)F)n2)nn1-c1ncccc1Cl] | 1.83 | 549 | (10.4564; 3.10), (8.4954; 3.09), (8.4929; 3.30), (8.4876; 3.37), (8.4850; 3.32), (8.1681; 3.18), (8.1656; 3.21), (8.1547; 3.38), (8.1522; 3.21), (7.9852; 2.22), (7.8871; 3.37), (7.8841; 3.66), (7.8308; 3.44), (7.8283; 3.27), (7.7370; 2.29), (7.6087; 3.17), (7.6009; 3.13), (7.5953; 3.13), (7.5875; 3.22), (7.4848; 2.29), (7.4418; 2.18), (7.3731; 5.89), (6.8726; 0.37), (6.3199; 10.36), (3.6146; 0.33), (3.6121; 1.41), (3.6106; 0.96), (3.6078; 0.87), (3.6051; 1.22), (3.6010; 3.38), (3.5969; 1.23), (3.5942; 0.87), (3.5913; 0.94), (3.5899; 1.44), (3.5874; 0.33), (3.3794; 0.42), (3.3583; 198.38), (3.3348; 1.17), (3.0759; 0.56), (2.5655; 0.45), (2.5250; 0.55), (2.5220; 0.70), (2.5188; 0.71), (2.5100; 13.67), (2.5070; 29.29), (2.5040; 40.11), (2.5009; 29.16), (2.4980; 13.61), (2.2344; 0.43), (2.1842; 0.78), (2.1703; 16.00), (2.0869; 0.33), (1.7699; 1.42), (1.7648; 1.38), (1.7622; 0.96), (1.7589; 4.20), (1.7558; 0.97), (1.7531; 1.38), (1.7479; 1.41), (1.6996; 0.38), (1.3560; 4.78), (1.1056; 1.82), (−0.0002; 1.17) |

-continued
| | | | | |
|---|---|---|---|---|
| 22 | 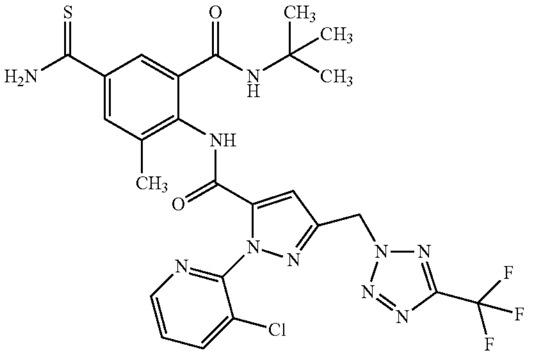 | 2.89 | 621 | (10.2718; 1.25), (9.9252; 0.50), (9.5218; 0.53), (8.4795; 0.73), (8.4771; 0.77), (8.4717; 0.80), (8.4692; 0.79), (8.1657; 0.66), (8.1633; 0.67), (8.1523; 0.72), (8.1498; 0.70), (7.8188; 0.85), (7.8159; 0.93), (7.7020; 0.90), (7.6989; 0.88), (7.6083; 0.67), (7.6005; 0.68), (7.5949; 0.67), (7.5871; 0.66), (7.5253; 1.14), (7.3421; 1.73), (6.3348; 2.79), (3.3492; 80.09), (3.3257; 1.00), (2.5210; 0.33), (2.5179; 0.36), (2.5089; 7.23), (2.5060; 15.19; 2.5030; 20.65), (2.5000; 15.01), (2.4970; 7.02), (2.1756; 3.99), (2.1659; 0.36), (1.9901; 1.16), (1.3968; 0.47), (1.2219; 1.62), (1.2149; 16.00), (1.1862; 0.35), (1.1744; 0.66), (−0.0002; 2.17) |
| 23 | 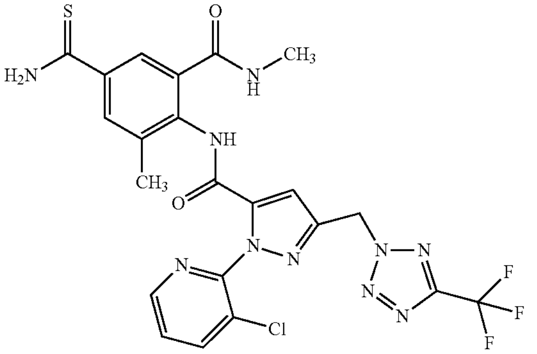 | 2.26 | 579 | (10.3697; 4.37), (9.8866; 1.85), (9.4617; 1.97), (8.4844; 3.19), (8.4806; 3.36), (8.4726; 3.48), (8.4689; 3.48), (8.4579; 0.34), (8.1830; 1.77), (8.1713; 1.80), (8.1581; 3.39), (8.1544; 3.12), (8.1379; 3.33), (8.1342; 3.11), (7.8302; 4.46), (7.8152; 4.32), (7.6052; 2.97), (7.5934; 2.95), (7.5849; 2.82), (7.5732; 2.75), (7.3696; 4.69), (7.3188; 0.33), (6.3153; 11.63), (6.0975; 0.78), (4.0572; 0.65), (4.0395; 1.95), (4.0217; 1.97), (4.0039; 0.68), (3.3161; 559.41), (3.2928; 6.09), (3.2623; 0.34), (2.6841; 11.40), (2.6726; 11.48), (2.5398; 0.49), (2.5230; 1.31), (2.5097; 19.61), (2.5053; 36.60), (2.5008; 47.75), (2.4964; 32.89), (2.4920; 15.61), (2.3274; 0.34), (2.1782; 16.00), (2.0691; 0.63), (1.9870; 8.58), (1.1928; 2.39), (1.1750; 4.68), (1.1572; 2.32), (−0.0002; 2.53) |
| 24 | 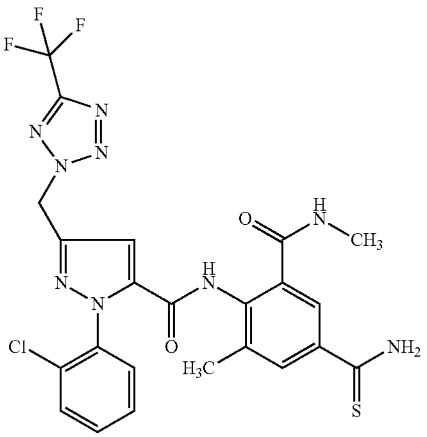 [SMILES: CNC(=O)c1cc(C(N)=S)cc(C)c1NC(=O)c1cc(Cn2nnc(C(F)(F)F)n2)nn1-c1ccccc1Cl] | 2.65 | 578 | (10.2916; 4.32), (9.8819; 1.75), (9.4577; 1.83), (8.2270; 0.63), (8.2165; 1.82), (8.2050; 1.81), (8.1932; 0.62), (7.8305; 4.53), (7.8198; 4.80), (7.8149; 2.79), (7.5770; 1.85), (7.5721; 1.78), (7.5567; 2.81), (7.5531; 2.20), (7.5463; 0.37), (7.5061; 1.47), (7.5003; 1.99), (7.4946; 1.85), (7.4881; 2.06), (7.4837; 4.49), (7.4808; 5.69), (7.4750; 1.69), (7.4627; 5.00), (7.4569; 3.95), (7.4515; 0.92), (7.4450; 1.32), (7.4396; 1.76), (7.4251; 0.67), (7.4212; 0.56), (7.3201; 5.50), (6.2900; 11.94), (3.3147; 722.62), (3.2927; 5.80), (3.2389; 0.33), (2.6763; 10.43), (2.6649; 10.51), (2.5397; 0.88), (2.5228; 2.87), (2.5095; 38.24), (2.5052; 70.82), (2.5007; 92.02), (2.4963; 63.26), (2.4919; 29.94), (2.3368; 0.34), (2.3320; 0.50), (2.3274; 0.60), (2.3227; 0.45), (2.1791; 16.00), (−0.0002; 1.19) |

-continued
| | | | | |
|---|---|---|---|---|
| 25 | 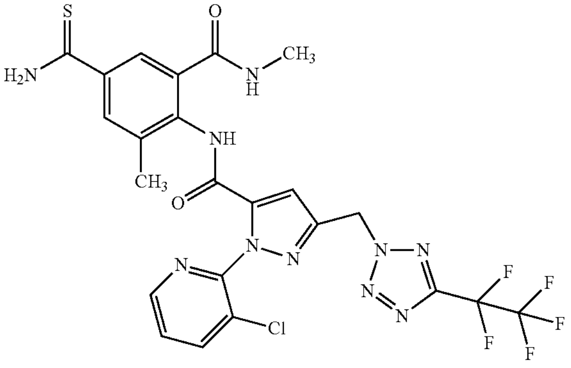 [SMILES: CNC(=O)c1cc(C(N)=S)cc(C)c1NC(=O)c1cc(Cn2nnc(C(F)(F)C(F)(F)F)n2)nn1-c1ncccc1Cl] | 2.64 | 629 | (10.4089; 3.99), (10.3860; 0.41), (9.9370; 1.95), (9.5003; 2.06), (8.4852; 2.60), (8.4828; 2.67), (8.4774; 2.82), (8.4749; 2.88), (8.2327; 0.64), (8.2254; 1.86), (8.2177; 1.85), (8.2102; 0.61), (8.1641; 2.64), (8.1617; 2.56), (8.1507; 2.87), (8.1483; 2.64), (7.8356; 3.07), (7.8328; 3.95), (7.8100; 3.87), (7.8070; 3.29), (7.6050; 2.54), (7.5972; 2.54), (7.5915; 2.65), (7.5837; 2.67), (7.3841; 6.09), (7.3350; 0.55), (6.3543; 9.75), (6.3280; 0.52), (6.1394; 0.81), (5.7617; 0.35), (3.3502; 147.58), (3.3267; 1.79), (2.6758; 10.39), (2.6682; 10.94), (2.5213; 0.35), (2.5181; 0.39), (2.5091; 10.42), (2.5063; 21.88), (2.5033; 29.69), (2.5003; 21.61), (2.4976; 10.07), (2.1794; 16.00), (2.1719; 1.96), (1.9904; 0.58), (−0.0002; 3.94) |
| 26 | 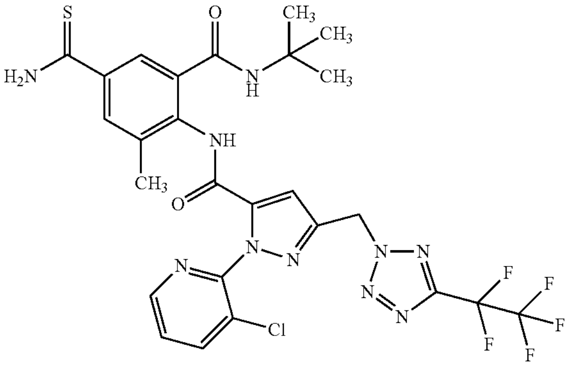 [SMILES: Cc1cc(C(N)=S)cc(C(=O)NC(C)(C)C)c1NC(=O)c1cc(Cn2nnc(C(F)(F)C(F)(F)F)n2)nn1-c1ncccc1Cl] | 3.26 | 671 | (10.2893; 0.88), (9.9271; 0.48), (9.5240; 0.52), (8.4796; 0.81), (8.4771; 0.86), (8.4718; 0.93), (8.4693; 0.94), (8.1634; 0.82), (8.1609; 0.80), (8.1499; 0.90), (8.1474; 0.84), (7.8212; 0.83), (7.8184; 0.97), (7.7046; 0.86), (7.7015; 0.86), (7.6073; 0.80), (7.5994; 0.81), (7.5938; 0.88), (7.5860; 0.88), (7.5194; 1.04), (7.3554; 1.66), (6.3605; 2.67), (5.7616; 0.52), (3.3500; 39.38), (2.5094; 2.44), (2.5064; 5.45), (2.5033; 7.60), (2.5003; 5.51), (2.4973; 2.50), (2.1758; 4.09), (2.1652; 0.45), (1.2184; 2.49), (1.2135; 16.00), (−0.0002; 1.49) |
| 27 | 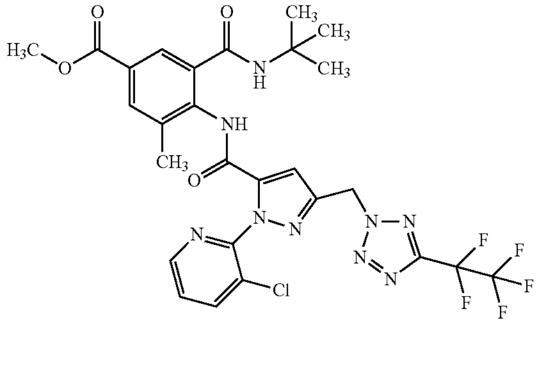 [SMILES: COC(=O)c1cc(C)c(NC(=O)c2cc(Cn3nnc(C(F)(F)C(F)(F)F)n3)nn2-c2ncccc2Cl)c(C(=O)NC(C)(C)C)c1] | 3.85 | 670 | (10.3211; 0.73), (8.4760; 0.71), (8.4722; 0.75), (8.4642; 0.80), (8.4605; 0.76), (8.1550; 0.57), (8.1514; 0.56), (8.1348; 0.67), (8.1313; 0.62), (7.8866; 0.78), (7.7682; 0.71), (7.6398; 0.63), (7.6049; 0.62), (7.5930; 0.65), (7.5847; 0.59), (7.5729; 0.60), (7.3494; 0.74), (6.3482; 2.08), (3.8556; 5.51), (3.3124; 133.11), (3.2890; 1.76), (2.5095; 5.50), (2.5052; 10.34), (2.5007; 13.56), (2.4963; 9.43), (2.4919; 4.52), (2.2135; 3.08), (1.9870; 0.39), (1.2089; 16.00), (1.1932; 0.36), (−0.0002; 0.75) |

-continued
| | | | | |
|---|---|---|---|---|
| 28 | 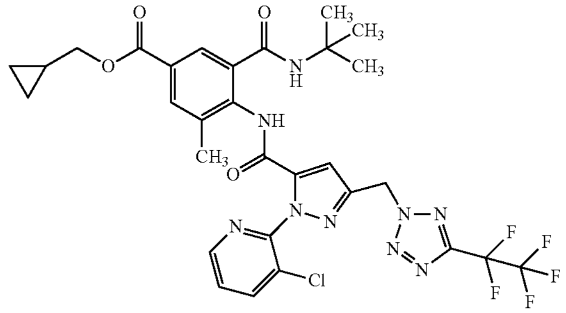 [SMILES: Cc1cc(C(=O)OCC2CC2)cc(C(=O)NC(C)(C)C)c1NC(=O)c1cc(Cn2nnc(C(F)(F)C(F)(F)F)n2)nn1-c1ncccc1Cl] | 4.54 | 710 | (10.3478; 0.90), (8.4792; 0.65), (8.4766; 0.68), (8.4713; 0.74), (8.4688; 0.75), (8.1663; 0.62), (8.1638; 0.60), (8.1529; 0.66), (8.1503; 0.62), (7.8934; 0.72), (7.8911; 0.81), (7.7620; 0.79), (7.7589; 0.81), (7.6622; 0.94), (7.6082; 0.61), (7.6004; 0.62), (7.5948; 0.65), (7.5870; 0.65), (7.3602; 1.42), (6.3617; 2.08), (4.1342; 1.61), (4.1221; 1.60), (3.3433; 215.19), (3.3301; 0.39), (3.3197; 0.74), (2.6144; 0.33), (2.5238; 0.48), (2.5207; 0.62), (2.5175; 0.70), (2.5088; 17.53), (2.5057; 38.08), (2.5027; 52.28), (2.4996; 37.49), (2.4966; 16.62), (2.3869; 0.32), (2.2213; 3.35), (2.2101; 0.40), (2.0865; 16.00), (2.0768; 2.02), (1.2273; 0.42), (1.2141; 0.43), (1.2067; 2.17), (1.2011; 13.16), (0.8502; 0.40), (0.5688; 0.82), (0.5659; 0.87), (0.5630; 0.39), (0.5588; 0.39), (0.5554; 0.83), (0.5525; 0.82), (0.3555; 0.91), (0.3531; 0.90), (0.3478; 0.81), (0.3452; 0.95), (−0.0002; 8.06) |
| 29 | 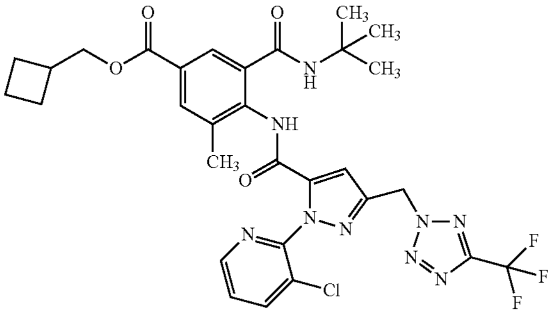 [SMILES: Cc1cc(C(=O)OCC2CCC2)cc(C(=O)NC(C)(C)C)c1NC(=O)c1cc(Cn2nnc(C(F)(F)F)n2)nn1-c1ncccc1Cl] | 4.62 | 674 | (10.3211; 0.98), (8.4784; 0.76), (8.4746; 0.83), (8.4666; 0.89), (8.4628; 0.89), (8.1650; 0.80), (8.1613; 0.81), (8.1448; 0.93), (8.1411; 0.90), (7.8737; 0.87), (7.8705; 0.96), (7.7535; 0.94), (7.7494; 0.95), (7.6579; 1.09), (7.6101; 0.84), (7.5983; 0.81), (7.5899; 0.81), (7.5781; 0.82), (7.3473; 1.51), (6.3314; 2.52), (4.2768; 1.85), (4.2603; 1.80), (3.3246; 275.15), (2.7038; 0.38), (2.6751; 0.36), (2.6702; 0.50), (2.6657; 0.41), (2.5238; 0.73), (2.5095; 25.31), (2.5056; 44.38), (2.5014; 60.79), (2.4979; 39.41), (2.3329; 0.34), (2.3280; 0.43), (2.2174; 3.57), (2.2078; 0.62), (2.0735; 0.63), (2.0637; 0.40), (2.0547; 0.50), (2.0453; 0.62), (2.0331; 0.40), (2.0215; 0.34), (1.9058; 0.35), (1.8822; 0.54), (1.8728; 0.44), (1.8584; 0.49), (1.8538; 0.68), (1.8439; 0.60), (1.8380; 0.58), (1.8259; 0.55), (1.8024; 0.55), (1.7807; 0.37), (1.3697; 0.46), (1.2119; 3.09), (1.2044; 16.00), (1.1670; 0.44), (0.0081; 0.62), (−0.0002; 23.28), (−0.0085; 0.59) |

-continued
| | | | | |
|---|---|---|---|---|
| 30 | 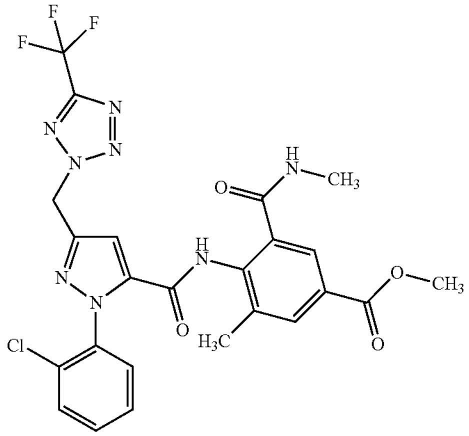 [SMILES: CNC(=O)c1cc(C(=O)OC)cc(C)c1NC(=O)c1cc(Cn2nnc(C(F)(F)F)n2)nn1-c1ccccc1Cl] | 3.28 | 577 | (10.4073; 2.42), (8.3932; 0.36), (8.3831; 1.03), (8.3714; 1.03), (8.3602; 0.33), (7.9265; 2.11), (7.9229; 2.37), (7.8703; 2.61), (7.8657; 2.25), (7.5810; 1.11), (7.5761; 1.01), (7.5627; 1.38), (7.5609; 1.68), (7.5572; 1.30), (7.5425; 0.40), (7.5075; 0.83), (7.5011; 1.18), (7.4957; 0.99), (7.4895; 1.15), (7.4853; 2.42), (7.4817; 2.99), (7.4761; 0.89), (7.4638; 2.26), (7.4572; 2.29), (7.4517; 0.45), (7.4450; 0.84), (7.4420; 0.64), (7.4394; 1.06), (7.4326; 0.50), (7.4288; 0.51), (7.4251; 0.48), (7.4212; 0.72), (7.4185; 0.41), (7.3390; 2.67), (7.2941; 0.47), (6.3000; 6.44), (6.0831; 1.02), (3.8916; 0.46), (3.8580; 16.00), (3.5528; 0.36), (3.3330; 122.21), (2.9437; 0.42), (2.7842; 0.32), (2.7292; 0.34), (2.7176; 0.35), (2.6672; 6.96), (2.6557; 6.81), (2.6295; 0.35), (2.5244; 0.36), (2.5062; 19.52), (2.5021; 26.29), (2.2195; 9.07), (2.0738; 2.44), (−0.0002; 8.65) |
| 31 | 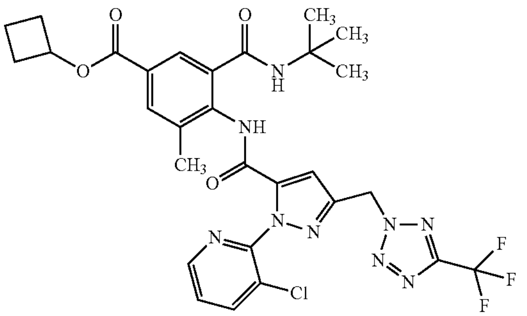 [SMILES: Cc1cc(C(=O)OC2CCC2)cc(C(=O)NC(C)(C)C)c1NC(=O)c1cc(Cn2nnc(C(F)(F)F)n2)nn1-c1ncccc1Cl] | 4.37 | 660 | (10.3164; 1.43), (8.4776; 0.99), (8.4658; 1.12), (8.1632; 0.96), (8.1430; 1.06), (7.8736; 1.32), (7.7428; 1.36), (7.6286; 1.06), (7.6121; 0.83), (7.5993; 0.74), (7.5919; 0.72), (7.5790; 0.69), (7.3407; 1.62), (6.3287; 2.80), (5.1486; 0.47), (5.1302; 0.71), (5.1110; 0.46), (3.3702; 77.28), (3.3591; 95.15), (3.3562; 93.92), (3.3524; 112.17), (2.5071; 29.32), (2.5031; 39.64), (2.4991; 28.40), (2.3804; 0.63), (2.3728; 0.53), (2.3597; 0.66), (2.3398; 0.36), (2.3346; 0.42), (2.2139; 5.01), (2.2046; 1.41), (2.1749; 0.65), (2.1490; 0.82), (2.1238; 0.60), (1.8148; 0.46), (1.7887; 0.47), (1.6696; 0.47), (1.6440; 0.41), (1.2333; 0.32), (1.2054; 16.00), (1.1655; 0.47), (0.8503; 0.36), (−0.0002; 2.32) |
| 32 | 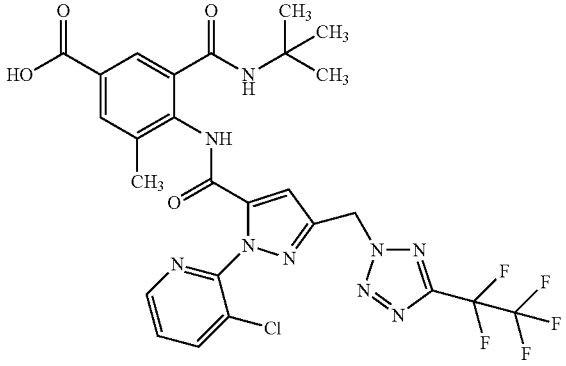 [SMILES: Cc1cc(C(=O)O)cc(C(=O)NC(C)(C)C)c1NC(=O)c1cc(Cn2nnc(C(F)(F)C(F)(F)F)n2)nn1-c1ncccc1Cl] | | 606 | (10.3184; 1.24), (8.4796; 0.75), (8.4771; 0.80), (8.4717; 0.83), (8.4692; 0.81), (8.1661; 0.75), (8.1636; 0.75), (8.1527; 0.82), (8.1502; 0.78), (7.8653; 0.86), (7.8631; 0.99), (7.7536; 0.96), (7.7506; 1.00), (7.6884; 1.23), (7.6081; 0.76), (7.6003; 0.76), (7.5947; 0.76), (7.5868; 0.76), (7.3498; 1.86), (6.3364; 2.79), (4.0344; 0.59), (4.0226; 0.60), (3.3534; 16.30), (2.5093; 3.98), (2.5064; 8.69), (2.5033; 11.98), (2.5003; 8.64), (2.4973; 3.92), (2.2061; 4.14), (2.1964; 0.52), (1.9902; 2.64), (1.9103; 0.48), (1.2184; 2.10), (1.2108; 16.00), (1.1863; 0.77), (1.1745; 1.62), (1.1626; 0.74), (−0.0002; 9.66) |

-continued
| | | | | |
|---|---|---|---|---|
| 33 | 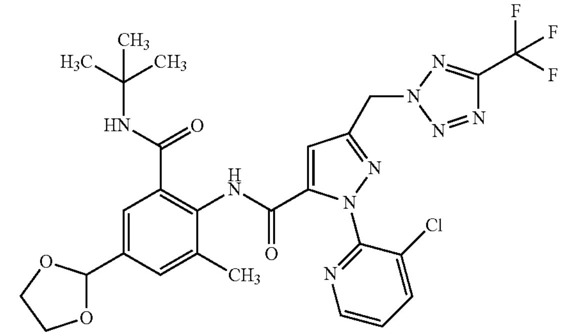 [SMILES: Cc1cc(C2OCCO2)cc(C(=O)NC(C)(C)C)c1NC(=O)c1cc(Cn2nnc(C(F)(F)F)n2)nn1-c1ncccc1Cl] | 3.22 | 634 | (10.1660; 1.05), (9.9833; 0.43), (8.4736; 0.72), (8.4698; 0.75), (8.4618; 0.77), (8.4581; 0.70), (8.1547; 0.72), (8.1509; 0.65), (8.1345; 0.79), (8.1307; 0.69), (7.6035; 0.70), (7.5917; 0.70), (7.5833; 0.67), (7.5715; 0.65), (7.3730; 1.09), (7.3550; 1.13), (7.3203; 1.86), (7.2631; 0.92), (7.2588; 0.84), (6.3284; 0.78), (6.3204; 2.81), (5.6974; 1.84), (4.0585; 0.43), (4.0407; 1.44), (4.0366; 0.82), (4.0316; 0.69), (4.0239; 0.77), (3.9503; 0.77), (3.9427; 0.71), (3.9377; 0.80), (3.9334; 1.39), (3.9159; 0.40), (3.3974; 0.50), (3.3853; 0.52), (3.3058; 215.99), (2.5390; 0.40), (2.5219; 1.34), (2.5087; 18.23), (2.5045; 33.57), (2.5000; 43.28), (2.4957; 30.18), (2.4915; 14.68), (2.2431; 0.68), (2.1550; 3.86), (1.9867; 0.74), (1.4054; 0.33), (1.2357; 0.32), (1.2224; 3.01), (1.1949; 16.00), (1.1749; 0.62), (−0.0002; 3.05) |
| 34 | 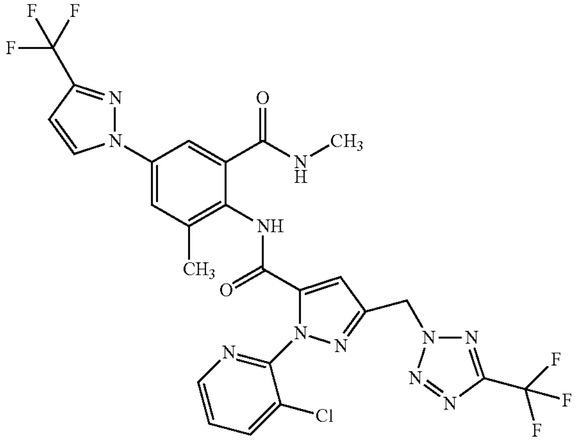 [SMILES: CNC(=O)c1cc(-n2ccc(C(F)(F)F)n2)cc(C)c1NC(=O)c1cc(Cn2nnc(C(F)(F)F)n2)nn1-c1ncccc1Cl] | 3.48 | 654 | (10.3460; 0.32), (8.7573; 2.51), (8.7545; 2.61), (8.4909; 2.99), (8.4884; 3.24), (8.4831; 3.26), (8.4806; 3.25), (8.3237; 0.58), (8.3164; 1.73), (8.3087; 1.75), (8.3010; 0.56), (8.1699; 2.86), (8.1673; 2.89), (8.1565; 3.14), (8.1539; 3.02), (7.8971; 2.85), (7.8928; 3.17), (7.7908; 3.27), (7.7866; 3.10), (7.6082; 3.00), (7.6004; 2.95), (7.5948; 2.95), (7.5870; 3.03), (7.3876; 8.21), (7.0792; 3.46), (7.0750; 3.50), (7.0604; 0.42), (7.0564; 0.40), (6.3329; 11.32), (3.5032; 0.52), (3.3657; 0.58), (3.3446; 410.60), (3.3211; 1.59), (3.3073; 2.17), (3.0757; 0.75), (2.9438; 11.83), (2.7837; 8.13), (2.6903; 10.22), (2.6826; 10.34), (2.6178; 0.57), (2.6147; 0.80), (2.6117; 0.58), (2.5424; 0.41), (2.5241; 1.16), (2.5210; 1.43), (2.5179; 1.42), (2.5090; 42.45), (2.5060; 93.55), (2.5030; 128.88), (2.4999; 94.09), (2.4970; 43.44), (2.4633; 1.25), (2.3902; 0.56), (2.3872; 0.79), (2.3842; 0.55), (2.2922; 5.52), (2.2432; 16.00), (2.0866; 9.79), (2.0771; 2.96), (1.9578; 8.49), (1.1057; 2.29), (0.0052; 0.48), (−0.0002; 16.49), (−0.0058; 0.50) |

-continued
| | | | | |
|---|---|---|---|---|
| 35 | 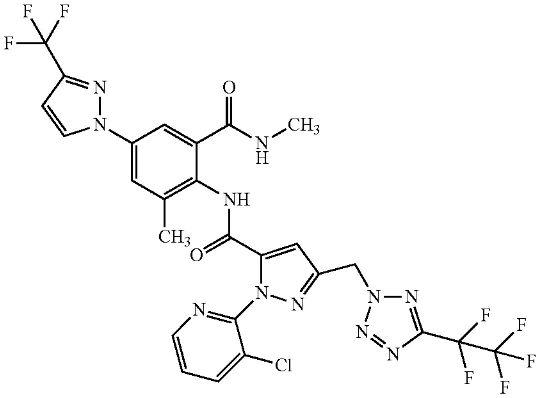 [SMILES: CNC(=O)c1cc(-n2ccc(C(F)(F)F)n2)cc(C)c1NC(=O)c1cc(Cn2nnc(C(F)(F)C(F)(F)F)n2)nn1-c1ncccc1Cl] | 3.86 | 704 | (10.3421; 4.33), (10.3199; 0.63), (8.7455; 3.04), (8.7417; 3.15), (8.4915; 2.98), (8.4877; 3.26), (8.4798; 3.56), (8.4760; 3.51), (8.4688; 0.57), (8.4649; 0.51), (8.2892; 1.84), (8.2776; 1.86), (8.1673; 2.64), (8.1636; 2.73), (8.1470; 3.24), (8.1433; 3.13), (8.1263; 0.39), (8.1225; 0.36), (7.8929; 3.28), (7.8871; 3.61), (7.7899; 3.58), (7.7840; 3.34), (7.6102; 2.92), (7.5984; 2.99), (7.5900; 2.89), (7.5847; 0.73), (7.5782; 2.86), (7.5644; 0.38), (7.3830; 6.70), (7.3348; 0.79), (7.0709; 3.97), (7.0647; 3.97), (6.3539; 9.69), (6.3278; 0.58), (6.1398; 1.06), (4.0384; 0.71), (4.0207; 0.71), (3.5372; 0.40), (3.3559; 171.00), (3.3496; 164.16), (3.3440; 204.61), (3.3397; 227.67), (3.2776; 0.47), (2.7126; 0.43), (2.6947; 10.61), (2.6832; 10.68), (2.6724; 1.12), (2.6677; 0.72), (2.5422; 0.45), (2.5120; 29.91), (2.5075; 59.85), (2.5030; 79.51), (2.4984; 58.13), (2.4939; 28.62), (2.3342; 0.38), (2.3297; 0.50), (2.3251; 0.38), (2.2443; 16.00), (2.0735; 0.59), (1.9889; 3.03), (1.3975; 1.90), (1.2350; 0.39), (1.1927; 0.83), (1.1749; 1.64), (1.1571; 0.80), (0.0079; 0.45), (−0.0002; 11.05), (−0.0085; 0.48) |
| 36 | 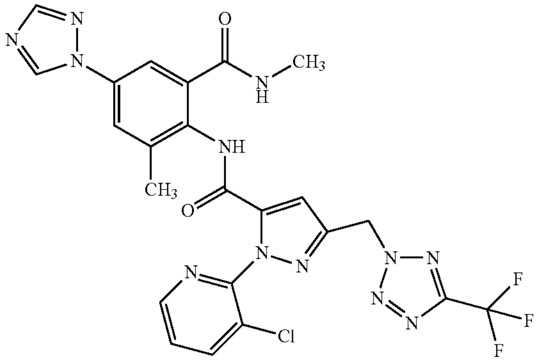 [SMILES: CNC(=O)c1cc(-n2cncn2)cc(C)c1NC(=O)c1cc(Cn2nnc(C(F)(F)F)n2)nn1-c1ncccc1Cl] | 2.25 | 587 | (10.3452; 3.05), (9.3096; 3.73), (8.4899; 2.03), (8.4875; 2.16), (8.4821; 2.15), (8.4797; 2.11), (8.3027; 0.98), (8.2954; 1.09), (8.2600; 4.43), (8.1680; 1.50), (8.1659; 1.50), (8.1546; 1.73), (8.1525; 1.56), (7.8775; 1.79), (7.7916; 1.96), (7.7882; 1.82), (7.6071; 1.41), (7.5992; 1.44), (7.5936; 1.39), (7.5858; 1.34), (7.3861; 2.94), (6.3320; 6.53), (3.5339; 0.36), (3.3971; 0.32), (3.3802; 0.80), (3.3521; 445.17), (3.3287; 2.66), (2.9620; 0.47), (2.9439; 16.00), (2.7838; 12.19), (2.6883; 7.25), (2.6807; 7.25), (2.6151; 0.42), (2.5243; 0.96), (2.5213; 1.28), (2.5180; 1.57), (2.5093; 23.60), (2.5064; 48.76), (2.5034; 66.32), (2.5004; 48.08), (2.4975; 22.16), (2.3875; 0.40), (2.2372; 8.80), (2.2237; 0.50), (2.0769; 0.95), (1.9580; 12.79), (1.5157; 0.62), (0.0052; 0.58), (−0.0002; 14.61), (−0.0057; 0.45) |

-continued
| | | | | |
|---|---|---|---|---|
| 37 | 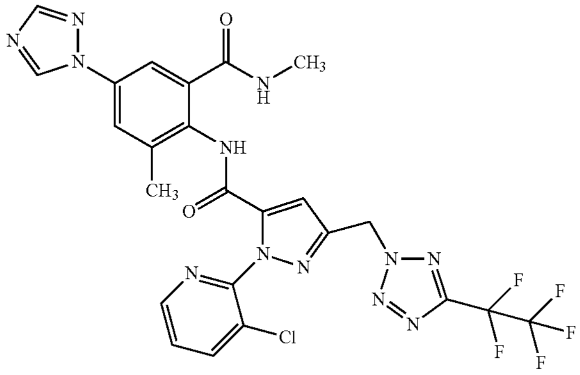 [SMILES: CNC(=O)c1cc(-n2cncn2)cc(C)c1NC(=O)c1cc(Cn2nnc(C(F)(F)C(F)(F)F)n2)nn1-c1ncccc1Cl] | | 637 | (10.3572; 4.65), (10.3346; 0.49), (9.3104; 7.64), (8.4893; 3.42), (8.4869; 3.58), (8.4815; 3.69), (8.4790; 3.88), (8.4706; 0.54), (8.4682; 0.52), (8.2991; 1.67), (8.2917; 1.73), (8.2604; 9.41), (8.1668; 2.70), (8.1645; 2.66), (8.1534; 2.98), (8.1510; 2.79), (8.1457; 0.45), (8.1320; 0.36), (8.1297; 0.34), (7.8778; 3.39), (7.7925; 3.48), (7.7890; 3.48), (7.6063; 2.60), (7.5985; 2.63), (7.5929; 2.86), (7.5850; 2.79), (7.5789; 0.39), (7.3878; 5.10), (7.3393; 0.59), (6.3589; 10.91), (6.3327; 0.66), (6.1434; 1.21), (3.5341; 0.45), (3.5027; 0.46), (3.3823; 0.35), (3.3540; 712.55), (3.3305; 3.86), (3.3050; 0.44), (2.9623; 0.48), (2.9439; 8.48), (2.7840; 6.39), (2.6876; 13.02), (2.6799; 13.19), (2.6302; 0.35), (2.6262; 0.34), (2.6185; 0.44), (2.6154; 0.60), (2.6124; 0.42), (2.5247; 0.63), (2.5216; 0.84), (2.5185; 0.88), (2.5096; 30.76), (2.5067; 66.69), (2.5037; 92.06), (2.5006; 66.71), (2.4977; 30.86), (2.3908; 0.44), (2.3879; 0.56), (2.3849; 0.40), (2.2537; 0.43), (2.2377; 16.00), (2.2303; 2.89), (2.0771; 1.37), (1.9903; 0.69), (1.9582; 6.71), (1.5160; 0.67), (1.1745; 0.36), (0.0052; 0.44), (−0.0002; 14.26), (−0.0057; 0.42) |
| 38 | 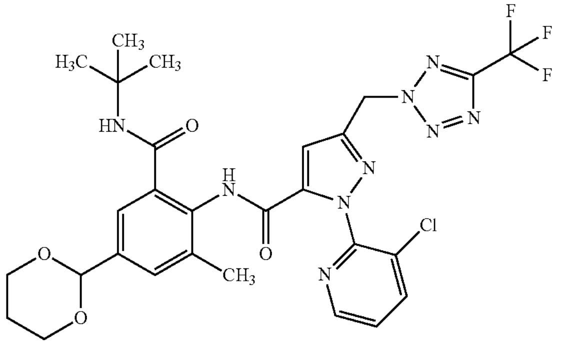 [SMILES: Cc1cc(C2OCCCO2)cc(C(=O)NC(C)(C)C)c1NC(=O)c1cc(Cn2nnc(C(F)(F)F)n2)nn1-c1ncccc1Cl] | 3.37 | 648 | (10.1405; 1.10), (8.4721; 0.70), (8.4683; 0.74), (8.4603; 0.77), (8.4565; 0.74), (8.1535; 0.68), (8.1497; 0.70), (8.1333; 0.76), (8.1296; 0.72), (7.6022; 0.71), (7.5904; 0.71), (7.5820; 0.68), (7.5702; 0.65), (7.3329; 1.18), (7.3180; 1.09), (7.3093; 2.00), (7.2395; 0.95), (7.2352; 0.87), (6.3163; 2.82), (5.4831; 1.67), (4.2944; 0.84), (4.2816; 1.72), (4.2688; 0.88), (4.1479; 0.56), (4.1354; 0.54), (4.1214; 0.64), (4.1087; 0.68), (3.9563; 0.47), (3.9500; 0.53), (3.9255; 0.79), (3.9201; 0.77), (3.8955; 0.41), (3.8893; 0.37), (3.5676; 3.31), (3.4724; 1.04), (3.4593; 1.30), (3.4564; 2.08), (3.4435; 2.04), (3.4406; 1.36), (3.4275; 1.10), (3.3098; 299.36), (3.2868; 2.00), (2.5391; 0.39), (2.5089; 12.29), (2.5046; 22.36), (2.5002; 28.79), (2.4958; 20.04), (2.4915; 9.73), (2.1387; 3.85), (1.5796; 0.97), (1.5635; 1.40), (1.5475; 0.93), (1.4535; 0.41), (1.4202; 0.36), (1.1914; 16.00), (−0.0002; 1.99) |

-continued

| | | | | |
|---|---|---|---|---|
| 39 | 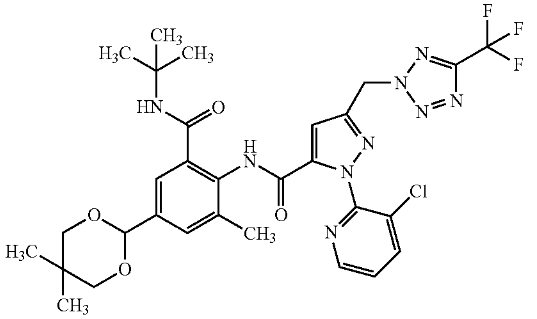 [SMILES: Cc1cc(C2OCC(C)(C)CO2)cc(C(=O)NC(C)(C)C)c1NC(=O)c1cc(Cn2nnc(C(F)(F)F)n2)nn1-c1ncccc1Cl] | 4.07 | 676 | (4.3050; 0.48), (4.2918; 0.87), (4.2787; 0.48), (3.3119; 70.85), (3.1496; 2.60), (3.1371; 2.51), (2.5092; 3.11), (2.5049; 5.73), (2.5004; 7.44), (2.4960; 5.18), (2.4916; 2.51), (1.1908; 1.28), (1.1653; 0.36), (0.7485; 16.00), (−0.0002; 0.34) |

Analytical Methods

The log P values reported in the table above and in the Preparation Examples were determined in accordance with EEC Directive 79/831 Annex V.A8 by HPLC (High Performance Liquid Chromatography) on reversed-phase columns (C 18), with the following methods:

The LC-MS determination in the acidic range is effected at pH 2.7 using 0.1% aqueous formic acid and acetonitrile (contains 0.1% formic acid) as eluents, linear gradient from 10% acetonitrile to 95% acetonitrile The calibration was effected with unbranched alkan-2-ones (having 3 to 16 carbon atoms) with known log P values (log P values determined on the basis of the retention times by linear interpolation between two successive alkanones).

The lambda max values were determined in the maxima of the chromatographic signals using the UV spectra from 200 nm to 400 nm.

The MH+ signals were determined using an Agilent MSD system with ESI and positive or negative ionization.

The NMR spectra were determined using a Bruker Avance 400 fitted with a flow probe head (volume 60 µl). The solvent used was d6-DMSO, and the reference used was tetramethylsilane (0.00 ppm). The measurement temperature is 303K if d6-DMSO is used as the solvent.

In individual cases, the samples were determined with a Bruker Avance II 600 or III 600.

USE EXAMPLES

Example 1

Myzus Test (MYZUPE Spray Treatment)

Solvent: 78 parts by weight of acetone 1.5 parts by weight of dimethylformamide

Emulsifier: 0.5 part by weight of alkylaryl polyglycol ether

To produce an appropriate active ingredient formulation, 1 part by weight of active ingredient is mixed with the stated amounts of solvent and emulsifier, and the concentrate is diluted with emulsifier-containing water to the desired concentration.

Leaf discs of Chinese cabbage (*Brassica pekinensis*) infested by all stages of the green peach aphid (*Myzus persicae*) are sprayed with an active ingredient formulation of the desired concentration.

After 6 days, the efficacy in % is determined 100% means that all aphids have been killed; 0% means that no aphids have been killed.

In this test, for example, the following compounds of the Preparation Examples show an efficacy of 100% at an application rate of 100 g/ha: 1, 7, 17, 23, 25, 26, 33, 36

In this test, for example, the following compounds of the Preparation Examples show an efficacy of 80% at an application rate of 100 g/ha: 21, 37

In this test, for example, the following compounds of the Preparation Examples show an efficacy of 90% at an application rate of 100 g/ha: 2, 5, 18, 22, 24, 27

Example 2

Phaedon Test (PHAECO Spray Treatment)

Solvent: 78.0 parts by weight of acetone 1.5 parts by weight of dimethylformamide Emulsifier: 0.5 part by weight of alkylaryl polyglycol ether To produce an appropriate active ingredient formulation, 1 part by weight of active ingredient is mixed with the stated amounts of solvent and emulsifier, and the concentrate is diluted with emulsifier-containing water to the desired concentration.

Leaf discs of Chinese cabbage (*Brassica pekinensis*) are sprayed with an active ingredient formulation of the desired concentration and, after drying, populated with larvae of the mustard beetle (*Phaedon cochleariae*).

After 7 days, the efficacy in % is determined 100% means that all beetle larvae have been killed; 0% means that no beetle larvae have been killed.

In this test, for example, the following compounds of the Preparation Examples show an efficacy of 100% at an application rate of 100 g/ha: 2, 3, 4, 5, 11, 13, 17, 18, 19, 21, 22, 23, 24, 25, 26, 27, 34, 35, 36, 37.

In this test, for example, the following compounds of the Preparation Examples show an efficacy of 83% at an application rate of 100 g/ha: 20.

Example 3

*Spodoptera frugiperda* Test (SPODFR Spray Treatment)

Solvent: 78.0 parts by weight of acetone 1.5 parts by weight of dimethylformamide Emulsifier: 0.5 part by weight of alkylaryl polyglycol ether To produce an appropriate active ingredient formulation, 1 part by weight of active ingredient is mixed with the stated amounts of solvent and emulsifier, and the concentrate is diluted with emulsifier-containing water to the desired concentration.

Leaf discs of maize (*Zea mays*) are sprayed with an active ingredient formulation of the desired concentration and, after drying, populated with caterpillars of the armyworm (*Spodoptera frugiperda*).

After 7 days, the efficacy in % is determined 100% means that all caterpillars have been killed; 0% means that no caterpillars have been killed.

In this test, for example, the following compounds of the Preparation Examples show an efficacy of 100% at an application rate of 100 g/ha: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 32, 33, 34, 35, 36, 37, 38, 39.

Example 4

*Lucilia cuprina* Test (LUCICU)

Species: *Lucilia cuprina* 1st larval stage (age: 24 hours)

Solvent: dimethyl sulphoxide

To prepare an appropriate active ingredient formulation, 10 mg of active ingredient are mixed with 0.5 ml of dimethyl sulphoxide and the concentrate is diluted with water to the desired concentration.

Vessels containing 1 $cm^3$ of horsemeat which had been treated with the active ingredient formulation are populated with about 20 *Lucilia* cuprina 1st instar larvae.

After 48 h, the kill in % is determined 100% means that all larvae have been killed; 0% means that no larvae have been killed.

In this test, for example, the following compounds of the Preparation Examples show an efficacy of 100% at an application rate of 100 ppm: 1, 2, 3, 4, 5, 6, 7.

Example 5

*Musca domestica* Test (MUSCDO)

Solvent: dimethyl sulphoxide

To prepare an appropriate active ingredient formulation, 10 mg of active ingredient are mixed with 0.5 ml of dimethyl sulphoxide and the concentrate is diluted with water to the desired concentration.

Vessels containing a sponge treated with the active ingredient preparation of the desired concentration are populated with 10 adult *Musca domestica.*

After 2 days, the kill in % is determined 100% means that all flies have been killed; 0% means that no flies have been killed.

In this test, for example, the following compounds of the Preparation Examples show an efficacy of 90% at an application rate of 100 ppm: 2, 6.

In this test, for example, the following compounds of the Preparation Examples show an efficacy of 100% at an application rate of 100 ppm: 1, 4.

Example 6

Phaedon Test (PHAECO Spray Treatment)

Solvent: 78.0 parts by weight of acetone 1.5 parts by weight of dimethylformamide Emulsifier: 0.5 part by weight of alkylaryl polyglycol ether To produce an appropriate active ingredient formulation, 1 part by weight of active ingredient is mixed with the stated amounts of solvent and emulsifier, and the concentrate is diluted with emulsifier-containing water to the desired concentration. Leaf discs of Chinese cabbage (*Brassica pekinensis*) are sprayed with an active ingredient formulation of the desired concentration and, after drying, populated with larvae of the mustard beetle (*Phaedon cochleariae*).

After the desired period of time, the effect in % is determined. 100% means that all beetle larvae have been killed; 0% means that no beetle larvae have been killed.

In this test, for example, the following compounds of the Preparation Examples show superior efficacy to the prior art: see table

| Substance | Structure | Object | Concentration | % activity |
|---|---|---|---|---|
| Example No. 23 inventive | 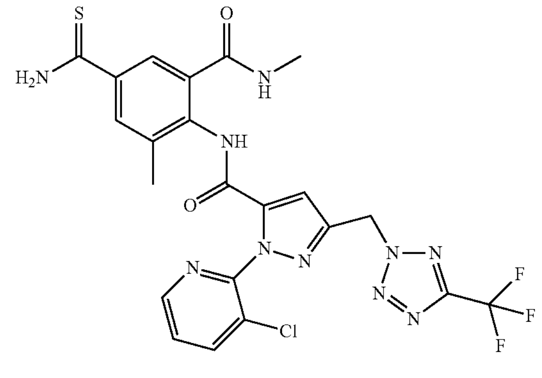 [SMILES: CNC(=O)c1cc(C(N)=S)cc(C)c1NC(=O)c1cc(Cn2nnc(C(F)(F)F)n2)nn1-c1ncccc1Cl] | PHAECO | 20 g/ha | 100 7 d |
| Comparative Example known (WO2007/144100) | 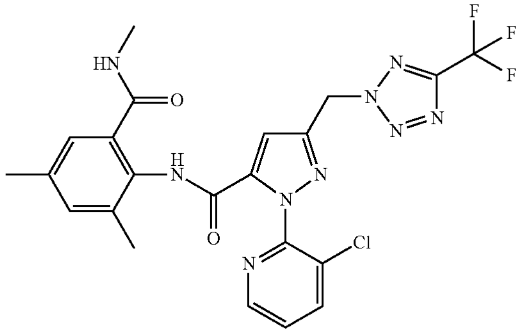 [SMILES: CNC(=O)c1cc(C)cc(C)c1NC(=O)c1cc(Cn2nnc(C(F)(F)F)n2)nn1-c1ncccc1Cl] | PHAECO | 20 g/ha | 0 7 d |

The invention claimed is:

1. An anthranilamide of the formula (I)

(I)

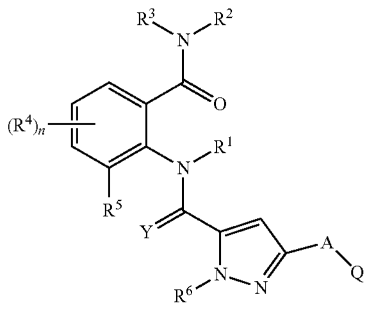

or an N-oxide and/or salt thereof, in which $R^1$ is hydrogen, methyl, cyclopropyl, cyanomethyl, methoxymethyl, methylthiomethyl, methylsulphinylmethyl or methylsulphonylmethyl, $R^2$ is hydrogen or methyl, $R^3$ is hydrogen; or is optionally singly or multiply, identically or differently substituted $C_1$-$C_6$-alkyl or $C_1$-$C_6$-alkoxy, where the substituents are each independently halogen, cyano, nitro, hydroxyl, $C_1$-$C_6$-alkyl, $C_3$-$C_6$-cycloalkyl, $C_1$-$C_4$-alkoxy, $C_1$-$C_4$-haloalkoxy, $C_1$-$C_4$-alkylthio, $C_1$-$C_4$-alkylsulphinyl, $C_1$-$C_4$-alkylsulphonyl, $C_1$-$C_4$-alkylsulphimino, $C_1$-$C_4$-alkylsulphimino-$C_1$-$C_4$-alkyl, $C_1$-$C_4$-alkylsulphimino-$C_2$-$C_5$-alkylcarbonyl, $C_1$-$C_4$-alkylsulphoximino, $C_1$-$C_4$-alkyl sulphoximino-$C_1$-$C_4$-alkyl, $C_1$-$C_4$-alkyl sulphoximino-$C_2$-$C_5$-alkylcarbonyl, $C_2$-$C_6$-alkoxycarbonyl, $C_2$-$C_6$-alkylcarbonyl or $C_3$-$C_6$-trialkylsilyl; or is optionally singly or multiply, identically or differently substituted $C_3$-$C_6$-cycloalkyl, where the substituents are each independently halogen, cyano, nitro, hydroxyl, $C_1$-$C_6$-alkyl, $C_3$-$C_6$-cycloalkyl, $C_1$-$C_4$-alkoxy, $C_1$-$C_4$-haloalkoxy, $C_1$-$C_4$-alkylthio, $C_1$-$C_4$-alkylsulphinyl, $C_1$-$C_4$-alkylsulphonyl, $C_1$-$C_4$-alkylsulphimino, $C_1$-$C_4$-alkylsulphimino-$C_1$-$C_4$-alkyl, $C_1$-$C_4$-alkylsulphimino-$C_2$-$C_5$-alkylcarbonyl, $C_1$-$C_4$-alkylsulphoximino, $C_1$-$C_4$-alkylsulphoximino-$C_1$-$C_4$-alkyl, $C_1$-$C_4$-alkylsulphoximino-$C_2$-$C_5$-alkylcarbonyl, $C_2$-$C_6$-alkoxycarbonyl, $C_2$-$C_6$-alkylcarbonyl, or $C_3$-$C_6$-trialkylsilyl, Y is O or S, $R^4$ is carboxyl, methoxymethyl, methylsulphonyloxy, methoxycarbonyl, hydroxyiminomethyl, hydroxyiminoethyl, acetyl, trifluoroacetyl, hydroxyethyl, aminocarbonyl, methylaminocarbonyl, dimethylaminocarbonyl, aminothiocarbonyl, methylaminothiocarbonyl, dimethylaminothiocarbonyl, cyclopropylmethyloxycarbonyl, cyclobutylmethyloxycarbonyl, cyclobutyloxycarbonyl, 1,3-dioxane, dimethyl-1,3-dioxane, 1,3-dioxolane, trifluoromethylpyrazole or triazole, n is 1 to 3, $R^5$ is $C_1$-$C_4$-alkyl, $C_3$-$C_6$-cycloalkyl, $C_1$-$C_4$-haloalkyl, $C_1$-$C_6$-halocycloalkyl, $C_2$-$C_6$-alkenyl, $C_2$-$C_4$-haloalkenyl, $C_2$-$C_4$-alkynyl, $C_2$-$C_4$-haloalkynyl, $C_1$-$C_4$-alkoxy, $C_1$-$C_4$-haloalkoxy, fluorine, chlorine, bromine, iodine, cyano, nitro or $C_3$-$C_6$-trialkylsilyl, $R^6$ is methyl or

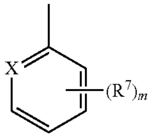

$R^7$ is independently hydrogen, halogen or $C_1$-$C_4$-haloalkyl m is 1 or 2,

X is N, CH, CF, CCl or CBr,

A is —$CH_2$—, —$CH(CH_3)$, $C(CH_3)_2$ or $CH_2CH_2$, and

Q is an optionally mono-substituted 5-membered aromatic heterocyclic ring Q-58 or Q-59 having the respective formulas

Q-58

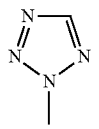

and

Q-59

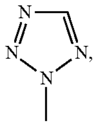

where the substituents are $C_1$-$C_3$-alkyl, $C_1$-$C_3$-haloalkyl, $C_1$-$C_2$-alkoxy, halogen, cyano, hydroxyl, nitro or $C_1$-$C_2$-haloalkoxy or are phenyl or a 5- or 6-membered heteroaromatic ring in which the phenyl or heteroaromatic ring is optionally mono- or polysubstituted identically or differently by $C_1$-$C_6$-alkyl, $C_2$-$C_6$-alkenyl, $C_2$-$C_6$-alkynyl, $C_3$-$C_6$-cycloalkyl, $C_1$-$C_6$-haloalkyl, $C_2$-$C_6$-haloalkenyl, $C_2$-$C_6$-haloalkynyl, $C_3$-$C_6$-halocycloalkyl, halogen, CN, $NO_2$, $C_1$-$C_4$-alkoxy, or $C_1$-$C_4$-haloalkoxy.

2. An anthranilamide according to claim 1, wherein Y is O.

3. An anthranilamide according to claim 1, wherein Y is S.

4. A process for preparing an anthranilamide according to claim 1, in which Y is O, comprising (A) reacting an aniline of formula (II)

(II)

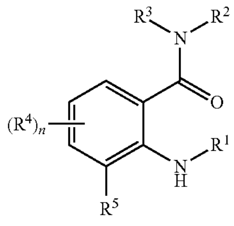

with a carbonyl chloride of formula (III)

(III)

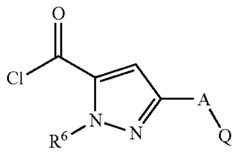

in the presence of an acid binder, or (B) reacting an aniline of formula (II)

(II)

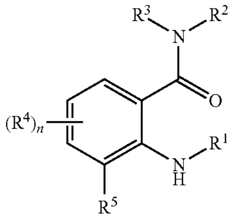

with a carboxylic acid of formula (IV)

(IV)

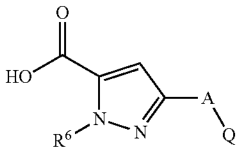

in the presence of a condensing agent, or (C) synthesizing an anthranilamide of formula (I) in which $R^1$ is hydrogen by reacting a benzoxazinone of formula (V)

(V)

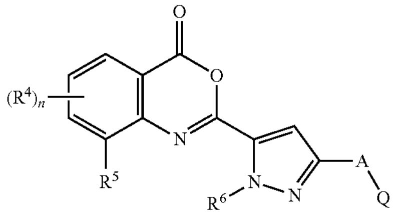

with an amine of formula (XV)

(XV)

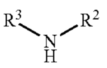

in the presence of a diluent.

5. A composition comprising at least one anthranilamide according to claim 1, and at least one further insecticide, fungicide, bactericide, acaricide, nematicide and/or a plant growth regulator.

6. An agrochemical composition comprising at least one anthranilamide according to claim 1, and at least one extender and/or surfactant.

7. A process for producing an agrochemical composition, comprising mixing at least one anthranilamide according to claim 1 with at least one extender and/or surfactant.

8. An anthranilamide according to claim 1 adapted for control of animal pests.

9. A method for controlling animal pests, comprising allowing an anthranilamide according to claim 1 to act on animal pests and/or a habitat thereof and/or on seed.

10. A composition comprising at least one anthranilamide according to claim 2, and at least one further insecticide, fungicide, bactericide, acaricide, nematicide and/or a plant growth regulator.

11. A composition comprising at least one anthranilamide according to claim 3, and at least one further insecticide, fungicide, bactericide, acaricide, nematicide and/or a plant growth regulator.

12. A process for producing agrochemical compositions, comprising mixing a composition according to claim 5 with at least one extender and/or surfactant.

13. A method for controlling animal pests, comprising allowing a composition according to claim 5 to act on animal pests and/or a habitat thereof and/or on seed.

14. An agrochemical composition comprising at least one anthranilamide according to claim 2, and at least one extender and/or surfactant.

15. An agrochemical composition comprising at least one anthranilamide according to claim 3 and at least one extender and/or surfactant.

16. A compound according to claim 1, wherein $R^1$ and $R^2$ are hydrogen, $R^3$ is methyl, ethyl, isopropyl, tert-butyl, or cyanomethyl, Y is oxygen, and n is 1.

17. A compound according to claim 16, wherein $R^5$ is methyl and $R^6$ is

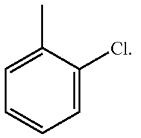

18. A compound according to claim 16, wherein $R^5$ is methyl and $R^6$ is

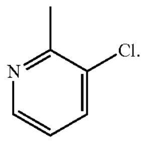

19. A compound according to claim 1, wherein Q is Q-58.

20. One or more compounds according to claim 1 selected from the group consisting of (a) a compound having the formula

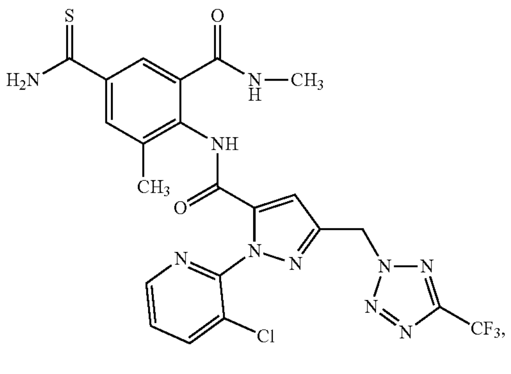 [SMILES: CNC(=O)c1cc(C(N)=S)cc(C)c1NC(=O)c1cc(Cn2nnc(C(F)(F)F)n2)nn1-c1ncccc1Cl]

(b) a compound having the formula
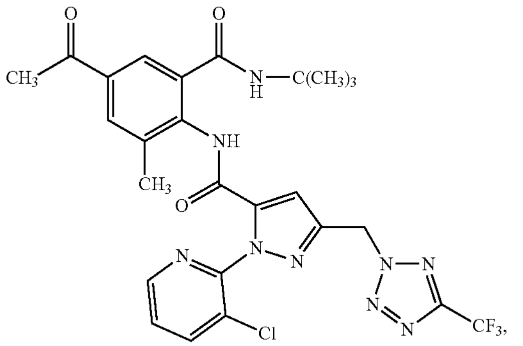 [SMILES: CC(=O)c1cc(C)c(NC(=O)c2cc(Cn3nnc(C(F)(F)F)n3)nn2-c2ncccc2Cl)c(C(=O)NC(C)(C)C)c1]
(c) a compound having the formula
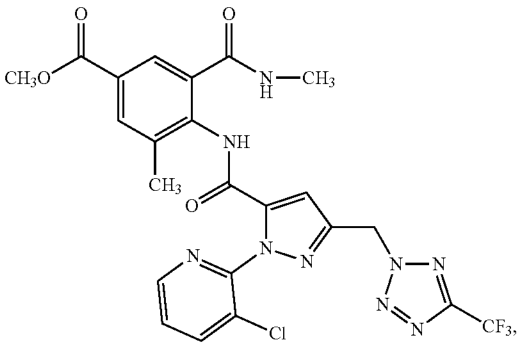
(d) a compound having the formula
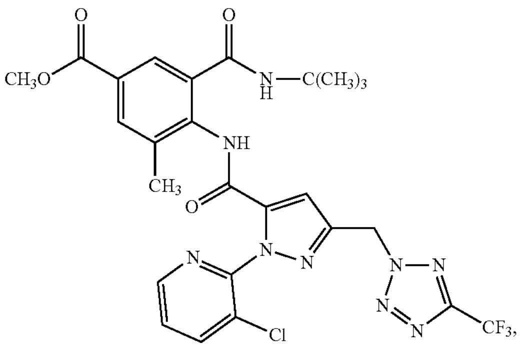
(e) a compound having the formula
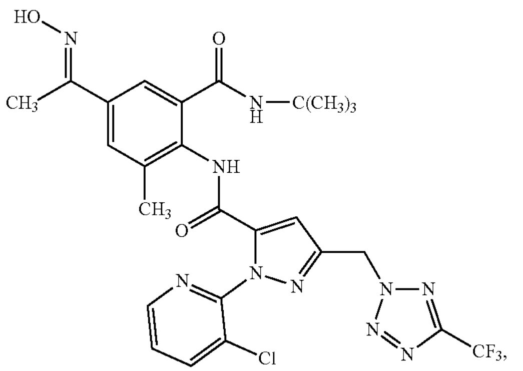 [SMILES: C/C(=N\O)c1cc(C)c(NC(=O)c2cc(Cn3nnc(C(F)(F)F)n3)nn2-c2ncccc2Cl)c(C(=O)NC(C)(C)C)c1]
(f) a compound having the formula
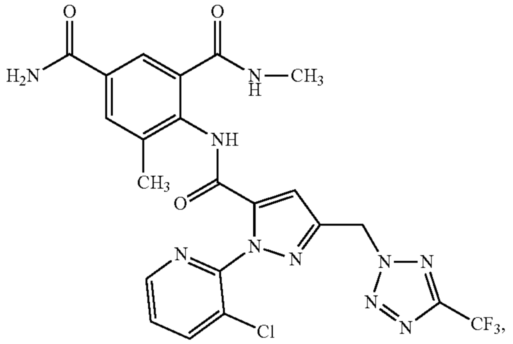 [SMILES: CNC(=O)c1cc(C(N)=O)cc(C)c1NC(=O)c1cc(Cn2nnc(C(F)(F)F)n2)nn1-c1ncccc1Cl]
(g) a compound having the formula
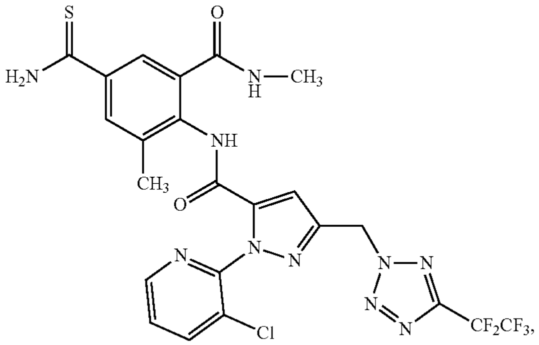
(h) a compound having the formula
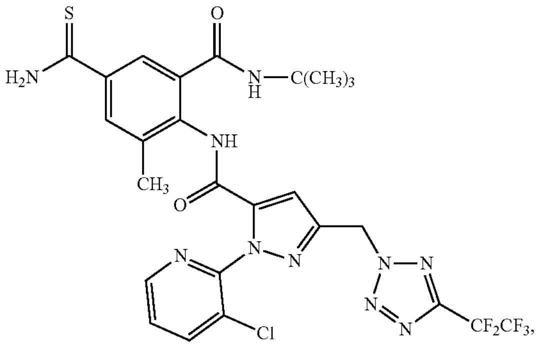

and
(i) a compound having the formula
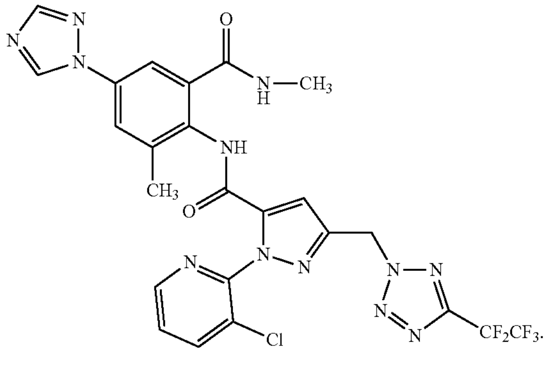
* * * * *